(12) United States Patent
Patel et al.

(10) Patent No.: US 11,452,833 B2
(45) Date of Patent: Sep. 27, 2022

(54) PATIENT INTERFACES

(71) Applicant: Fisher & Paykel Healthcare Limited, Auckland (NZ)

(72) Inventors: Roheet Patel, Auckland (NZ); Michael John Henri Cox, Auckland (NZ); Max Leon Betteridge, Auckland (NZ); Bruce Michael Walls, Auckland (NZ); Ronan Leahy, Auckland (NZ); Matthew James Pedersen, Auckland (NZ); Jae Yun Lim, Auckland (NZ)

(73) Assignee: Fisher & Paykel Healthcare Limited., Auckland (NZ)

( * ) Notice: Subject to any disclaimer, the term of this patent is extended or adjusted under 35 U.S.C. 154(b) by 597 days.

(21) Appl. No.: 16/335,414

(22) PCT Filed: Oct. 5, 2017

(86) PCT No.: PCT/IB2017/056136
§ 371 (c)(1),
(2) Date: Mar. 21, 2019

(87) PCT Pub. No.: WO2018/065926
PCT Pub. Date: Apr. 12, 2018

(65) Prior Publication Data
US 2020/0016356 A1 Jan. 16, 2020

Related U.S. Application Data

(60) Provisional application No. 62/413,604, filed on Oct. 27, 2016, provisional application No. 62/413,280, (Continued)

(51) Int. Cl.
*A61M 16/06* (2006.01)
*A61M 16/20* (2006.01)

(52) U.S. Cl.
CPC .... *A61M 16/0616* (2014.02); *A61M 16/0683* (2013.01); *A61M 16/208* (2013.01);
(Continued)

(58) Field of Classification Search
CPC ............ A61J 15/0003; A61M 16/0057; A61M 16/0066; A61M 16/06; A61M 16/0605;
(Continued)

(56) References Cited

U.S. PATENT DOCUMENTS

| 1,229,050 A | 6/1917 | Donald |
| 1,445,010 A | 2/1923 | Feinberg |

(Continued)

FOREIGN PATENT DOCUMENTS

| AU | 2004201337 A1 | 10/2005 |
| CN | 103153379 A | 6/2013 |

(Continued)

OTHER PUBLICATIONS

May 5, 2020 Extended European Search Report from EP 17857947.0 (9 pgs).

(Continued)

*Primary Examiner* — Annette Dixon
(74) *Attorney, Agent, or Firm* — Knobbe, Martens, Olson & Bear, LLP

(57) ABSTRACT

A mask assembly can include a mask seal. In some configurations, the mask assembly can be configured to be fully positioned lower than a bridge of a nose of a face of a user and to provide an exposed bridge of the nose of the user. The mask seal can comprise a nasal region comprising at least one nasal opening, a first paddle on a first side of the nasal region and a second paddle on a second side of the nasal region. The first paddle is configured to contact one side of the nose of the user and the second paddle is configured to contact the other side of the nose of the user.

17 Claims, 68 Drawing Sheets

Related U.S. Application Data filed on Oct. 26, 2016, provisional application No. 62/404,341, filed on Oct. 5, 2016.

(52) U.S. Cl.
CPC ............... *A61M 2210/0618* (2013.01); *A61M 2210/0625* (2013.01)

(58) Field of Classification Search
CPC .......... A61M 16/0611; A61M 16/0616; A61M 16/0622; A61M 16/0633; A61M 16/0638; A61M 16/0644; A61M 16/065; A61M 16/0666; A61M 16/0683; A61M 16/0694; A61M 16/0816; A61M 16/0825; A61M 16/0841; A61M 16/0858; A61M 16/0875; A61M 16/20; A61M 16/206; A61M 16/208; A61M 16/209; A61M 2016/0661; A61M 2202/0085; A61M 2202/0225; A62B 18/025; B29C 2791/001; B29C 45/1676

See application file for complete search history.

(56) References Cited

U.S. PATENT DOCUMENTS

| | | | |
|---|---|---|---|
| 2,228,218 A | 1/1941 | Schwartz | |
| 2,353,643 A | 7/1944 | Bulbulian | |
| 2,403,046 A | 7/1946 | Bulbulian | |
| 2,415,846 A | 2/1947 | Randall | |
| 2,578,621 A * | 12/1951 | Yant | A62B 18/025 128/206.24 |
| 2,706,983 A | 4/1955 | Matheson et al. | |
| 2,931,356 A | 4/1960 | Schwarz | |
| 2,939,458 A | 6/1960 | Lundquist | |
| 3,680,555 A | 8/1972 | Warncke | |
| 4,263,908 A | 4/1981 | Mizerak | |
| 4,384,577 A | 5/1983 | Huber et al. | |
| 4,470,413 A | 9/1984 | Warncke | |
| 4,907,584 A | 3/1990 | McGinnis | |
| 5,005,571 A | 4/1991 | Dietz | |
| 5,243,971 A | 9/1993 | Sullivan et al. | |
| 5,513,634 A | 5/1996 | Jackson | |
| 5,540,223 A | 7/1996 | Starr et al. | |
| 5,560,354 A | 10/1996 | Berthon-Jones et al. | |
| 5,570,689 A | 11/1996 | Starr et al. | |
| 5,896,857 A | 4/1999 | Hely et al. | |
| 6,016,804 A | 1/2000 | Gleason et al. | |
| 6,119,694 A | 9/2000 | Correa et al. | |
| 6,123,071 A | 9/2000 | Berthon-Jones et al. | |
| 6,467,483 B1 | 10/2002 | Kopacko et al. | |
| 6,470,886 B1 | 10/2002 | Jestrabek-Hart | |
| 6,491,034 B1 | 12/2002 | Gunaratnam et al. | |
| 6,584,975 B1 | 7/2003 | Taylor | |
| 6,584,977 B1 | 7/2003 | Serowski | |
| 6,644,316 B2 | 11/2003 | Bowman et al. | |
| 6,651,663 B2 | 11/2003 | Barnett et al. | |
| 6,729,333 B2 | 5/2004 | Barnett et al. | |
| 6,823,865 B2 | 11/2004 | Drew et al. | |
| 6,851,425 B2 | 2/2005 | Jaffre et al. | |
| 6,851,428 B2 | 2/2005 | Dennis | |
| 7,000,614 B2 | 2/2006 | Lang et al. | |
| 7,152,602 B2 | 12/2006 | Bateman et al. | |
| 7,260,440 B2 | 8/2007 | Selim et al. | |
| 7,353,826 B2 | 4/2008 | Sleeper et al. | |
| 7,448,386 B2 | 11/2008 | Ho et al. | |
| 7,556,043 B2 | 7/2009 | Ho et al. | |
| 7,658,189 B2 | 2/2010 | Davidson et al. | |
| 7,708,017 B2 | 5/2010 | Davidson et al. | |
| 7,721,737 B2 | 5/2010 | Radney | |
| 7,810,497 B2 | 10/2010 | Pittman et al. | |
| 7,827,990 B1 | 11/2010 | Melidis et al. | |
| 7,856,982 B2 | 12/2010 | Matula, Jr. et al. | |
| 7,942,148 B2 | 5/2011 | Davidson et al. | |
| 7,942,150 B2 | 5/2011 | Guney et al. | |
| 7,958,893 B2 | 6/2011 | Lithgow et al. | |
| 7,971,590 B2 | 7/2011 | Frater et al. | |
| 7,975,694 B2 | 7/2011 | Ho | |
| 8,042,539 B2 | 10/2011 | Chandran et al. | |
| 8,122,886 B2 | 2/2012 | Kwok et al. | |
| 8,127,764 B2 | 3/2012 | Ho et al. | |
| 8,136,524 B2 | 3/2012 | Ging et al. | |
| 8,136,525 B2 | 3/2012 | Lubke et al. | |
| 8,146,596 B2 | 4/2012 | Smith et al. | |
| 8,146,597 B2 | 4/2012 | Kwok et al. | |
| 8,205,615 B1 | 6/2012 | Ho | |
| 8,251,066 B1 | 8/2012 | Ho | |
| 8,254,637 B2 | 8/2012 | Abourizk et al. | |
| 8,261,745 B2 | 9/2012 | Chandran et al. | |
| 8,267,089 B2 | 9/2012 | Ho et al. | |
| 8,291,906 B2 | 10/2012 | Kooij et al. | |
| 8,342,181 B2 | 1/2013 | Selvarajan et al. | |
| 8,353,294 B2 | 1/2013 | Frater et al. | |
| 8,397,728 B2 | 3/2013 | D'Souza et al. | |
| 8,439,035 B2 | 5/2013 | Dantanarayana et al. | |
| 8,573,212 B2 | 11/2013 | Lynch et al. | |
| 8,616,211 B2 | 12/2013 | Davidson et al. | |
| 8,622,057 B2 | 1/2014 | Ujhazy et al. | |
| 8,646,449 B2 | 2/2014 | Browsher | |
| 8,684,004 B2 | 4/2014 | Eifler | |
| 8,701,667 B1 | 4/2014 | Ho et al. | |
| 8,720,443 B2 | 5/2014 | Kooij et al. | |
| 8,807,134 B2 | 8/2014 | Ho et al. | |
| 8,857,435 B2 | 10/2014 | Matula, Jr. et al. | |
| 8,869,797 B2 | 10/2014 | Davidson et al. | |
| 8,910,626 B2 | 12/2014 | Matula, Jr. et al. | |
| 8,931,484 B2 | 1/2015 | Melidis et al. | |
| 8,967,146 B2 | 3/2015 | Veliss et al. | |
| 8,978,653 B2 | 3/2015 | Frater et al. | |
| 8,997,742 B2 | 4/2015 | Moore et al. | |
| 9,010,330 B2 | 4/2015 | Barlow et al. | |
| 9,010,331 B2 | 4/2015 | Lang et al. | |
| 9,044,564 B2 | 6/2015 | Dravitzki et al. | |
| 9,056,177 B2 | 6/2015 | Ho | |
| 9,067,033 B2 | 6/2015 | Davidson et al. | |
| 9,095,673 B2 | 8/2015 | Barlow et al. | |
| 9,144,654 B2 | 9/2015 | Kwok | |
| 9,155,857 B2 | 10/2015 | Lalonde | |
| 9,174,018 B2 | 11/2015 | Ho et al. | |
| 9,220,860 B2 | 12/2015 | Davidson et al. | |
| 9,295,805 B2 | 3/2016 | Worboys et al. | |
| 9,381,316 B2 | 7/2016 | Ng et al. | |
| 9,399,105 B2 | 7/2016 | Frater | |
| 9,427,544 B2 | 8/2016 | Frater et al. | |
| 9,717,870 B2 | 8/2017 | Kwok et al. | |
| 9,737,678 B2 | 8/2017 | Formica et al. | |
| 9,757,534 B2 | 9/2017 | Lang et al. | |
| 9,764,107 B2 | 9/2017 | Grashow et al. | |
| 9,889,267 B2 | 2/2018 | Wells et al. | |
| 9,962,511 B2 | 5/2018 | Ng et al. | |
| 9,981,102 B2 | 5/2018 | Veliss et al. | |
| 9,993,606 B2 | 6/2018 | Gibson et al. | |
| 10,188,819 B2 | 1/2019 | Chodkowski | |
| 10,265,490 B2 | 4/2019 | Barlow et al. | |
| 10,265,492 B2 | 4/2019 | Amarasinghe et al. | |
| 2002/0096178 A1 | 7/2002 | Ziaee | |
| 2003/0127101 A1 | 7/2003 | Dennis et al. | |
| 2003/0196655 A1 | 10/2003 | Ging et al. | |
| 2005/0098183 A1 * | 5/2005 | Nash | A61M 16/06 128/206.21 |
| 2005/0199239 A1 | 9/2005 | Lang et al. | |
| 2006/0124131 A1 | 6/2006 | Chandran et al. | |
| 2006/0174887 A1 | 8/2006 | Chandran et al. | |
| 2006/0266365 A1 | 11/2006 | Stallard | |
| 2006/0283461 A1 | 12/2006 | Lubke et al. | |
| 2007/0006879 A1 | 1/2007 | Thornton | |
| 2007/0125385 A1 | 6/2007 | Ho et al. | |
| 2007/0144525 A1 | 6/2007 | Davidson et al. | |
| 2008/0041373 A1 | 2/2008 | Doshi et al. | |
| 2009/0038619 A1 | 2/2009 | Ho et al. | |
| 2009/0114229 A1 | 5/2009 | Frater et al. | |
| 2009/0120442 A1 | 5/2009 | Ho | |
| 2009/0260628 A1 | 10/2009 | Flynn | |
| 2009/0277452 A1 | 11/2009 | Lubke et al. | |

(56) References Cited

U.S. PATENT DOCUMENTS

| | | |
|---|---|---|
| 2010/0132717 A1 | 6/2010 | Davidson et al. |
| 2010/0192955 A1 | 8/2010 | Biener et al. |
| 2010/0218768 A1 | 9/2010 | Radney |
| 2010/0229872 A1 | 9/2010 | Ho |
| 2010/0313891 A1 | 12/2010 | Veliss et al. |
| 2011/0000492 A1 | 1/2011 | Veliss et al. |
| 2011/0146685 A1 | 6/2011 | Allan et al. |
| 2011/0162654 A1 | 7/2011 | Carroll et al. |
| 2011/0265796 A1 | 11/2011 | Amarasinghe et al. |
| 2011/0315143 A1 | 12/2011 | Frater |
| 2012/0067349 A1 | 3/2012 | Barlow et al. |
| 2012/0080035 A1 | 4/2012 | Guney et al. |
| 2012/0138063 A1 | 6/2012 | Eves et al. |
| 2012/0234326 A1 | 9/2012 | Mazzone et al. |
| 2013/0037033 A1 | 2/2013 | Hitchcock et al. |
| 2013/0068230 A1 | 3/2013 | Jablonski |
| 2013/0199537 A1* | 8/2013 | Formica ............ A61M 16/0616 128/205.25 |
| 2013/0213400 A1 | 8/2013 | Barlow et al. |
| 2013/0220327 A1 | 8/2013 | Barlow et al. |
| 2013/0319422 A1 | 12/2013 | Ho et al. |
| 2013/0327336 A1 | 12/2013 | Burnham et al. |
| 2014/0158136 A1 | 6/2014 | Romagnoli et al. |
| 2014/0174444 A1 | 6/2014 | Darkin et al. |
| 2014/0202464 A1 | 7/2014 | Lithgow et al. |
| 2014/0216462 A1 | 8/2014 | Law et al. |
| 2014/0224253 A1 | 8/2014 | Law et al. |
| 2014/0261432 A1 | 9/2014 | Eves et al. |
| 2014/0261435 A1 | 9/2014 | Rothermel |
| 2014/0283822 A1 | 9/2014 | Price et al. |
| 2014/0283831 A1 | 9/2014 | Foote et al. |
| 2014/0283843 A1 | 9/2014 | Eves et al. |
| 2014/0326243 A1 | 11/2014 | Znamenskiy et al. |
| 2014/0326246 A1 | 11/2014 | Chodkowski et al. |
| 2014/0352134 A1 | 12/2014 | Ho |
| 2015/0040911 A1 | 2/2015 | Davidson et al. |
| 2015/0047640 A1 | 2/2015 | McCaslin |
| 2015/0059759 A1 | 3/2015 | Frater et al. |
| 2015/0105590 A1 | 4/2015 | Xiao |
| 2015/0144139 A1 | 5/2015 | Lockhart |
| 2015/0182719 A1 | 7/2015 | Grashow et al. |
| 2015/0193650 A1 | 7/2015 | Ho et al. |
| 2015/0246199 A1 | 9/2015 | Matula, Jr. et al. |
| 2015/0352306 A1 | 12/2015 | Scheiner |
| 2015/0352308 A1 | 12/2015 | Cullen et al. |
| 2016/0001029 A1 | 1/2016 | Bayer et al. |
| 2016/0022944 A1 | 1/2016 | Chodkowski et al. |
| 2016/0082214 A1 | 3/2016 | Barlow et al. |
| 2016/0082216 A1 | 3/2016 | Lynch et al. |
| 2016/0175552 A1 | 6/2016 | Harrington |
| 2016/0271351 A1 | 9/2016 | Frater et al. |
| 2016/0296720 A1 | 10/2016 | Henry et al. |
| 2016/0367778 A1 | 12/2016 | Eves et al. |
| 2017/0000964 A1 | 1/2017 | Shafer |
| 2017/0021123 A1 | 1/2017 | Chang |
| 2017/0028153 A1 | 2/2017 | Judson et al. |
| 2017/0080174 A1 | 3/2017 | Eves et al. |
| 2017/0136200 A1 | 5/2017 | Matula, Jr. |
| 2017/0165444 A1 | 6/2017 | Rummery et al. |
| 2017/0182273 A1 | 6/2017 | Ho |
| 2017/0312467 A1 | 11/2017 | Davidson et al. |
| 2017/0326321 A1 | 11/2017 | Grashow et al. |
| 2017/0361048 A1 | 12/2017 | Moiler et al. |
| 2017/0368286 A1 | 12/2017 | Grashow et al. |
| 2018/0001044 A1 | 1/2018 | Stephens et al. |
| 2018/0071475 A1* | 3/2018 | Howard ............ A61M 16/0644 |
| 2018/0099113 A1 | 4/2018 | Bell et al. |
| 2018/0104430 A1 | 4/2018 | Ng et al. |
| 2018/0140791 A1 | 5/2018 | Jones et al. |
| 2018/0169367 A1 | 6/2018 | Chodkowski et al. |
| 2018/0236198 A1 | 8/2018 | Veliss et al. |

FOREIGN PATENT DOCUMENTS

| | | |
|---|---|---|
| DE | 3719009 | 12/1988 |
| DE | 4004157 | 4/1991 |
| EP | 1099452 | 5/2001 |
| EP | 1152787 A1 | 11/2001 |
| EP | 1258266 A1 | 11/2002 |
| EP | 1912693 | 4/2008 |
| EP | 1938856 | 7/2008 |
| EP | 2437837 | 4/2012 |
| EP | 2474335 A1 | 7/2012 |
| EP | 2510968 | 10/2012 |
| EP | 2624902 | 8/2013 |
| EP | 2708258 | 3/2014 |
| EP | 2054114 B1 | 3/2015 |
| EP | 3164185 | 5/2017 |
| EP | 3254721 | 12/2017 |
| EP | 3305354 | 4/2018 |
| GB | 2385533 | 8/2003 |
| JP | 2013-538631 | 10/2013 |
| NZ | 536545 | 12/2006 |
| NZ | 547748 | 7/2010 |
| WO | WO 94/02190 | 2/1994 |
| WO | WO 1998/034665 | 8/1998 |
| WO | WO 2000/074758 | 12/2000 |
| WO | WO 2001/062326 | 8/2001 |
| WO | WO 2003/076020 | 9/2003 |
| WO | WO 2004/071565 | 8/2004 |
| WO | WO 2007/143792 | 12/2007 |
| WO | WO 2009/065368 | 5/2009 |
| WO | WO 2012/040791 | 4/2012 |
| WO | WO 2012/055886 | 5/2012 |
| WO | WO 2013/066195 | 5/2013 |
| WO | WO 2014/141029 | 9/2014 |
| WO | WO 2014/181214 | 11/2014 |
| WO | WO 2014/183167 | 11/2014 |
| WO | WO 2015/070289 | 5/2015 |
| WO | WO 2015/092621 | 6/2015 |
| WO | WO 2015/161345 | 10/2015 |
| WO | WO 2015/193821 | 12/2015 |
| WO | WO 2016/041008 | 3/2016 |
| WO | WO 2016/041019 | 3/2016 |
| WO | WO 2016/075658 | 5/2016 |

OTHER PUBLICATIONS

Chinese Office Action for Chinese Patent Application No. 201780073731.0, dated Mar. 1, 2021 in 7 pages including English translation.

International Search Report for PCT Application No. PCT/IB2017/056136 dated Feb. 2, 2018 in 7 pages.

* cited by examiner

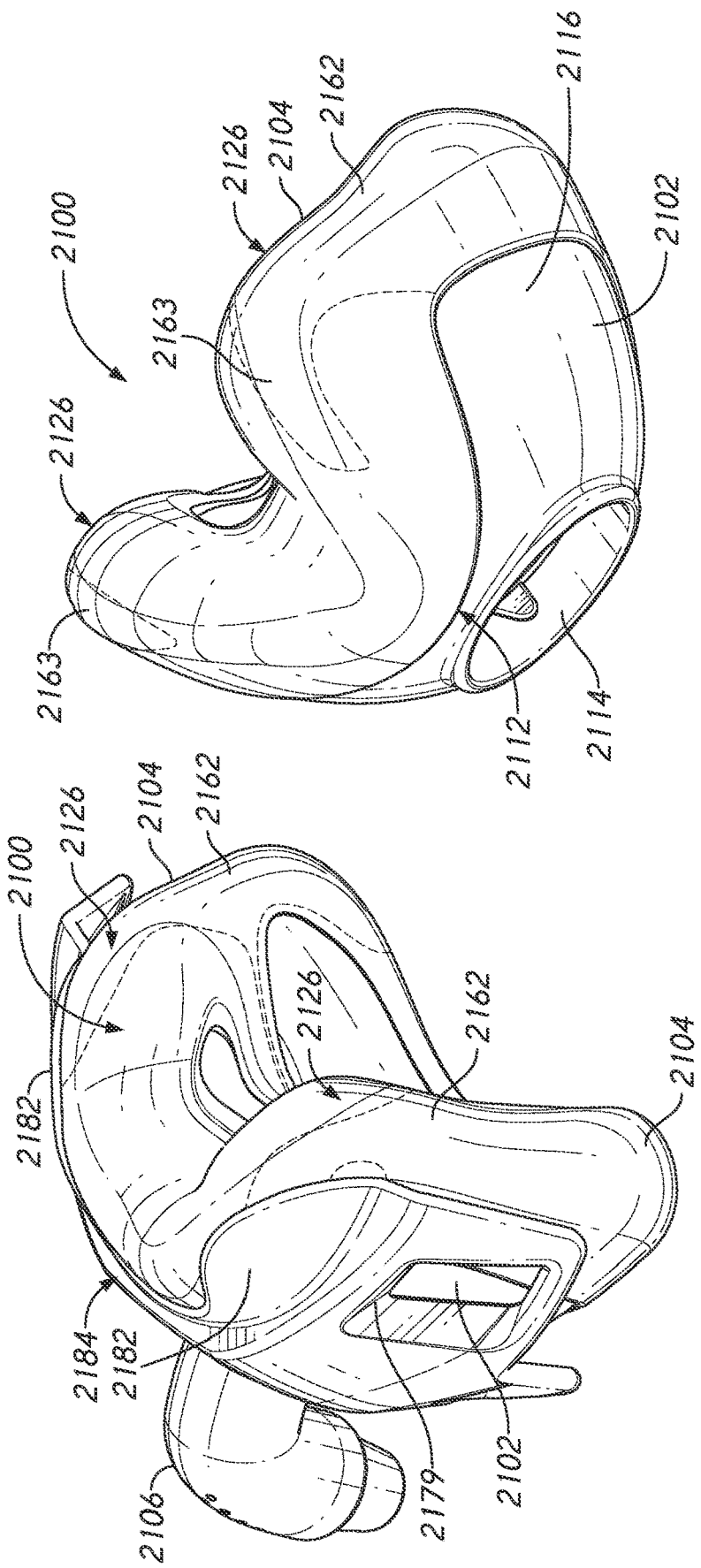

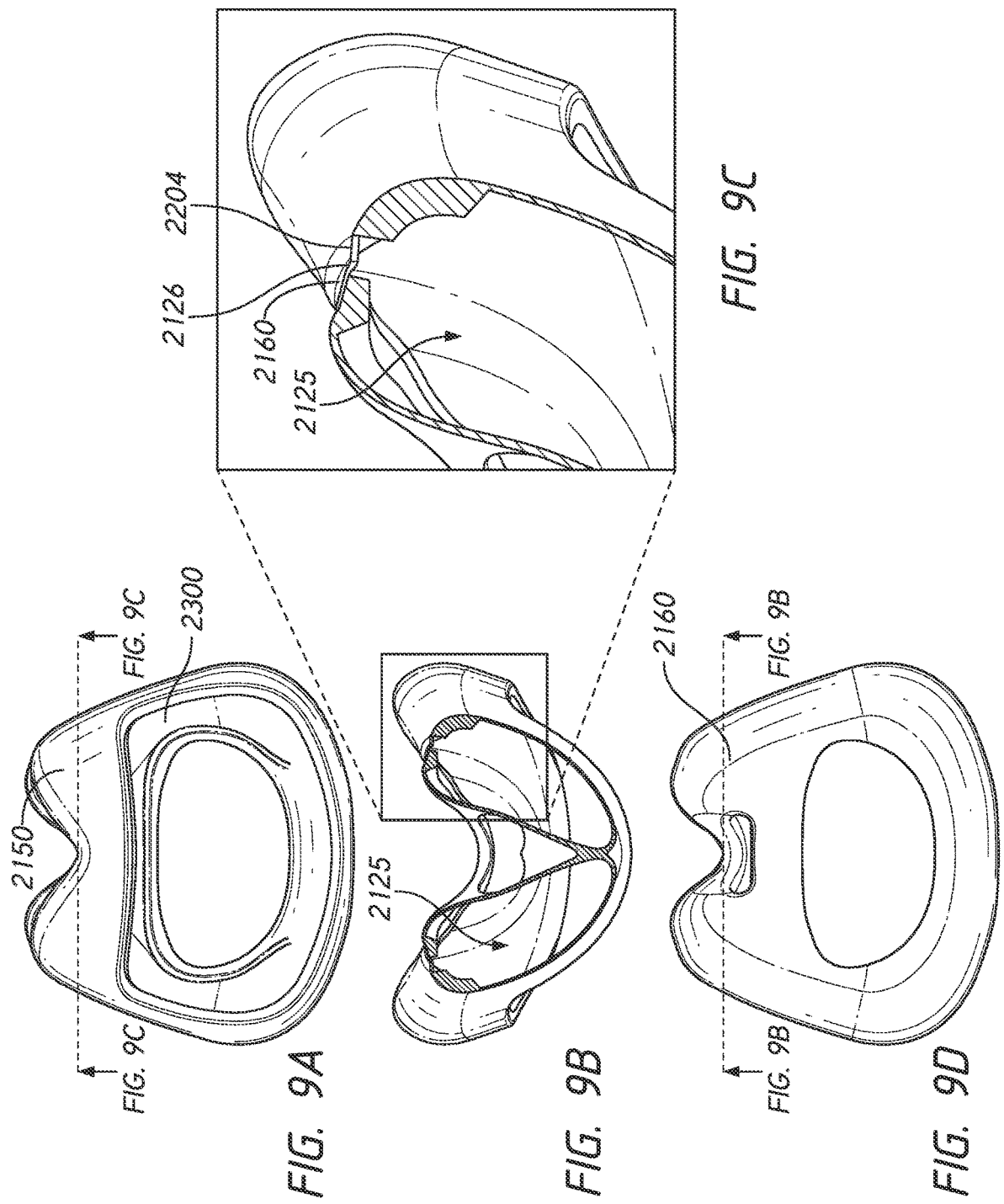

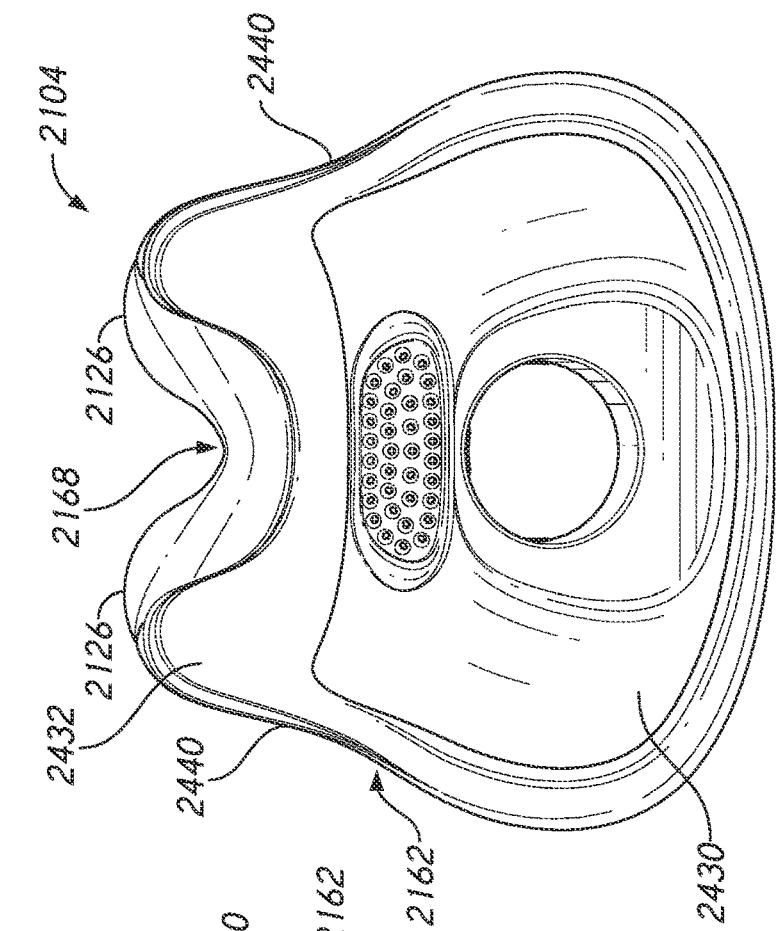
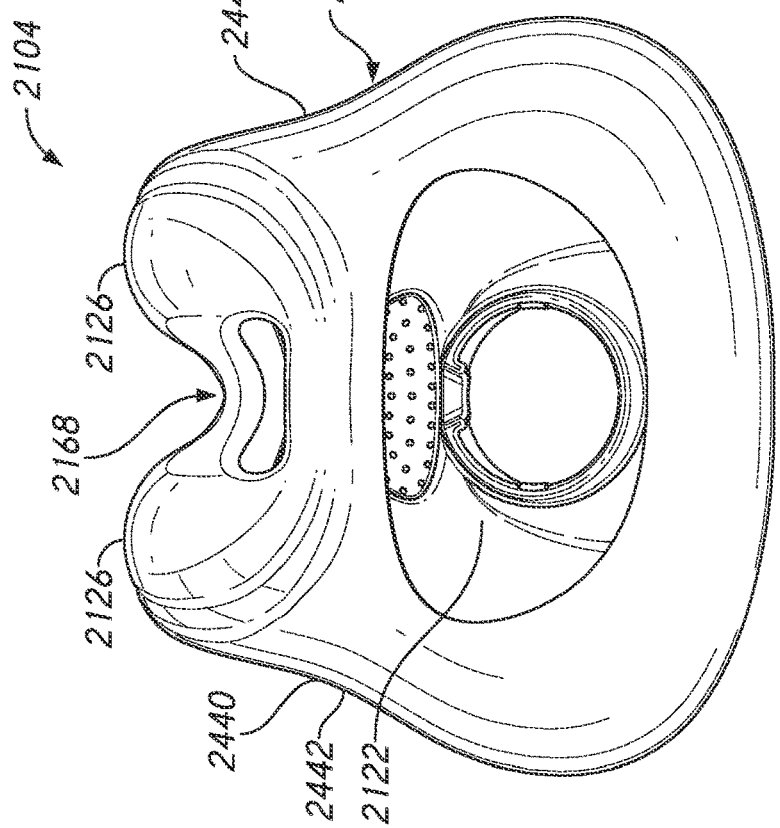

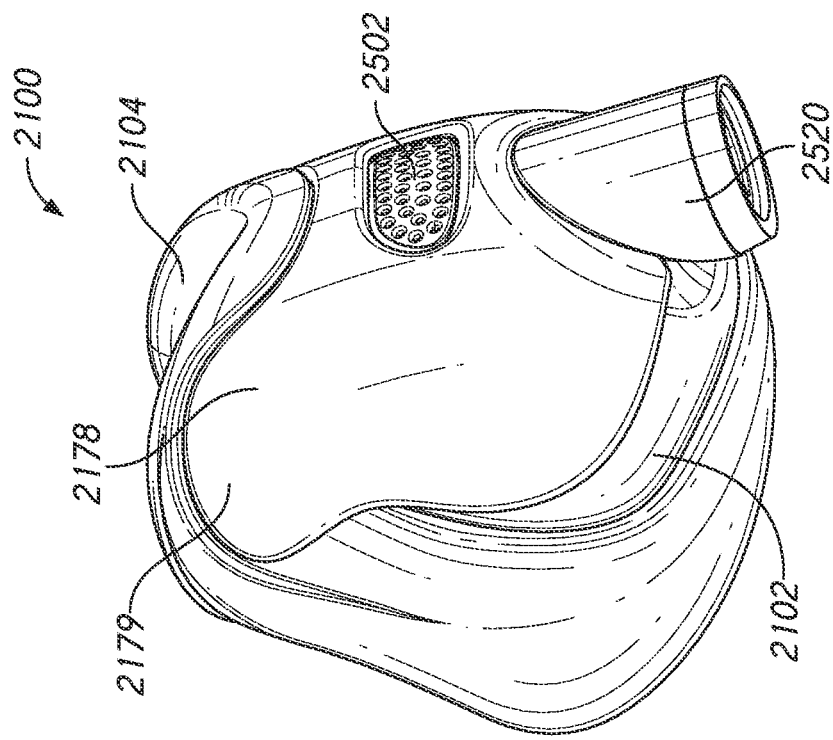
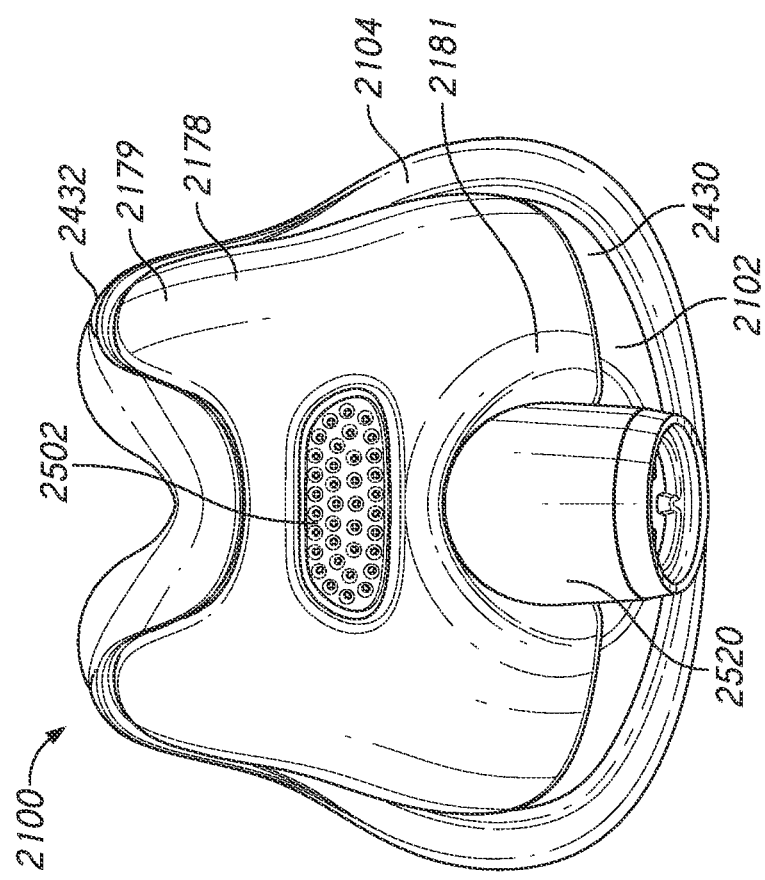
FIG. 19B
FIG. 19A

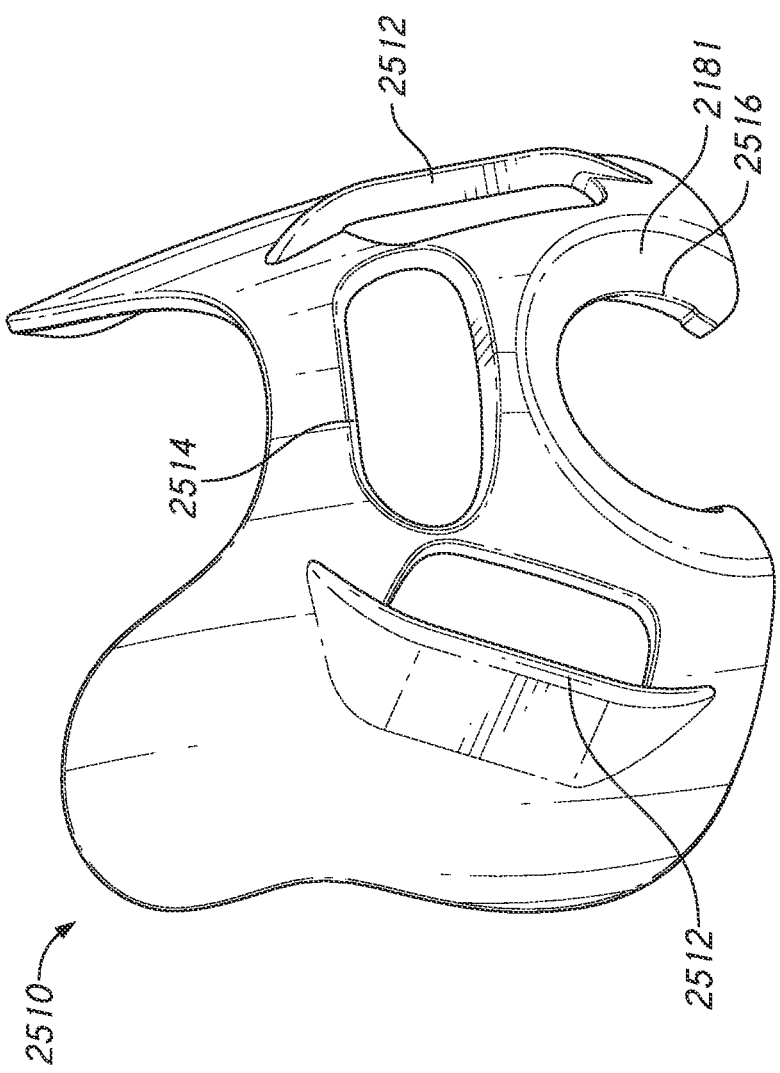

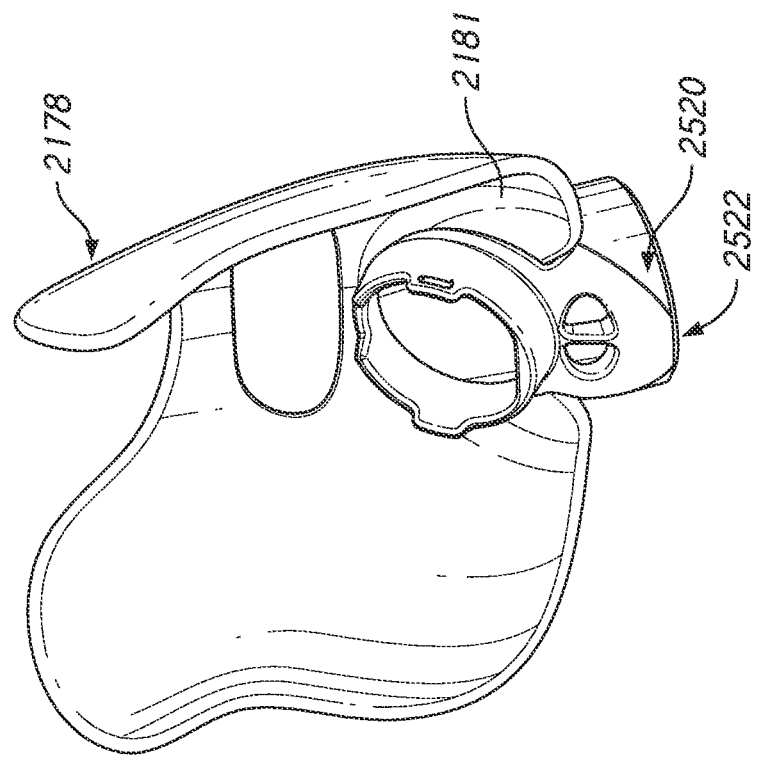
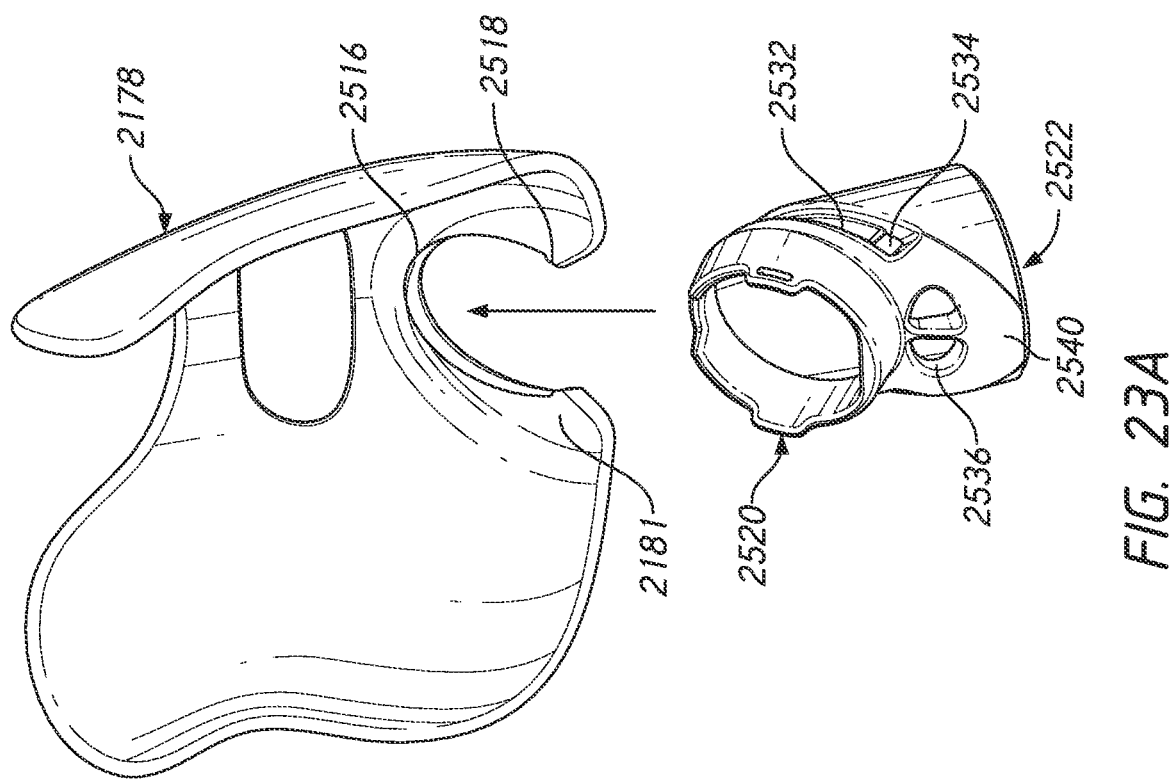
FIG. 23B
FIG. 23A

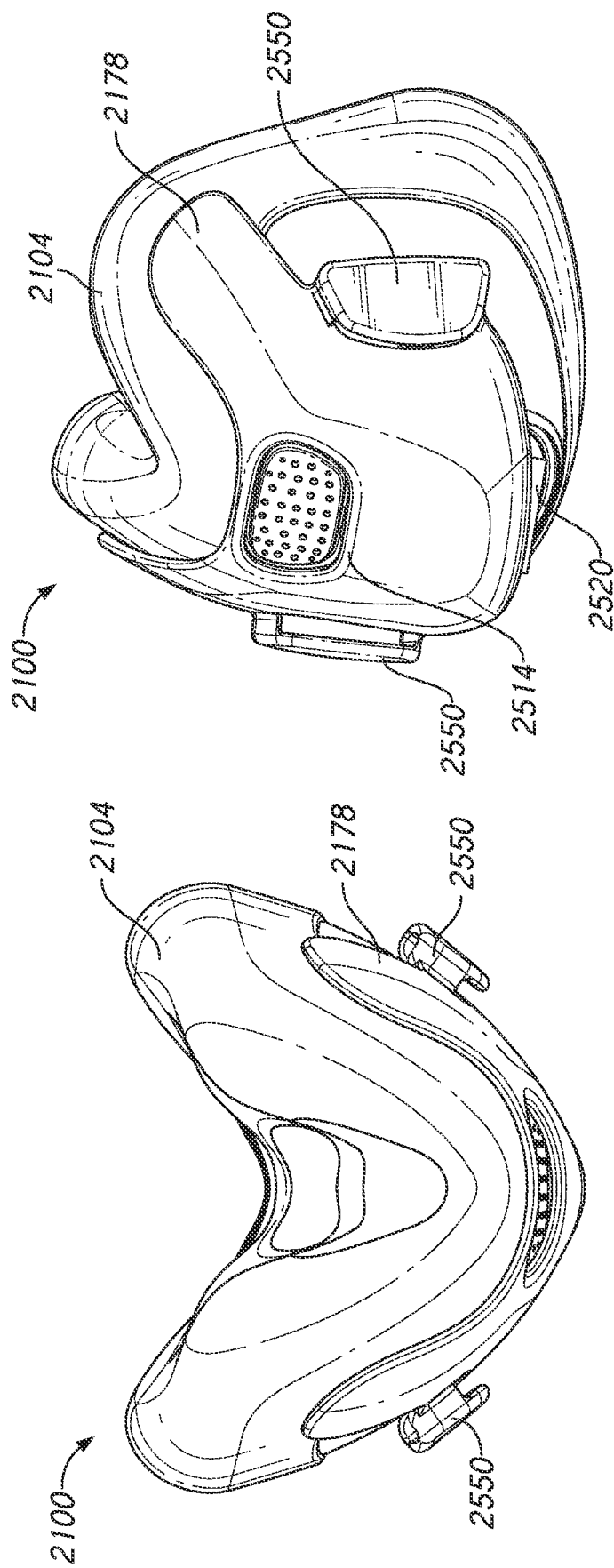

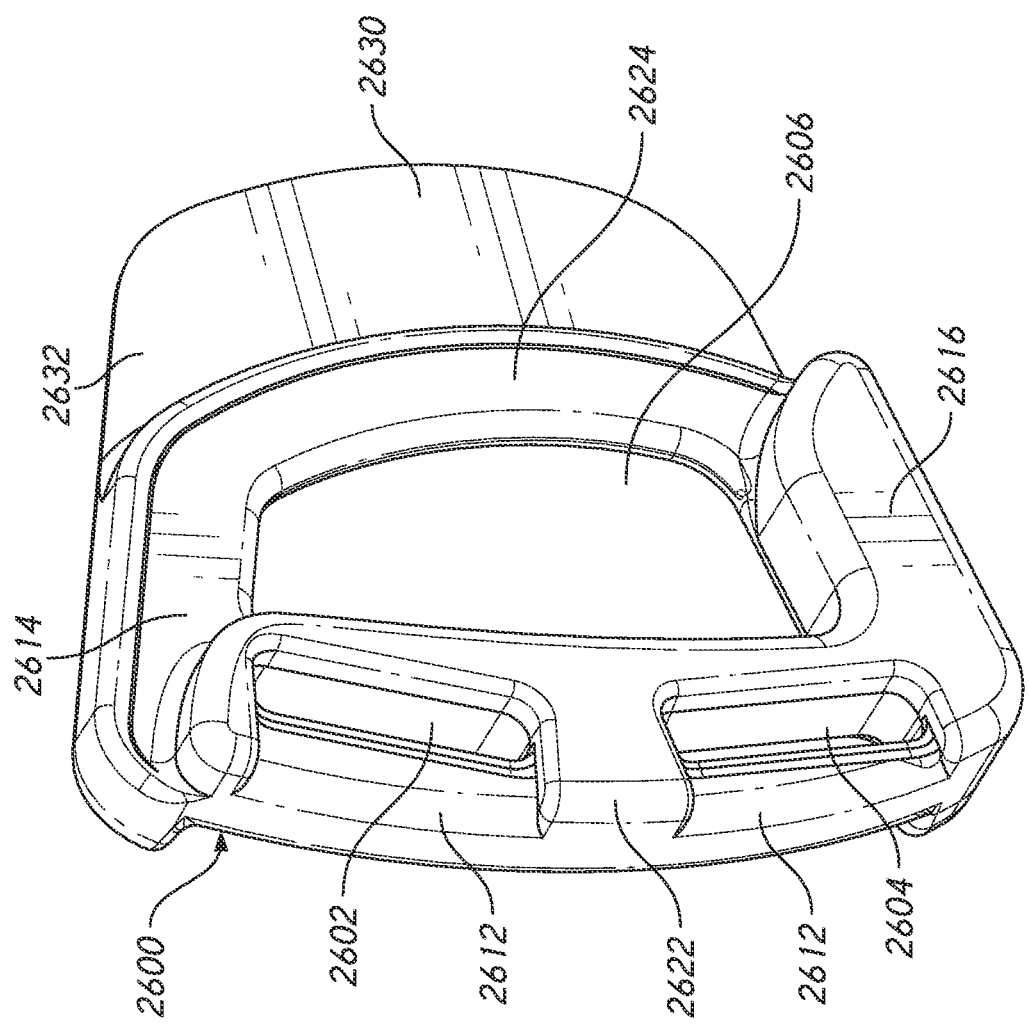

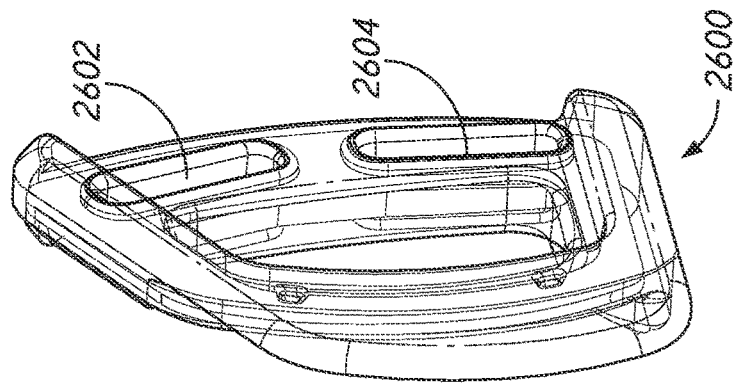
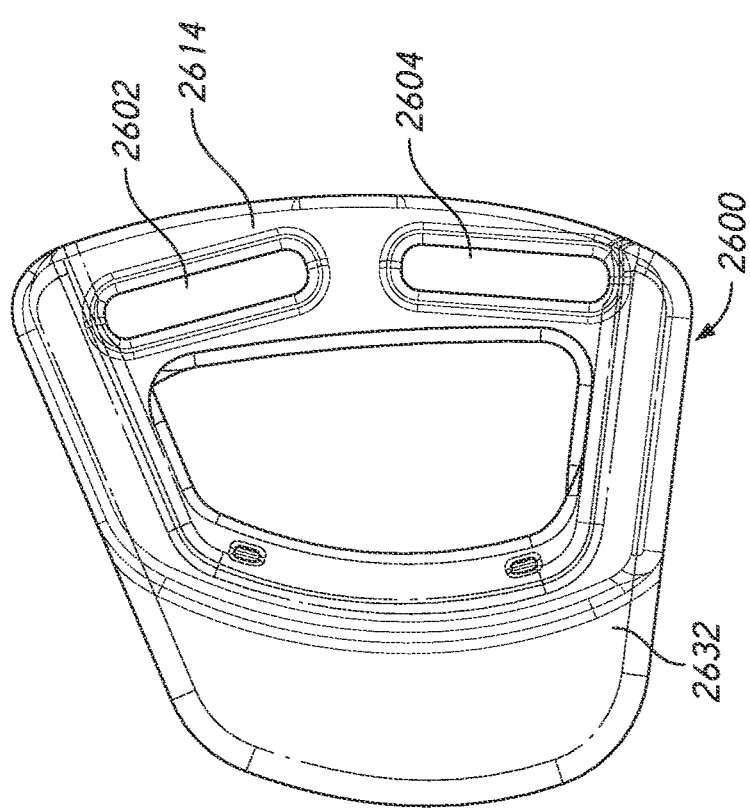
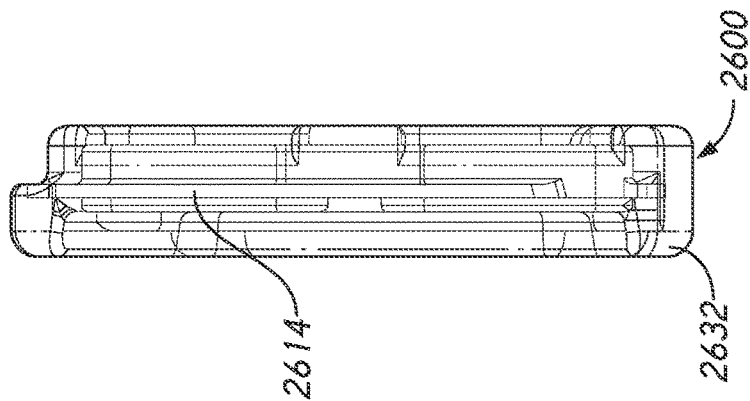
FIG. 33E
FIG. 33D
FIG. 33C

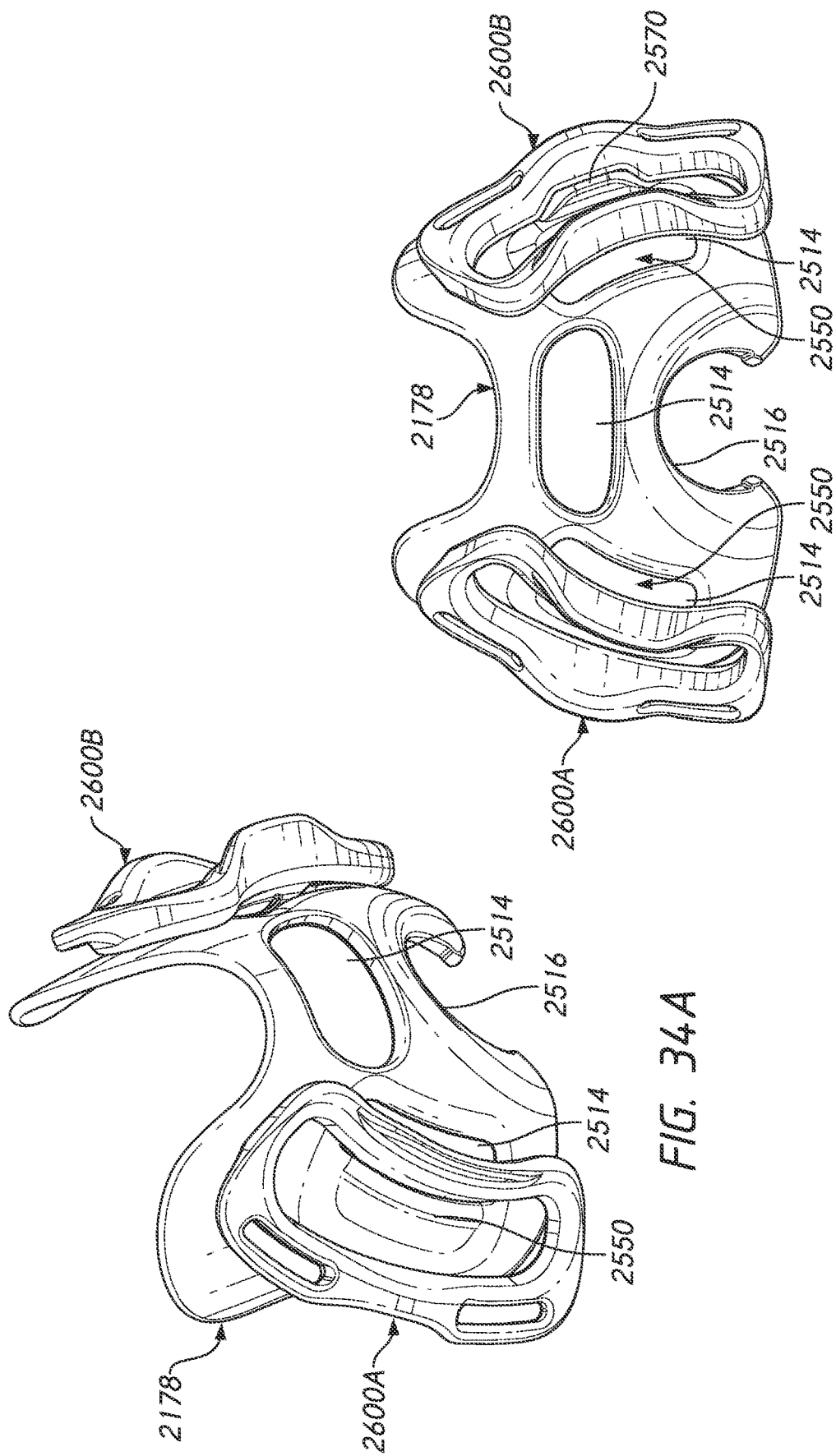

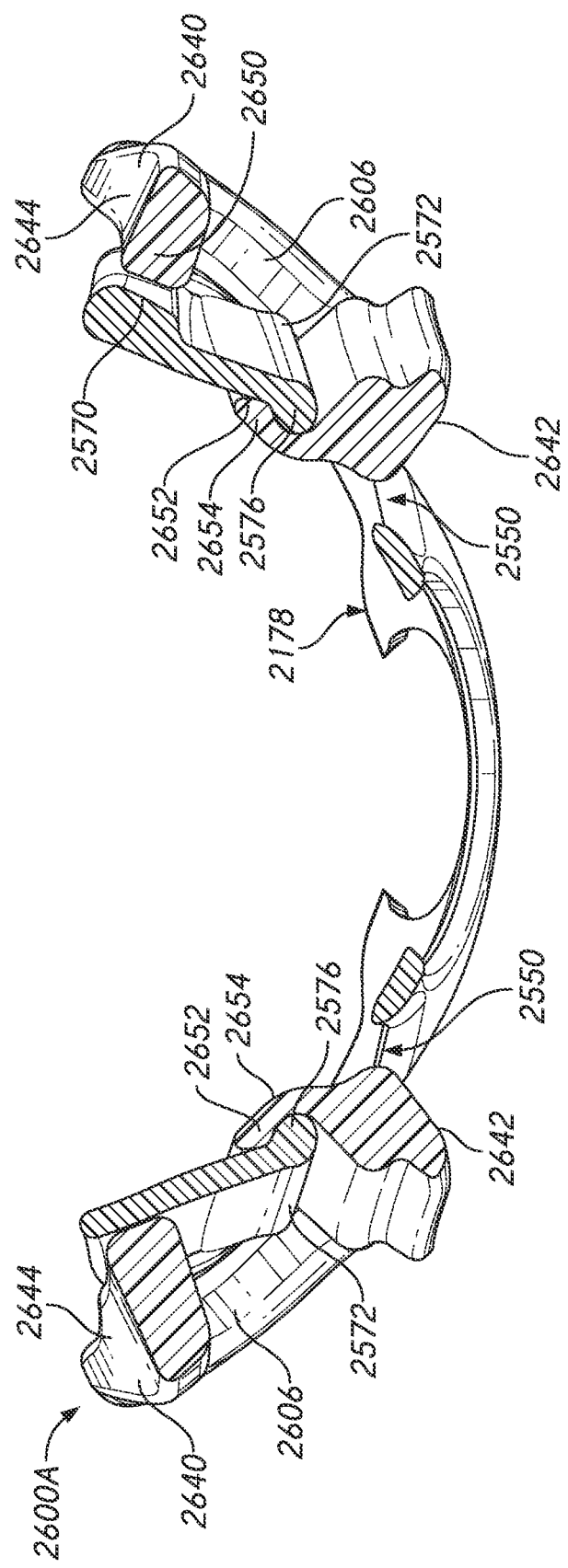

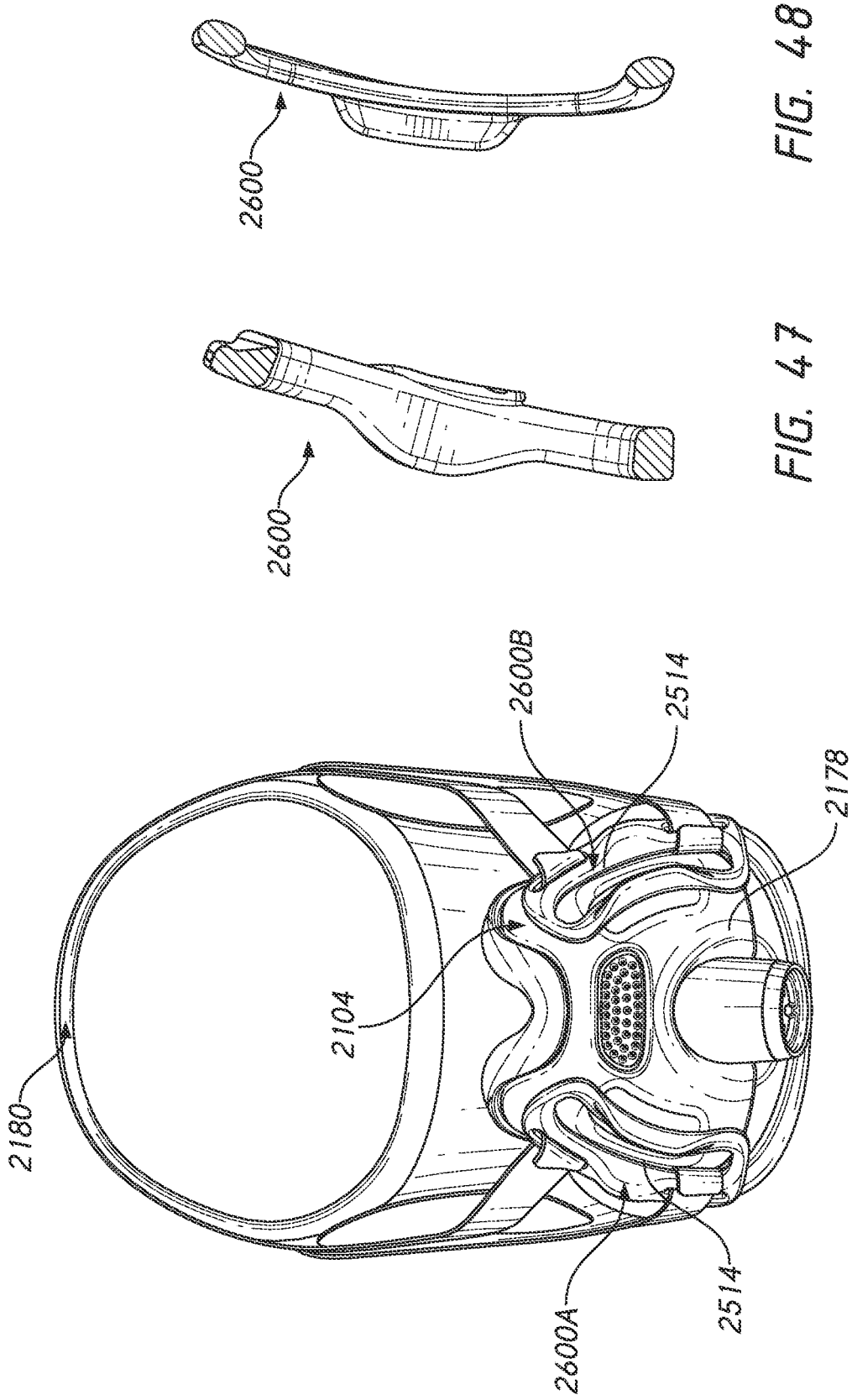

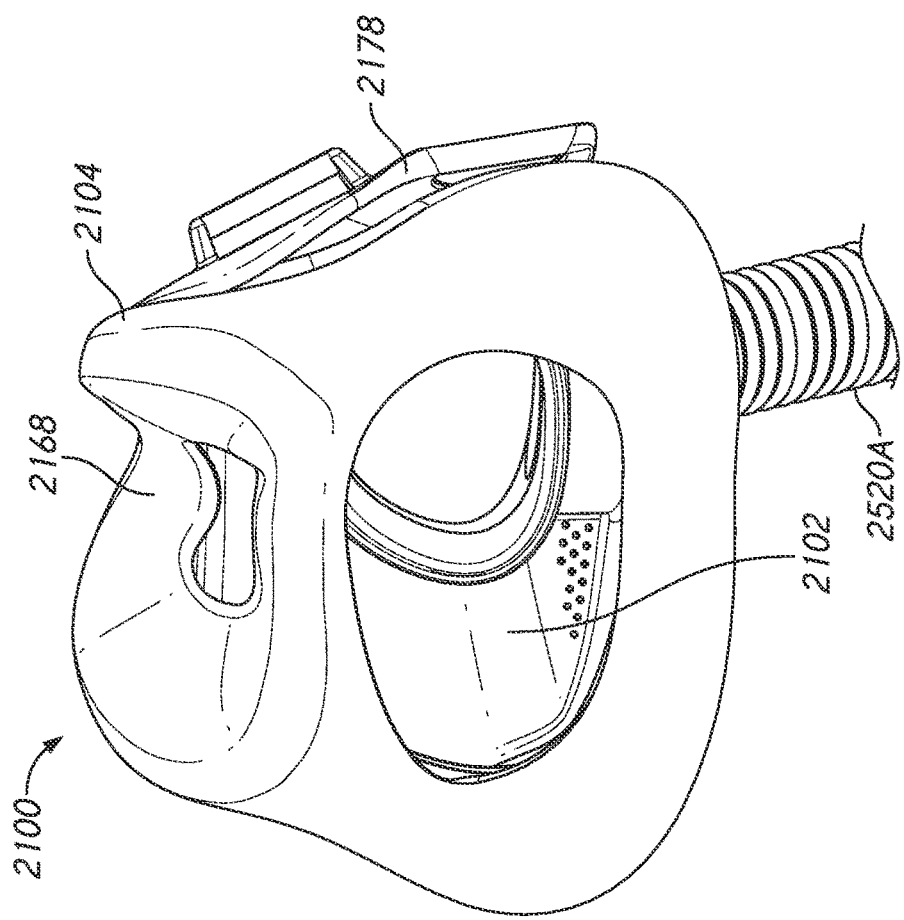
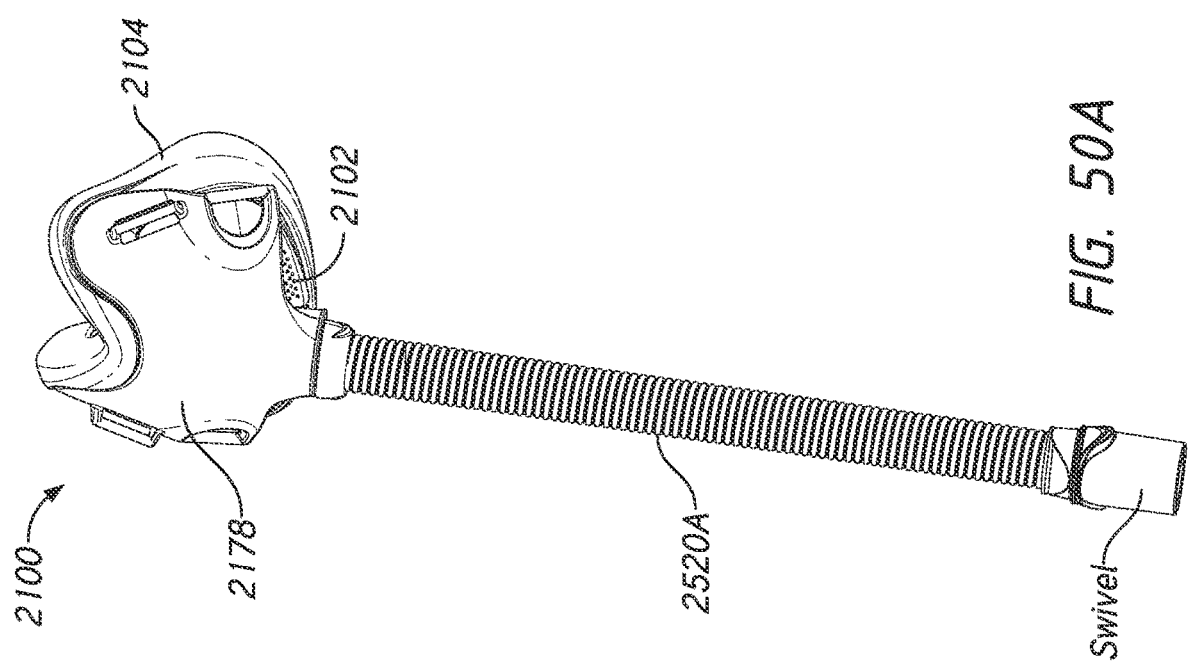
FIG. 50B
FIG. 50A

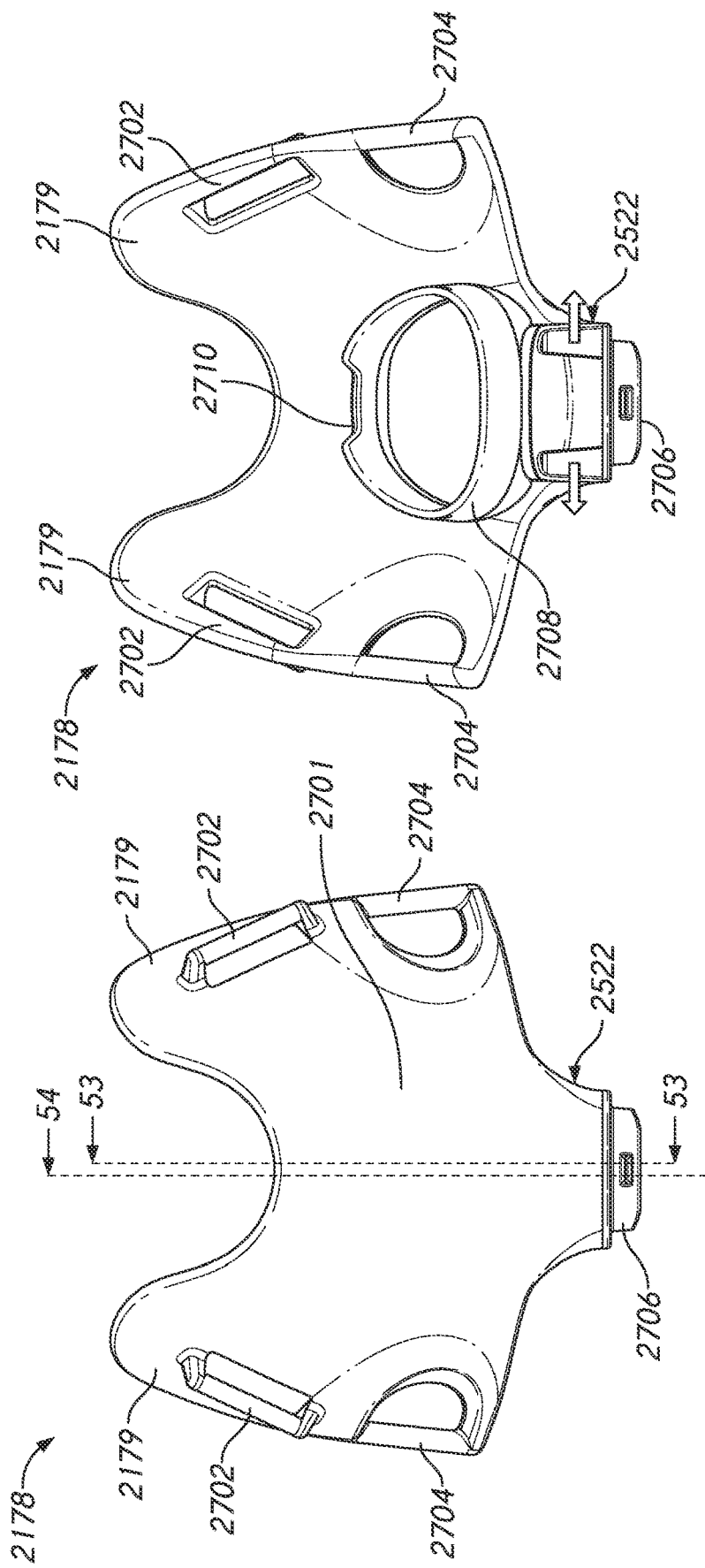

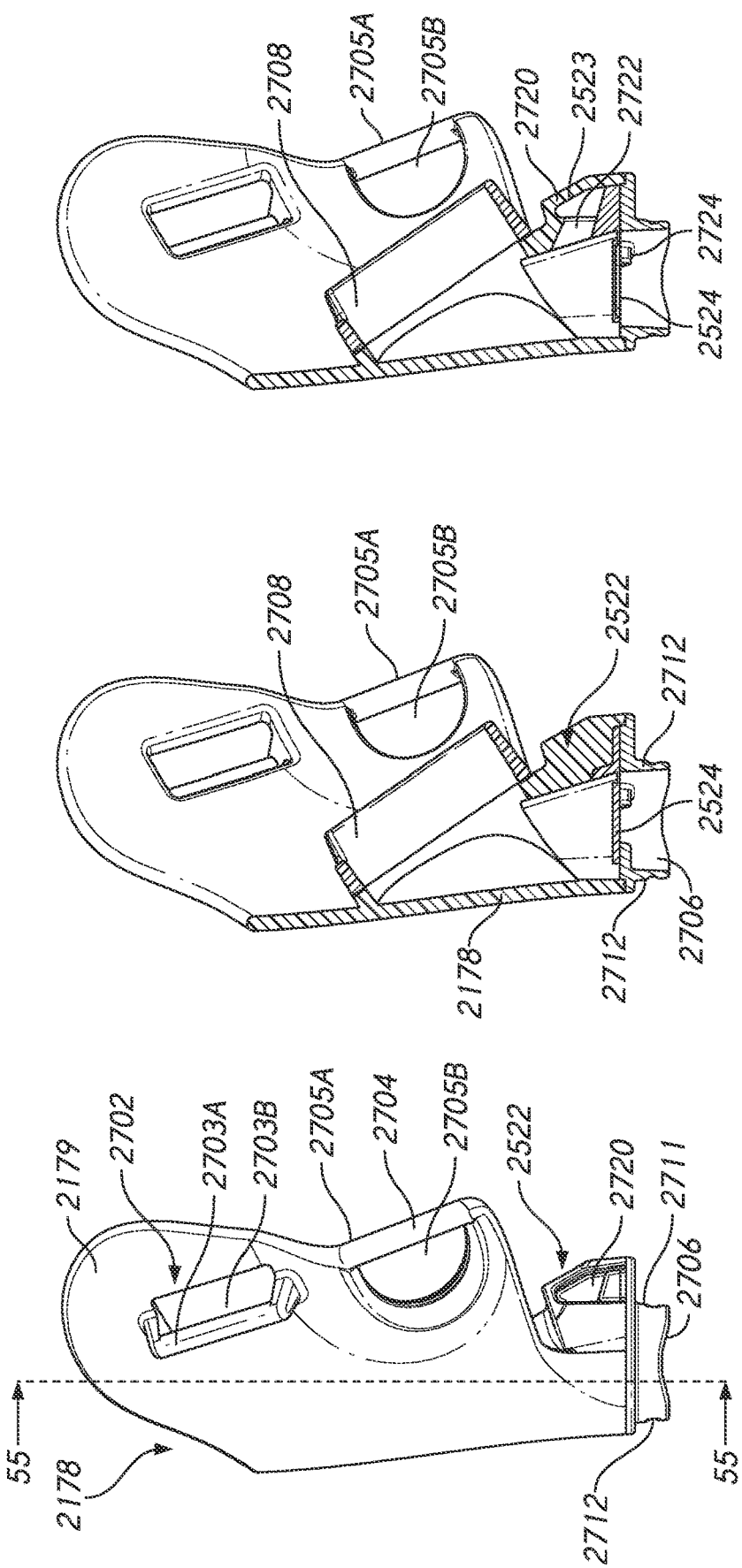

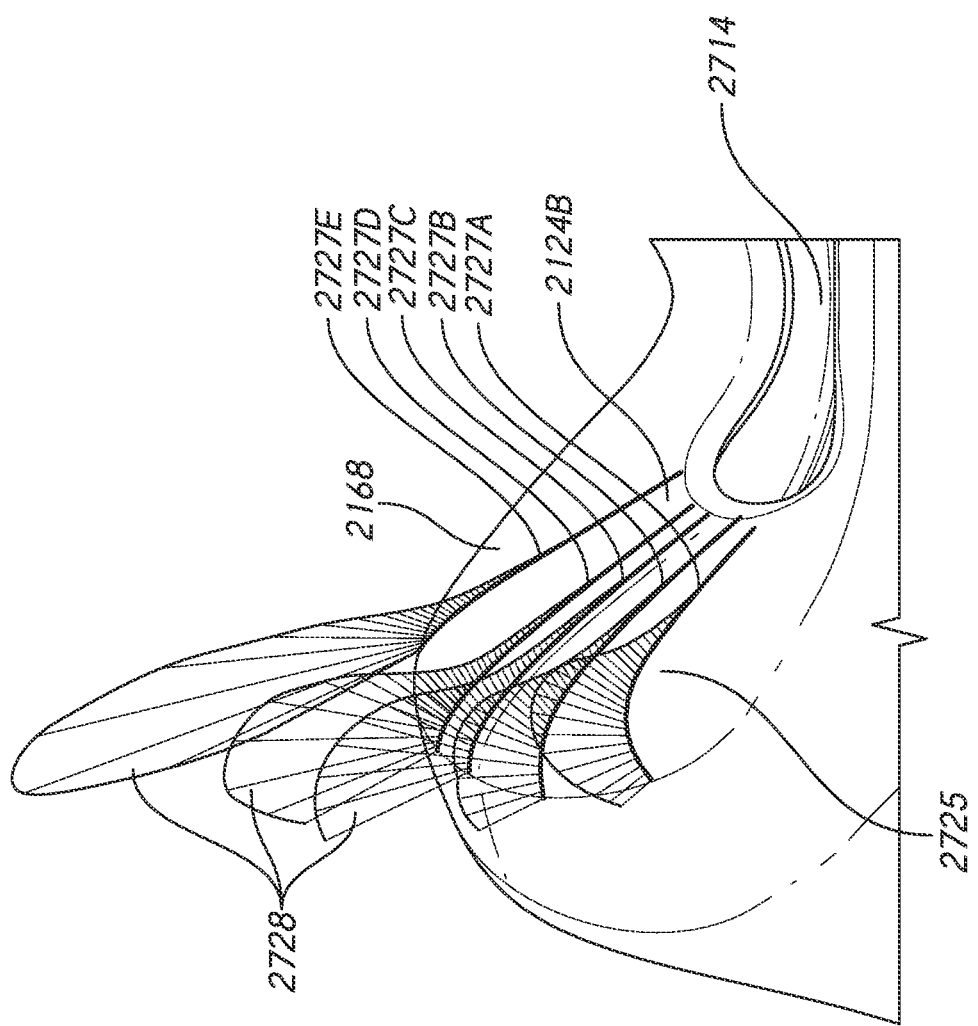

PATIENT INTERFACES

INCORPORATION BY REFERENCE TO ANY PRIORITY APPLICATIONS

This application is a National Phase Application of PCT International Application Number PCT/IB2017/056136, filed Oct. 5, 2017, which claims priority to U.S. Provisional Application No. 62/413,604, filed Oct. 27, 2016, U.S. Provisional Application No. 62/413,280, filed Oct. 26, 2017, and U.S. Provisional Application No. 62/404,341, filed Oct. 5, 2016, the entirety of each of which is incorporated by reference herein.

BACKGROUND OF THE INVENTION

Field of the Invention

The present disclosure relates to interface assemblies for respiratory therapy. In particular, the present disclosure relates to under-nose interface assemblies that do not cover the bridge of the user's nose.

Description of the Related Art

In patients suffering from obstructive sleep apnea (OSA), muscles that normally keep the upper airway open relax during slumber to the extent that the airway is constrained or completely closed off, a phenomenon often manifesting itself in the form of snoring. When this occurs for a period of time, the patient's brain typically recognizes the threat of hypoxia and partially wakes the patient in order to open the airway so that normal breathing may resume. The patient may be unaware of these waking episodes, which may occur as many as several hundred times per session of sleep. This partial awakening may significantly reduce the quality of the patient's sleep, over time potentially leading to a variety of symptoms, including excessive daytime sleepiness, chronic fatigue, elevated heart rate, elevated blood pressure, weight gain, headaches, irritability, depression and anxiety.

Obstructive sleep apnea is commonly treated with the application of positive airway pressure (PAP) therapy. PAP therapy involves delivering a flow of gas to a patient at a therapeutic pressure above atmospheric pressure that will reduce the frequency and/or duration of apneas, hypopneas, and/or flow limitations. The therapy is often implemented by using a positive airway pressure device to deliver a pressurized stream of air through a conduit to a patient through a patient interface or mask positioned on the face of the patient.

One common type of patient interface assembly used with PAP therapy or other respiratory therapies involving the administration of gas includes a seal that contacts the bridge of the nose of a user of the interface assembly. The bridge of the nose is sensitive to pressure applied by the seal of the interface assembly. More recently, interface assemblies have become available that do not contact the bridge of the nose. Such interface assemblies can be referred to as "under-nose" interface assemblies. A need exists to provide improved under-nose interface assemblies with improved comfort and/or sealing performance, or to provide the public with a useful choice.

SUMMARY OF THE INVENTION

The systems, methods and devices described herein have innovative aspects, no single one of which is indispensable or solely responsible for their desirable attributes. Without limiting the scope of the claims, some of the advantageous features will now be summarized.

In some configurations, an interface for use in providing positive pressure respiratory therapy comprises a mask assembly having a mask seal. The mask assembly is configured to be fully positioned lower than a bridge of a nose of a face of a user and to provide an exposed bridge of the nose of the user. The mask seal comprises a nasal region comprising at least one nasal opening. The mask seal comprises a first paddle on a first side of the nasal region and a second paddle on a second side of the nasal region. The first paddle is configured to contact one side of the nose of the user and the second paddle is configured to contact the other side of the nose of the user. The first paddle comprises a first cutout region extending from a front side of the first paddle to a rear side of the first paddle. The second paddle comprises a second cutout region extending from a front side of the second paddle to a rear side of the second paddle.

In some configurations, the mask seal further comprises a support structure configured to support the nasal region of the mask seal.

In some configurations, the mask seal comprises a recessed front surface including an upper recessed front surface configured to receive a frame paddle.

In some configurations, the first cutout region comprises a reduced wall thickness.

In some configurations, the first cutout region comprises a first concave portion positioned along a length of the first cutout region and the second cutout region comprises a second concave portion positioned along a length of the second cutout region.

In some configurations, the first concave portion is configured to allow the first cutout region to fold inwardly when a force is applied to the first paddle and the second concave portion is configured to allow the second cutout region to fold inwardly when a force is applied to the second paddle.

In some configurations, the mask seal comprises a concave region positioned along an outer peripheral side of the mask seal.

In some configurations, the first cutout region comprises a first inner region and a first outer region. The first inner region is configured to compress towards the first outer region when a force is applied to the first inner region. The second cutout region comprises a second inner region and a second outer region. The second inner region is configured to compress towards the second outer region when a force is applied to the second outer region.

In some configurations, the first cutout region extends across a portion of the rear side of the first paddle at least to a first side of the nasal opening.

In some configurations, an interface for use in providing positive pressure respiratory therapy comprises a mask assembly having a mask seal. The mask assembly is configured to be fully positioned lower than a bridge of a nose of a face of a user and to provide an exposed bridge of the nose of the user. The mask seal comprises a nasal region comprising at least one nasal opening. The mask seal comprises a first paddle on a first side of the nasal region and a second paddle on a second side of the nasal region. The first paddle is configured to contact one side of the nose of the user and the second paddle is configured to contact the other side of the nose of the user. The mask assembly further comprises an upper front portion. The upper front portion comprises a front recessed portion. In some configurations, the mask assembly further comprises a stepped transition between an upper periphery of the upper front portion and the front recessed portion.

In some configurations, the stepped transition follows the curvature of a periphery of the first paddle and the second paddle.

In some configurations, the stepped transition varies in depth.

In some configurations, the stepped transition is tapered such that the depth is smallest at a lower extreme of the stepped transition.

In some configurations, a depth of the stepped transition is dependent on a size of the mask seal.

In some configurations, the mask assembly further comprises a frame. The front recessed portion is configured to receive at least a portion of the frame.

In some configurations, the stepped transition has a maximum depth that is greater than or equal to a thickness of the frame.

In some configurations, the upper front portion further comprises a first upper corner and a second upper corner formed on a front side of the first and second paddles.

In some configurations, the stepped transition includes a depth that varies such that the depth of the stepped transition is greater at the first upper corner and second upper corner than at a mid-portion between the first upper corner and second upper corner.

In some configurations, the interface includes a frame removably connectable to the mask assembly.

In some configurations, the frame comprising frame paddles.

In some configurations, the frame paddles are positioned inset and/or within the front recessed surface, when assembled to the mask assembly.

In some configurations, an outer surface of the frame paddles sits flush with the upper recessed surface.

In some configurations, the frame provides additional support to the nasal region of the seal.

In some configurations, the frame provides additional rigidity to the front side nasal region of the seal.

In some configurations, the frame paddles provide support to the nasal region.

In some configurations, the frame paddles help to prevent the seal paddles from deflecting away from the user's nose in use.

In some configurations, the frame paddles can help to prevent the frame paddles from contacting or digging into the user's face if the mask seal becomes overly deformed.

In some configurations, the recessed front surface allows the use of a single-sized frame to be implemented with mask assemblies having varying sizes.

According to some embodiments, an interface for use in providing positive pressure respiratory therapy can include a mask assembly and a frame. The mask assembly can include a mask seal. The mask assembly can be fully positioned lower than a bridge of a nose of a face of a user and provide an exposed bridge of the nose of the user. The mask seal can include a nasal region. The nasal region can include at least one nasal opening. The mask seal can include a first paddle on a first side of the nasal region and a second paddle on a second side of the nasal region. The first paddle can contact one side of the nose of the user and the second paddle can contact the other side of the nose of the user. The frame can be removably coupled to the mask assembly. The mask assembly can include a housing. The housing can include an inlet and a concave front surface surrounding the inlet. The inlet can define a flow path to an interior chamber of the mask assembly.

In some configurations, the interface includes an elbow connected to the frame by a connection feature.

In some configurations, the connection feature includes a snap-fit arrangement such that the frame can snap into a slot of the elbow.

In some configurations, the connection feature includes a snap-fit arrangement such that the elbow includes a plurality of ribs extending outwardly from the elbow. The plurality of ribs can form a slot to receive the frame.

In some configurations, the frame is shaped to at least partially receive the elbow.

In some configurations, the elbow comprises a valve port configured to provide a flow path from the atmosphere to an interior space of the elbow.

In some configurations, the valve port faces the concave front surface and the valve port and concave front surface define a flow path such that an area of the valve port forms a smallest area of the flow path.

In some configurations, the mask assembly can include a bias vent configured to exhaust air exhaled by the user.

In some configurations, an interface for use in providing positive pressure respiratory therapy comprises a mask assembly having a mask seal. The mask assembly is configured to be fully positioned lower than a bridge of a nose of a face of a user and to provide an exposed bridge of the nose of the user. The mask seal comprises a nasal region comprising at least one nasal opening. The mask seal comprises a first paddle on a first side of the nasal region and a second paddle on a second side of the nasal region. The first paddle is configured to contact one side of the nose of the user and the second paddle is configured to contact the other side of the nose of the user. The mask assembly further comprises a frame removably coupled to the mask assembly, wherein the frame includes a clip retention feature configured to connect to a headgear clip. The headgear clip includes: an upper strap slot; a lower strap slot; a pull tab; and an aperture positioned between lateral sides of the upper and lower strap slots and the pull tab.

In some configurations, the clip retention feature provides an opening configured to exhaust air exhaled by the user.

In some configurations, the headgear clip includes an insert such that the pull tab forms at least a part of an over-moulded arrangement.

In some configurations, the frame includes a keying bump configured to engage a corresponding keying notch of the headgear clip.

In some configurations, the keying bump is positioned on one side of a first clip retention feature and the keying bump is configured to indicate a proper orientation to connect the headgear clip.

In some configurations, the frame includes at least two openings.

In some configurations, the headgear clip includes a finger grip and a thumb grip, the finger grip and the thumb grip forming an over-moulded grip provided to the user, wherein the finger grip is positioned laterally opposite the thumb grip along an outer concave surface of the headgear clip.

In some configurations, the headgear clip is positioned adjacent an upper front portion of the mask seal such that the headgear clip prevents ballooning of the mask seal.

According to some embodiments, a respiratory mask can include a mask assembly and a frame. The mask assembly can include a seal and a housing. The seal can include a nasal sealing portion and an oral sealing portion. The seal can provide a flow of gasses to a user's nose and mouth. The housing and the seal can form a breathing chamber. The frame can be removably coupled to the mask assembly. The frame can include a main body, an inlet opening through which a supply of pressurized air is provided to the mask assembly and an anti-asphyxia valve in fluid communication with the inlet opening. The main body of the frame can define at least a portion of a gas flow passage of the anti-asphyxia valve.

In some configurations, the frame includes a tube connector coupled to a main body of the frame. The frame can connect to a breathing tube. The tube connector can define the inlet opening.

In some configurations, the tube connector can secure a valve member of the anti-asphyxia valve to the main body of the frame.

In some configurations, the frame can define a mask connector. The mask connector can secure the mask assembly to the frame. The mask connector can define a portion of the gas flow passage. The mask connector can receive a flow of gas from the inlet opening and anti-asphyxia valve. The mask connector can deliver the flow of gas to the mask assembly.

In some configurations, a front wall of the frame can define a portion of the gas flow passage of the respiratory mask.

In some configurations, the housing can define a recess that accommodates at least a portion of the frame comprising the anti-asphyxia valve.

In some configurations, the nasal sealing portion can include a left nasal sealing surface and a right nasal sealing surface. An inner portion of each sealing surface nearest a nasal opening of the seal can be generally flat.

In some configurations, an outer portion of each of the sealing surfaces can be curved. A radius of curvature of the outer portions can decrease in a rearward to forward direction within each of the outer portions.

In some configurations, an angle defined between the left and right sealing surfaces can increase in a rearward to forward direction.

In some configurations, the mask includes an inlet tube that defines a portion of the gas flow passage and is fixed relative to the main body of the frame.

In some configurations, the inlet opening is integrally formed with the main body of the frame.

In some configurations, the inlet tube extends downwardly from a bottom region of the front wall.

In some configurations, the inlet tube includes a front surface that defines a continuous surface with a front surface of the front wall.

In some configurations, the inlet tube is positioned at least partially rearward of the front wall.

In some configurations, the inlet tube includes a rear internal surface and a front internal surface. The rear internal surface can extend away from the inlet and can be angled toward the front internal surface.

In some configurations, the recess accommodates the inlet tube.

In some configurations, the housing includes a bias vent that is positioned on opposing sides of an inlet aperture and on a front surface of the housing below the frame. The bias vent can exhaust air below a lower edge of the frame.

According to some embodiments, a respiratory mask can include a mask assembly and a frame. The mask assembly can include a full-face mask seal and a housing. The housing can include a bias vent. The frame can connect the mask assembly to a supply of pressurized air and can include a main body defining at least one headgear connector. The bias vent can be positioned on opposing sides of an inlet aperture and on a front surface of the housing below the frame and the bias vent can exhaust air below a lower edge of the frame. The frame can define at least a portion of a gas flow passage of the anti-asphyxia valve.

In some configurations, the frame can define at least one valve outlet of the anti-asphyxia valve.

In some configurations, the frame includes a tube connector coupled to a main body of the frame. The frame can connect to a breathing tube. The tube connector can define an inlet opening.

In some configurations, the tube connector can secure a valve member of the anti-asphyxia valve to the main body of the frame.

In some configurations, the frame can define a mask connector. The mask connector can secure the mask assembly to the frame. The mask connector can define a portion of the gas flow passage. The mask connector can receive a flow of gas from the inlet opening and anti-asphyxia valve. The mask connector can deliver the flow of gas to the mask assembly.

In some configurations, a front wall of the frame can define a portion of the gas flow passage of the respiratory mask.

In some configurations, the housing can define a recess that accommodates at least a portion of the frame comprising the anti-asphyxia valve.

In some configurations, the nasal sealing portion can include a left nasal sealing surface and a right nasal sealing surface. An inner portion of each sealing surface nearest a nasal opening of the seal can be generally flat.

In some configurations, an outer portion of each of the sealing surfaces can be curved. A radius of curvature of the outer portions can decrease in a rearward to forward direction within each of the outer portions.

In some configurations, an angle defined between the left and right sealing surfaces can increase in a rearward to forward direction.

In some configurations, the mask includes an inlet tube that defines a portion of the gas flow passage and is fixed relative to the main body of the frame.

In some configurations, the inlet opening is integrally formed with the main body of the frame.

In some configurations, the inlet tube extends downwardly from a bottom region of the front wall.

In some configurations, the inlet tube includes a front surface that defines a continuous surface with a front surface of the front wall.

In some configurations, the inlet tube is positioned at least partially rearward of the front wall.

In some configurations, the inlet tube includes a rear internal surface and a front internal surface. The rear internal surface can extend away from the inlet and can be angled toward the front internal surface.

In some configurations, the recess accommodates the inlet tube.

In some configurations, the housing includes a bias vent that is positioned on opposing sides of an inlet aperture and on a front surface of the housing below the frame. The bias vent can exhaust air below a lower edge of the frame.

According to some embodiments, a respiratory mask can include a mask assembly, and a frame. The mask assembly can include a seal and a housing. The frame can be removably coupled to the mask assembly. The frame can include an inlet opening through which a supply of pressurized air is provided to the mask assembly and an anti-asphyxia valve in fluid communication with the inlet opening. The housing can include a valve recess that accommodates at least a portion of the frame comprising the anti-asphyxia valve.

In some configurations, the valve recess defines a concave region.

In some configurations, the concave region is positioned below the inlet.

In some configurations, the concave region is positioned adjacent the inlet.

In some configurations, the valve recess has a width that is less than a maximum width of the inlet.

In some configurations, the valve recess can receive at least a portion of the valve.

In some configurations, the valve recess can receive at least a rear portion of the valve.

In some configurations, the valve recess can receive at least a portion of one or more valve outlets of the valve.

In some configurations, the valve recess has a curved surface that corresponds to a curvature of a rear surface of the valve.

In some configurations, the valve recess is configured to allow the valve to be positioned recessed into the seal.

In some configurations, the valve recess and the valve are configured to reduce an overall depth of the mask assembly and reduce an obtrusiveness of the mask assembly to a user.

In some configurations, the valve recess and the valve are configured to allow the valve to be positioned higher relative to a bottom edge of the seal.

In some configurations, the valve recess and the valve are configured to reduce a length of an inlet aperture.

BRIEF DESCRIPTION OF THE DRAWINGS

Throughout the drawings, reference numbers can be reused to indicate general correspondence between reference elements. The drawings are provided to illustrate example embodiments described herein and are not intended to limit the scope of the disclosure.

FIG. 3 is rear perspective view of an interface portion of the interface assembly of FIG. 1 separated from the user and without headgear.

FIG. 4 is a front perspective view of a mask assembly of the interface assembly of FIG. 1.

FIG. 9A is a front view of a mask assembly illustrating a cut-out region of a mask seal.

FIG. 9B is a sectional view of the mask assembly taken along line A-A of FIG. 9A illustrating the cut-out region of the mask seal.

FIG. 9C is a close-up view of the mask assembly of FIG. 9A illustrating the cut-out region of FIG. 9B.

FIG. 9D is a rear view of the mask assembly of FIG. 9A illustrating the cut-out region of the mask seal.

FIG. 18A is a rear view of the mask assembly of FIG. 16 illustrating the recessed surface of the mask assembly.

FIG. 18B is a front view of the mask assembly of FIG. 16 illustrating the recessed surface of the mask assembly.

FIG. 19A is a front view of a mask assembly illustrating recessed surfaces of the mask assembly.

FIG. 19B is a front and side perspective view of the mask assembly of FIG. 19A illustrating recessed surfaces of the mask assembly.

FIG. 20 is a front and side perspective view of a frame of the mask assembly of FIG. 19A.

FIG. 23A is a rear and side perspective view of a mask assembly illustrating an assembly of a mask frame.

FIG. 23B is a rear and side perspective view of the mask assembly of FIG. 23A illustrating an assembly of the mask frame.

FIG. 31A is a top view of the mask assembly of FIG. 29 illustrating clip retention features.

FIG. 31B is a front and side perspective view of the mask assembly of FIG. 29 illustrating clip retention features.

FIG. 33B is a rear and side perspective view of a headgear clip of the mask assembly of FIG. 29.

FIG. 33C is a side view of a headgear clip of the mask assembly of FIG. 29 with a portion of the clip made transparent to reveal underlying structure.

FIG. 33D is a front view of a headgear clip of the mask assembly of FIG. 29 with a portion of the clip made transparent to reveal underlying structure.

FIG. 33E is a side and rear perspective view of a headgear clip of the mask assembly of FIG. 29 with a portion of the clip made transparent to reveal underlying structure.

FIG. 34A is a front and side perspective view of a frame assembly of a mask assembly.

FIG. 34B is a front view of a frame assembly of the mask assembly of FIG. 34A.

FIG. 40 is a top cross-sectional view of a frame assembly of the mask assembly of FIG. 34A.

FIG. 46 is a front view of the interface assembly of FIG. 44 illustrating clip retention features and vent features.

FIG. 47 is a cross-sectional view of a headgear clip of the interface assembly of FIG. 44.

FIG. 48 is a cross-sectional view of a headgear clip of the interface assembly of FIG. 44.

FIG. 50A is a front, top, and side perspective view of a mask assembly including an air supply conduit.

FIG. 50B is a rear, top, and side perspective close-up view of the mask assembly of FIG. 50A.

FIG. 51A is a front view of a frame of the mask assembly of FIG. 50A.

FIG. 51B is a rear view of the frame of the mask assembly of FIG. 50A.

FIG. 52 is a side view of the frame of the mask assembly of FIG. 50A.

FIG. 53 is a side cross-sectional view of the frame of the mask assembly of FIG. 50A taken along the line 53-53 of FIG. 51A.

FIG. 54 is a side cross-sectional view of the frame of the mask assembly of FIG. 50A taken along the line 54-54 of FIG. 51A.

FIG. 65 is a close-up rear view of a portion of the mask seal of the mask assembly of FIG. 50A.

DETAILED DESCRIPTION

Figure 1:
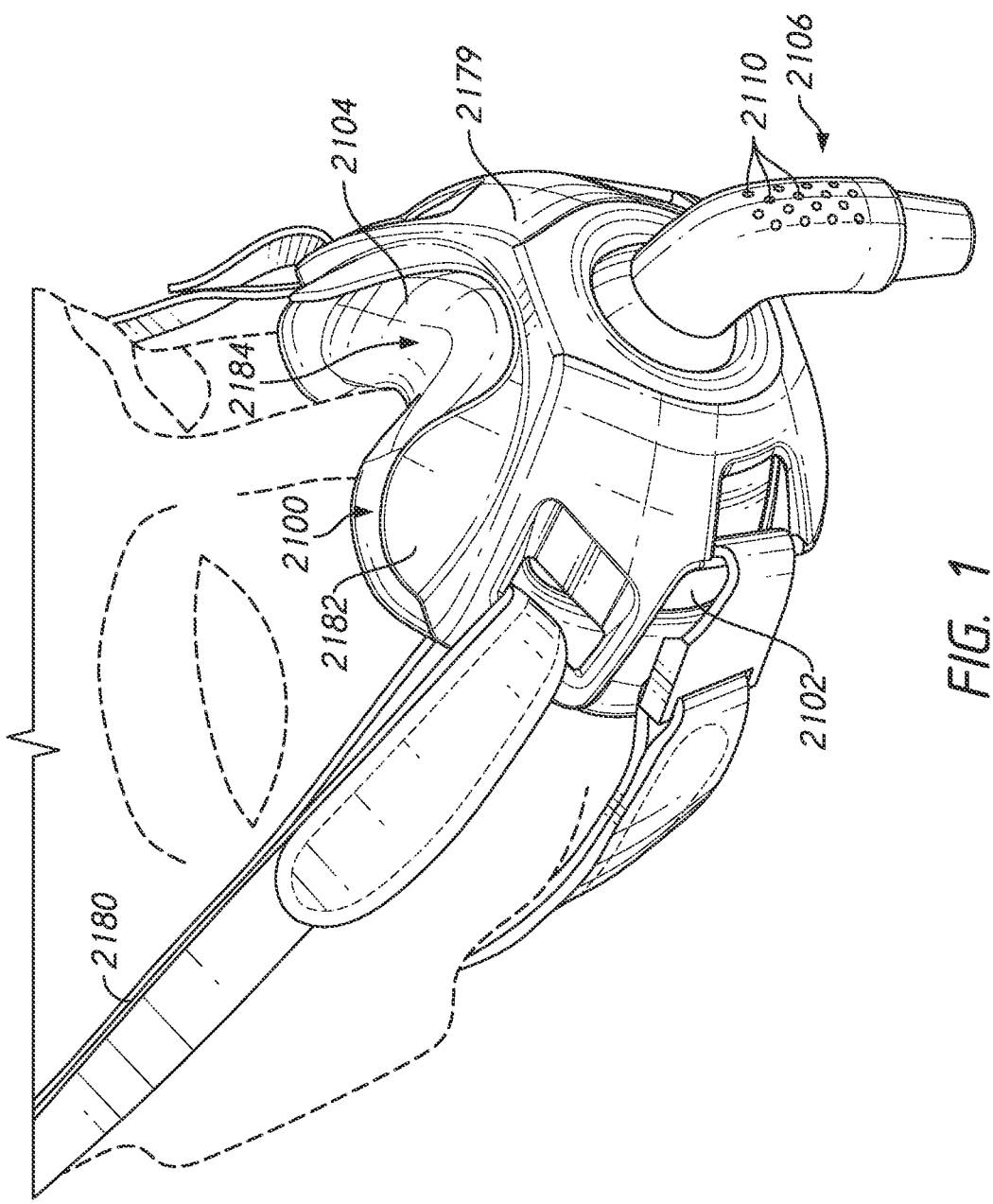
FIG. 1 is a front perspective view of an interface assembly having certain features, aspects and advantages of the present disclosure positioned on the head of a user.
Figure 2:
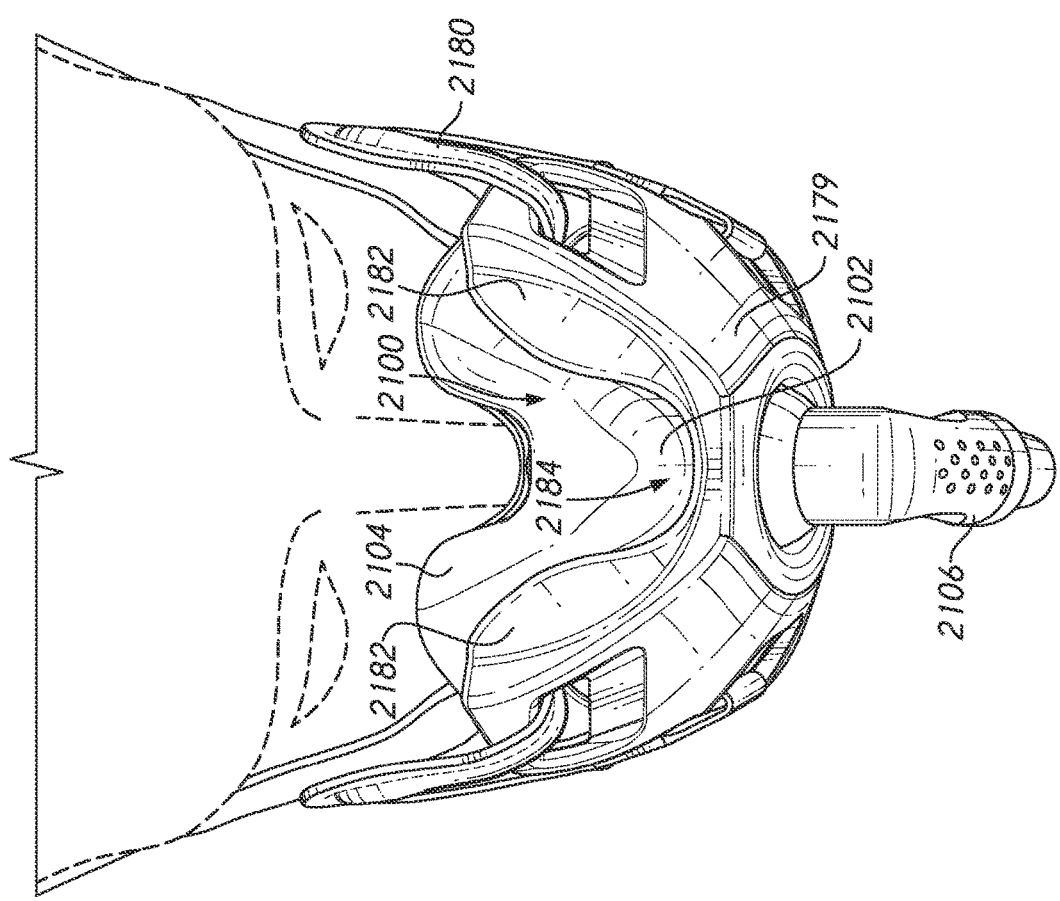
FIG. 2 is a top view of the interface assembly of FIG. 1 positioned on the head of a user.
Figure 6:
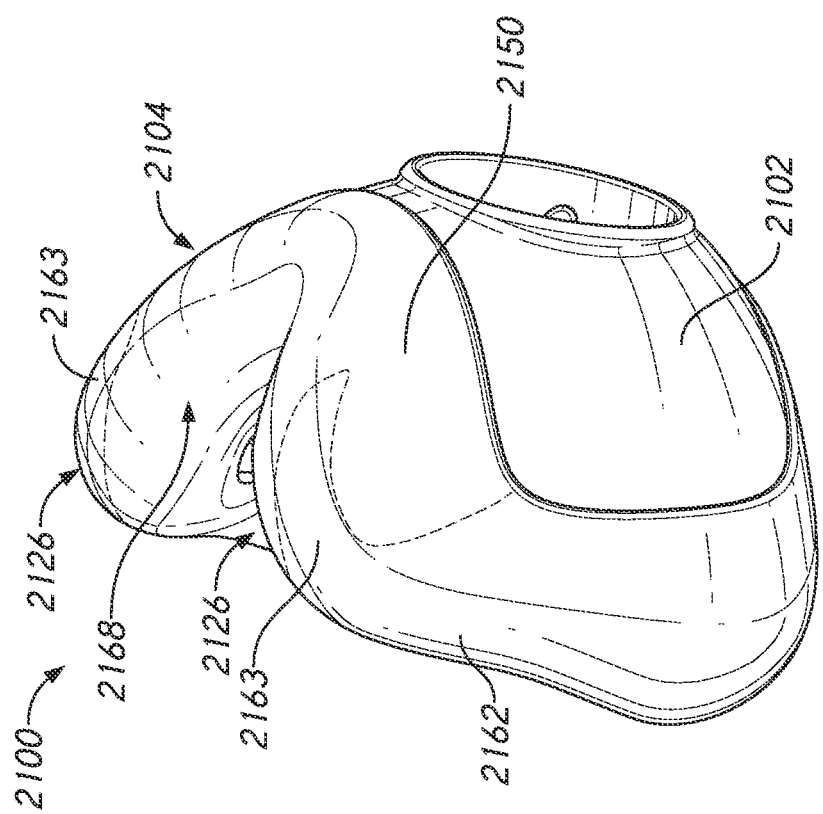
FIG. 6 is a side view of the mask assembly of FIG. 4 illustrating the thickened region of the mask seal.

Embodiments of systems, components and methods of assembly and manufacture will now be described with reference to the accompanying figures, wherein like numerals refer to like or similar elements throughout. Although several embodiments, examples and illustrations are disclosed below, it will be understood by those of ordinary skill in the art that the inventions described herein extends beyond the specifically disclosed embodiments, examples and illustrations, and can include other uses of the inventions and obvious modifications and equivalents thereof. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Certain terminology may be used in the following description for the purpose of reference only, and thus are not intended to be limiting. For example, terms such as "above" and "below" refer to directions in the drawings to which reference is made. Terms such as "front," "back," "left," "right," "rear," and "side" describe the orientation and/or location of portions of the components or elements within a consistent but arbitrary frame of reference which is made clear by reference to the text and the associated drawings describing the components or elements under discussion. For example, as the context may dictate, the terms "front" and/or forward can be used relative to components described herein positioned relatively or entirely distal to the user's face when the mask assembly as described herein is worn by the user. As the context may dictate, the terms "rear" and/or "back" can be used relative to components described herein positioned relatively or entirely proximal to the user's face and/or components that are forward or at the front of the mask assembly when the mask assembly as described herein is worn by the user Moreover, terms such as "first," "second," "third," and so on may be used to describe separate components. Such terminology may include the words specifically mentioned above, derivatives thereof, and words of similar import.

One or more of the embodiments described herein address issues with sealing and fitting a variety of facial (e.g., nasal) geometries that can be experienced with face masks. In particular, at least some of the embodiments are directed toward patient interfaces, such as face masks, which seal below the bridge of the user's nose and around the nares. However, the embodiments disclosed herein could also be adapted to other full face masks (e.g., those that partially cover and/or seal on the bridge of the user's nose).

One or more of the embodiments described herein address issues with creating a satisfactory seal on a variety of facial geometries with an under-nose seal. The reduced foot print of an under-nose nasal or combined nasal and oral mask on the user's face compared to conventional nasal or full face masks that contact the nasal bridge can make it more difficult to maintain a seal with the user's face and be configured to adapt to various facial geometries. Sealing around and below the nose can present challenges due to the variation seen in facial geometries from user to user. One or more of the embodiments illustrated herein can allow for expansion of, for example, a nasal portion of the mask seal in response to fitment on a particular user or in response to pressure within the mask seal. In some configurations, the nasal portion of the mask seal can be configured to allow for relatively low resistance to an increase in width. Such an arrangement can allow a single mask seal to create a satisfactory seal with a user having a relatively narrow nose and a user having a relatively wide nose. For example, the width of the nasal portion may not expand or increase in width, or may expand or increase in width only slightly, when used with a user having a relatively narrow nose. The width of the nasal portion may expand or increase in width significantly or to a maximum extent when used with a user having a relatively wide nose. However, in at least some configurations, even when expanded, the nasal portion does not apply an uncomfortable level of force on the nose of the user. Such an arrangement advantageously can maintain a satisfactory seal between the user's face and the mask seal.

Figure 75:
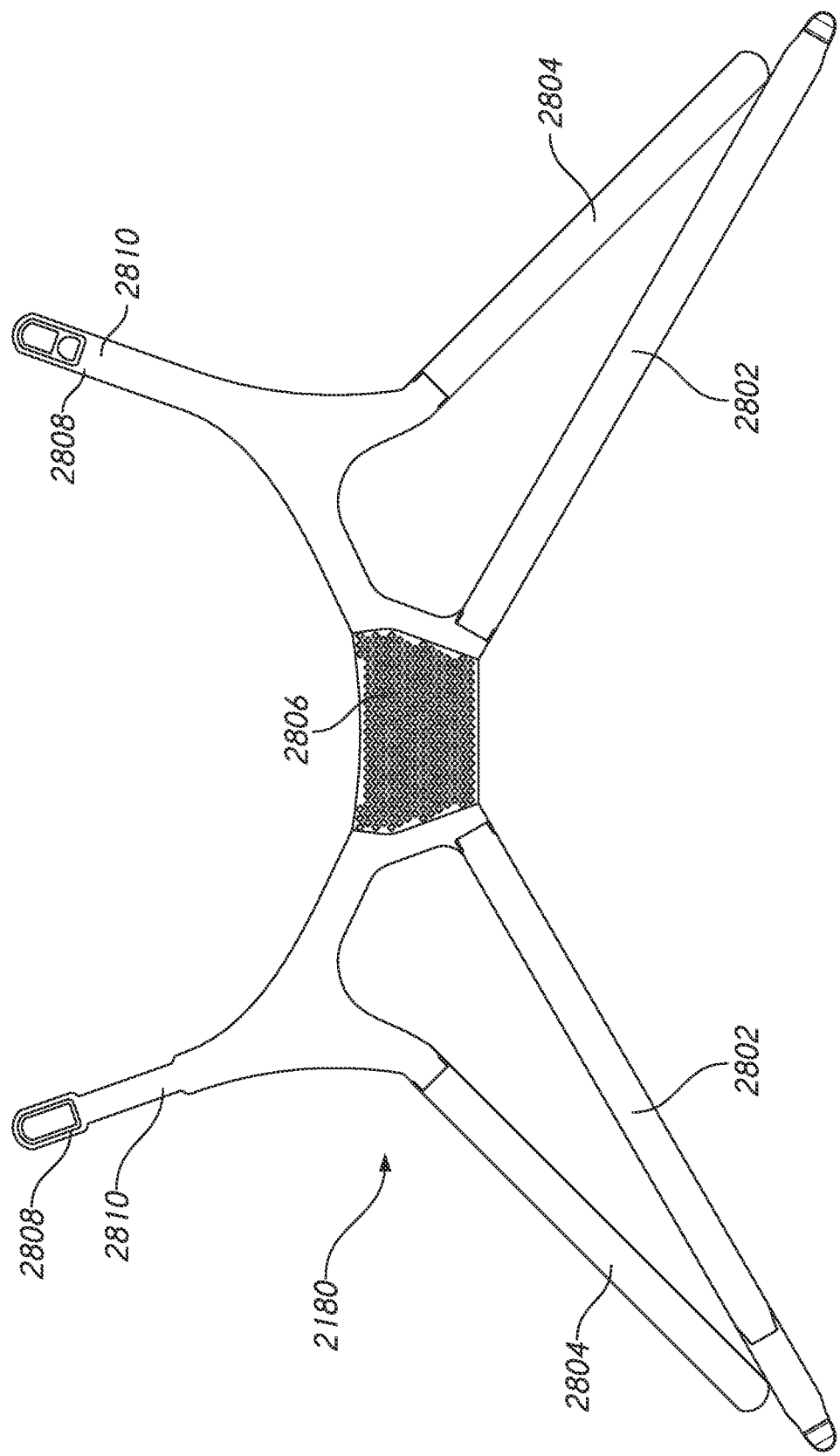
FIG. 75 is an interior surface view of the headgear assembly of FIG. 74 in a laid flat orientation.

FIGS. 1-75 illustrate a mask assembly 2100 and components thereof, both in position on a face of a user and separated from the face of the user. The illustrated mask assembly 2100 is a combined nasal and oral mask, which can be referred to herein as a nasal-oral mask. The illustrated mask assembly 2100 is designed to seal under the nose of the user, along a portion of the face extending lateral to the nose, as well as around the mouth of the user. The mask assembly 2100 advantageously does not require contact with the bridge of the nose of the user. In the illustrated configuration, the mask assembly 2100 does not extend over the bridge of the nose of the user. More particularly, the illustrated mask assembly 2100 does not contact the bridge of the nose of the user. Even more particularly, the illustrated assembly 2100 does not contact a forward facing portion of the bridge of the nose of the user. In some configurations, the assembly 2100 does not contact the face in a region vertically higher than a generally horizontal plane extending along the lower edges of the eyes of the user. The mask assembly 2100 may or may not extend over the tip of the nose of the user. Thus, in some configurations, the mask assembly 2100 covers the tip of the nose. In some configurations, the seal of the mask assembly 2100 covers the tip of the nose. In some configurations, the illustrated mask assembly 2100 preferably does not enshroud the tip of the nose of the user. In some configurations or with some facial geometries, the tip of the nose of the user extends over the adjoining portion of the mask assembly 2100.

As illustrated, the mask assembly 2100 preferably is adapted to extend around and seal over the wing or alar of the nose, which flares out to form a rounded eminence around the nostril. The illustrated mask assembly 2100 is adapted to seal around the surfaces that define the opening to the nostril, which may include a portion or entirety of the fleshy external end of the nasal septum, sometimes called the columella. In some configurations, the mask assembly 2100 is adapted to extend upwardly to seal along at least a portion of the left and right dorsal side walls of the nose of the user. In some configurations, the mask assembly 2100 is adapted to extend upwardly along at least a portion of the left and right dorsal side walls without extending upwardly to the region of the bridge of the nose of the user. In some configurations, a primary sealing surface of the mask assembly 2100 contacts the underside of the nose of the user, possibly along with the upper lip and/or a transition region between the underside of the nose and the upper lip. A secondary sealing surface of the mask can contact the side surfaces of the nose of the user, possibly along with the cheeks at a location near the nose. Such primary and secondary sealing surfaces may not make contact with the face of all users; however, such an arrangement can provide a suitable seal with a relatively large range of facial geometries. The mask assembly 2100 preferably also seals around at least a portion of the user's mouth. The mask assembly 2100 may or may not be adapted to seal between the mouth and nose of the user.

As illustrated, the mask assembly 2100 comprises a mask support, such as a base, housing or mask shell 2102 (see, for example, FIG. 4), for example. A mask seal or cushion 2104 can be attached to the housing 2102 such that the housing 2102 provides some amount of support for the mask seal 2104. However, in other configurations, the mask seal 2104 may not include a support and may be adapted for direct assembly to another component of the associated interface assembly. In some configurations, the housing 2102 can be substantially smaller than the illustrated housing. For example, the housing 2102 can define an opening that allows the mask assembly 2100 to be attached to another component, such as a frame and/or conduit connector (e.g., elbow) and the housing 2102 can be localized to the opening without providing direct support to other portions of the mask assembly 2100.

The mask assembly 2100 can be engaged with or otherwise supported by a frame 2178 that allows for connection to a head strap or headgear 2180 of any suitable arrangement. The mask assembly 2100 can be keyed to the frame 2178 to permit assembly in only the correct orientation. In some configurations, the head strap or headgear 2180 could be coupled directly to the mask assembly 2100 and the frame 2178 can be utilized for other purposes or omitted. A conduit connector 2106 can also be attached to the housing 2102, frame 2178 or otherwise supported relative to and adapted to communicate with an interior space of the mask assembly 2100. Together, the frame 2178 and the headgear 2180 can support the mask assembly 2100 in place on the user's face. Collectively, the mask assembly 2100, frame 2178 and headgear 2180 can be referred to as an interface assembly. The mask assembly 2100 or the mask assembly 2100 in combination with the frame 2178 can be referred to as an interface.

The illustrated conduit connector 2106 can be connected to the frame 2178 and/or housing 2102 in any suitable manner, including but not limited to any manner discussed elsewhere within this application. For example, but without limitation, the connector 2106 can be connected to the housing 2102 such that the connector 2106 can swivel, pivot or rotate relative to the housing 2102 about a single axis or about multiple axes. In some configurations, the connector 2106 can define a portion of a ball joint with the frame 2178 and/or mask housing 2102, for example but without limitation, defining the other portion. The ball joint can have any suitable configuration. The connector 2106 facilitates connection to a gases conduit, such as a supply conduit or the like for the supply of pressurized breathing gases to an interior of the mask assembly 2100. Any suitable connector 2106 can be used, which in some cases can include a swivel or rotational coupling that permits relative rotation between the connector 2106 and the gases conduit.

In the illustrated configuration, the connector 2106 comprises an elbow, such as a polycarbonate elbow for example but without limitation, that contains a vent. In the illustrated arrangement, the vent comprises bias flow holes 2110. However, the vent could comprise other geometries or arrangements, such as slots or a controlled leak between components, for example. The vent could also comprise diffuser materials to reduce noise and/or draft. The bias flow holes 2110 are a collection of orifices that are configured to exhaust air and flush $CO_2$ to reduce the likelihood of rebreathing expired carbon dioxide by the user. While the bias flow holes 2110 are shown exclusively on the connector 2106, in some configurations, the bias flow holes 2110 can be provided on the housing 2102, on the mask seal 2104 or on any combination of the connector 2106, the housing 2102 and the seal 2104 or on any other component of the interface assembly or associated breathing circuit. The bias flow holes 2110 can have any suitable cross-section and can be cylindrical, hour-glass shaped, tapered in either direction, fully or partially tapered, fully or partially cylindrical, contoured to vary in cross-section or the like.

The housing 2102 provides a support structure of sorts for the mask assembly 2100 in general and for the mask seal 2104 more specifically. The housing 2102 can be formed from any suitable material. In some configurations, the housing 2102 is formed from a fairly rigid material. In some configurations, the housing 2102 is formed from a plastic material, such as a polycarbonate material. In some configurations, the mask assembly 2100 can comprises a mask seal that includes a mask seal clip that is separate from but attachable to a housing. In such a configuration, the mask seal clip would connect the mask seal 2104 to the housing 2102. In such configurations, the mask seal and mask seal clip can be formed separately and secured together or the mask seal and the mask seal clip can be integrated into a single component. In some configurations, the mask seal can be overmoulded onto the mask seal clip and, in some configurations, the mask seal 2104 can be overmoulded directly onto the housing 2102, which can comprise chemical and/or mechanical overmoulding, for example.

In some configurations, the housing 2102 comprises a substantial portion of a forward wall of the mask assembly 2100. Such an arrangement provides an advantageous level of support to the mask seal 2104. For example, the housing 2102 comprises a substantial portion of an oral portion of the forward wall of the mask assembly 2100. In some configurations, the housing 2102 is generally limited to the oral portion of the mask assembly 2100 and does not extend into the nasal portion of the mask assembly 2100, at least to any significant extent. Such an arrangement can provide support to the mask seal 2104, while advantageously permitting movement or deformation of the nasal portion of the mask seal 2104. In other arrangements, the housing 2102 can extend into the nasal portion to provide additional support to the nasal portion, if desired. In the illustrated configuration, the housing 2102 sweeps rearward from a central portion 2112 toward opposing side portions 2116. The central portion 2112 contains an aperture 2114 for receiving the connector 2106. The housing 2102 can have a generally or substantially constant height throughout the central portion 2112 and opposing side portions 2116. In other arrangements, the housing 2102 can vary in height, such as by forming a shape that generally mimics the frontal shape of the mask seal 2104. The height of the housing 2102 can be substantially equal to a height of the oral portion of the mask seal 2104. A width of the housing 2102 can comprise a significant portion of the overall width of the oral portion of the mask assembly 2100, such as at least about three-quarters of the overall width of the oral portion of the mask assembly 2100. Such an arrangement of the housing 2102 can provide reinforcement to the central and lateral portions of the mask seal 2104. In some configurations, the housing 2102 could be minimal, such as an annular support ring or frame, for example.

The mask seal 2104 is designed to seal against the face of the user. The mask seal 2104 preferably is formed of a soft material, such as silicone, for example but without limitation. In some configurations, at least portions of the mask seal 2104 can be textured to improve comfort to the user. For example, in some configurations, at least portions of the mould used to form the illustrated mask seal 2104 can be bead blasted to provide a surface texture in at least the regions of the mask seal 2104 that will contact the skin of the user. Other techniques for texturing one or more surface of the mask seal 2104 can be used. In some configurations, it may be desirable to avoid surface texturing and provide at least the face-contacting surfaces of the mask seal 2104 with a smooth surface texture, which may increase grip of the mask seal 2104 on the user's face and improve sealing characteristics.

As described above, the illustrated mask seal 2104 comprises a nasal-oral mask seal and, therefore, comprises at least one oral opening 2122 and at least one nasal opening 2124. In some configurations, the mask seal 2104 can comprise a combined oral-nasal opening. In some configurations, the mask seal 2104 can comprise more than one nasal opening 2124. In some configurations, the mask seal 2104 can comprise nasal openings 2124 defined within superstructures, such as pillows, prongs or the like. In some configurations, the nasal opening 2124 can be defined by a nasal cushion or insert, which can be overmoulded or otherwise secured to a base structure of the mask seal 2104. An example of such an arrangement is disclosed in Applicant's publication no. WO 2014/062070, the entirety of which is incorporated by reference herein.

The at least one oral opening 2122 and the at least one nasal opening 2124 preferably communicate with a single chamber 2125 that is defined within the mask assembly 2100. The chamber 2125 of the illustrated mask assembly 2100 is at least partially defined by the housing 2102 and the mask seal 2104. The at least one oral opening 2122 is substantially opposed to the aperture 2114 that receives or communicates with the connector 2106. The at least one nasal opening 2124 can be vertically above the at least one oral opening 2122. The at least one nasal opening 2124 can be positioned between the aperture 2114 for the connector 2106 and the at least one oral opening 2122 in a fore-aft direction of the mask assembly 2100. The at least one nasal opening can have an axis that is inclined relative to vertical and that, in some arrangements, can generally extend through the aperture 2114 for the connector 2106.

Figure 7:
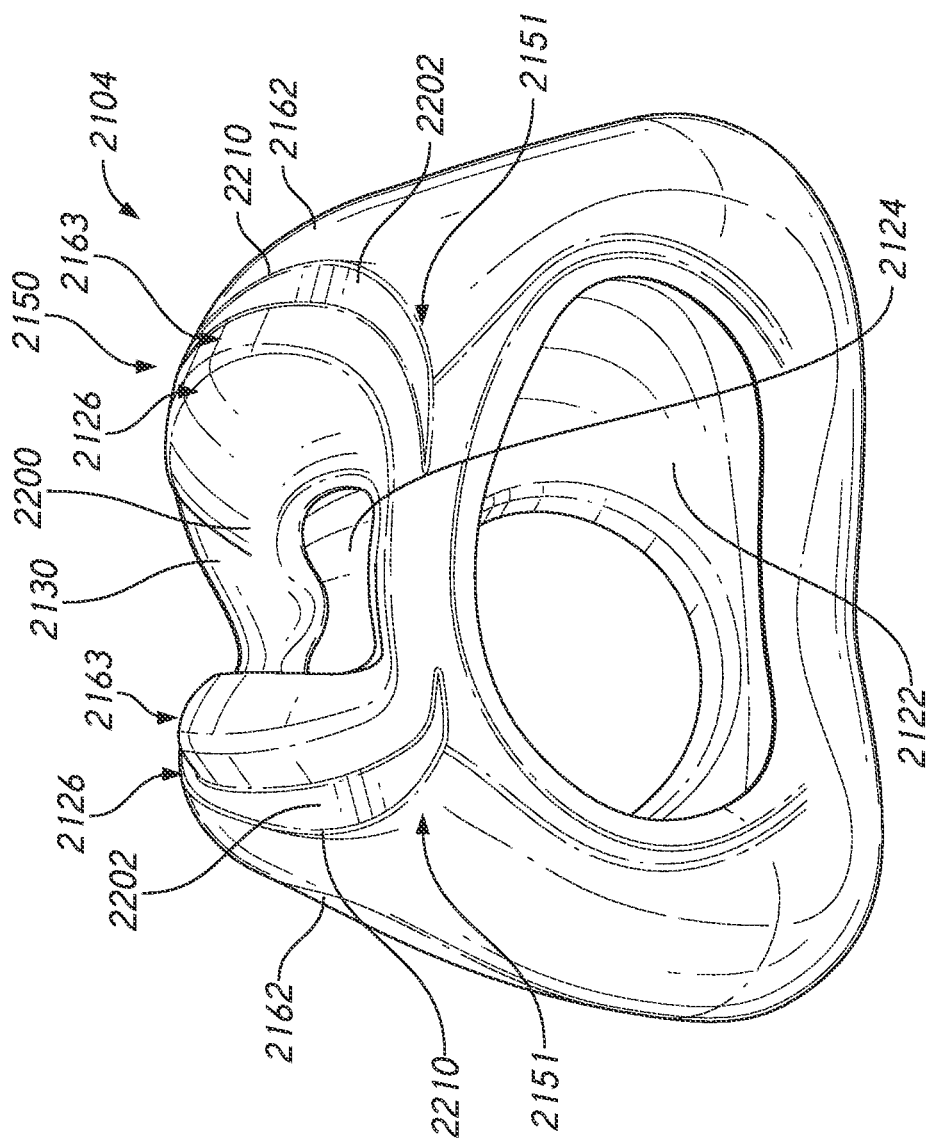
FIG. 7 is a rear view of a mask assembly illustrating a cut-out region of a mask seal of the mask assembly.

The mask seal 2104 preferably comprises a pair of paddles 2126 that extend upward above an upper surface 2130 (See, for example, FIG. 7) of a central portion of the mask seal 2104. The upper surface 2130 can define a line that lies along a central surface of the nasal surface of the mask seal 2104 in a fore-aft direction. Such a line extends generally along the nasal septum in a direction away from the user's face. The paddles 2126 are configured to extend upward alongside, and in some configurations above, the nares. The paddles 2126 can contact the edges of the nares and/or sides of the nose. The paddles 2126 or portions of the mask seal 2104 between the paddles 2126 may or may not cover the tip of the user's nose. As described herein, preferably the mask seal 2104 does not contact the bridge of the user's nose.

In some configurations, the paddles 2126 each comprise an air pocket that is in direct fluid communication with the air path through the mask assembly 2100 from the connector 2106 to the at least one nasal opening 2124 and the at least one oral opening 2122. The paddles 2126 can be configured to expand in volume in response to elevated pressure within the mask seal 2104 and/or flex inwardly to accommodate various facial and nasal geometries and assist in creating a sealed contact with the user's face. Expansion of the paddles 2126 can assist in sealing against the face of the user, especially along the varying contours on and around the user's nose. Inward flexing of the paddles 2126 allows the central portion (e.g., upper surface 2130) to move downward with less restriction or less stretching of the material of the mask seal 2104 so that the mask seal 2104 can better conform to various nasal geometries. Similarly, as described in more detail below, cutout regions 2202 of the support structure 2163 can advantageously allow the mask seal to maintain a sealed contact with the user's face in response to elevated pressure within the mask seal 2104.

The height of the paddles 2126 above the upper surface 2130 can be selected to provide a desired balance between stability of the mask seal 2104 on the user's face (e.g., vertical stability) and being able to accommodate a range of nasal geometries or reducing visual disruption by the paddles 2126. In general, paddles 2126 positioned higher tend to provide additional vertical stability of the mask assembly 2100, while paddles 2126 positioned lower tend to provide a better fit of a wider range of users and result in less visual disruption. In some configurations, the paddles 2126 can have a height between about 10 mm and about 30 mm or between about 15 mm and about 25 mm. In some configurations, the paddle height 2126 is between about 15 mm and about 22 mm or between about 18 mm and about 20 mm, including any value or sub-range within the above-described ranges. In some configurations, the paddle height is about 18.5 mm.

The mask seal 2104 can also comprise the support structures or supports 2163 for the paddles 2126, which can be in the form of suspension members or springs that provide mechanical rigidity and structure to hold the shape of the paddles 2126 when the mask seal 2104 is worn by a user. The supports 2163 can comprise thickened regions of the seal material. The supports 2163 preferably are sized, shaped and/or otherwise configured to transfer force from a rearward or user-contacting surface of the paddles 2126 toward or to a forward surface of the paddles 2126. In some configurations, the interface can include a support portion or cover for the paddles 2126 and the supports 2163 can transfer force from the rearward surface of the paddles 2126 to the forward surface or other portion of the paddles 2126 or mask seal 2104 that contacts or faces the support portion or cover. In some configurations, the supports 2163 can transfer force from the rearward surface of the paddles 2126 toward or to another support portion of the mask seal 2104 (e.g., the housing 2102) or interface. The supports 2163 can resist or prevent collapse of the paddles 2126 or other related or adjacent portions of the mask seal 2104 to facilitate fitment and provide feedback to the user, such as in response to applied forces (e.g., headgear forces). In some configurations, the supports 2163 can resist or prevent collapse of the paddles 2126 or other related or adjacent portions of the mask seal 2104 in the absence of significant internal gas pressure.

The supports 2163 can help maintain the shape of the paddles 2126 of the mask seal 2104 and/or help maintain a separation between a rear wall of the mask seal 2104 (defining a face contacting surface) and a front wall of the mask seal 2104 at least in response to forces experience during normal use. In addition, the supports 2163 can provide support to the nasal region or nasal seal portion 2168. In particular, the supports 2163 can provide structure to and inhibit or prevent creasing, wrinkling or collapsing of the nasal region 2168 and/or the upper front portion 2150. As described above, the nasal region 2168 and/or the upper front portion 2150 preferably are relatively thin to permit these portions of the mask seal 2104 to conform to the user's nose. The relatively thin nasal region 2168 and/or the upper front portion 2150 can expand and seal around the user's nose. The supports 2163 provide rigid portions or elements of the seal 2104 adjacent or near the relatively thin nasal region 2168 and/or the upper front portion 2150 to inhibit or prevent collapse when a user engages his or her nose into the mask assembly 2100. The upper rear portion 2156 can assist in preventing collapse of the nasal region 2168 and/or the upper front portion 2150.

In some configurations, the supports 2163 help to reduce the likelihood of wrinkling or creasing of the face contacting portions of the paddles 2126 during use while allowing the laterally inner portions to be as thin as desired within practical limitations, such as those described above. The supports 2163 can assist in inhibiting or preventing collapse of the paddles 2126 or maintaining a desired shape of the paddles 2126. For example, the supports 2163 can assist in maintaining a desired fore-aft shape of the paddles 2126 and/or a lateral or side-to-side shape of the paddles 2126. The level of support provided can vary in different directions. In some configurations, the supports 2163 could be formed as separate portions or separate components from the seal material and could be the same or a different material. Such separate supports 2163 could be coupled to the paddles 2126 or other portion of the mask seal 2104 if desired. The supports 2163 disclosed herein can be particularly useful in under-nose type mask assemblies, including both nasal masks and combined nasal-oral masks. However, the supports 2163 can also be utilized in other types of mask assemblies or interfaces, including those that cover, contact or seal against the bridge of the user's nose and/or include a T piece or other type of forehead support, for example and without limitation. The supports 2163 can be utilized, or modified for use, in any locations of an interface in which support against collapsing and/or support against overexpansion may be desirable. Such locations can be at or near the portion of the seal that contacts or extends alongside the user's nose or can be at other locations.

In the illustrated arrangement, at least a portion of the supports 2163 extend generally in a fore-aft direction along the paddles 2126. In particular, the supports 2163 can extend along the upper edge of the paddles 2126 or the region or ridge that joins the laterally outer surface portion and the laterally inner surface portion along the upper edges of the paddles 2126. The supports 2163 can extend along a portion of the sides of the nasal region 2168. The supports 2163 can comprise a generally thin, elongate shape. Viewed from above, the supports 2163 can comprise a generally triangular shape with a base of the triangle positioned rearwardly of the top or point of the triangle. Other shapes are possible to achieve a desired level of support or for other design considerations, such as the desired shape(s) of adjacent or nearby structures. The supports 2163 can have additional portions to provide other levels of support or to provide support in other directions. For example, the supports 2163 could connect to one another, such as along one or both of the forward or rearward sides of the nasal opening 2124. In some configurations, the supports 2163 could extend completely through the paddles 2126, such as to the housing 2102, for example.

As shown in FIGS. 7-18B, the paddles 2126 (or for example, the supports 2163) can each comprise a thinned and/or cutout region 2202. The cutout region 2202 can extend rearwardly and be positioned below a nasal region of each of the paddles 2126. In some configurations, the cutout region 2202 extends rearwardly and is positioned adjacent a nasal region of each of the paddles 2126. However, in other configurations, the cutout region 2202 extends rearwardly and is positioned laterally offset from a nasal region of each of the paddles 2126. The cutout region 2202 can extend from an upper front portion 2150 of the mask seal 2104 to an upper rear portion 2151 of the mask seal 2104 such that the cutout regions 2202 wrap around lateral side portions 2210 of each of the paddles 2126. Accordingly, in some configurations, the cutout regions 2202 are generally curved, straight, and/or have variable curvature. In some configurations, the cutout region 2202 can be inclined from the upper front portion 2150 to the upper rear portion 2151 and/or the upper rear portion 2151 to the upper front portion 2150. In some other configurations, the cutout regions 2202 are substantially flat or have minimal inclination.

As shown in the illustrated configurations, the cutout regions 2202 extend across at least a portion of the upper front portion 2150 and at least a portion of the rear portion 2151. For example, the cutout regions 2202 can extend around the lateral side portions 2210 of the mask seal 2104 and across the rear portion 2151 towards an approximate center of the upper rear portion above the oral opening 2122. In some configurations, the cutout regions 2202 extend across approximately $\frac{1}{16}$, $\frac{1}{8}$, $\frac{1}{4}$, and/or $\frac{1}{2}$ or more of the upper rear portion and/or the upper front portion. In some configurations, the cutout regions 2202 extend a distance across the upper rear portion 2151 that does not reach a position of a lateral side of nasal opening 2124 of the nasal region 2200.

In the illustrated configuration, the cutout regions 2202 are positioned below the nasal region of the paddles 2126. However, in other configurations, the cutout regions 2202 can be positioned above and/or in the same plane as the nasal region of the paddles 2126. For example, the cutout regions 2202 can be positioned approximately 0.1 to 0.5 mm, 0.5 to 1 mm, 1 to 10 mm, 10 to 50 mm, 50 mm to 1 cm, 1 cm to 2 cm, and/or 2 cm to 3 cm or more or more below the nasal region of the paddles 2126. In some configurations, the cutout regions 2202 are positioned nearly adjacent an upper side of the oral opening 2122. In yet other configurations, the cutout regions 2202 are positioned above, below and/or are planar with the nasal opening 2124. However, in some configurations, the cutout region 2202 extends along a lateral side of the paddles 2126. In such configurations, the cutout regions 2202 may not extend across a portion of the upper front portion 2150 and/or a portion of the upper rear portion 2151 and may be limited to the paddles 2126 or terminate within the nasal region 2200.

The illustrated mask seal 2104 of the mask assembly 2100 comprises a range and configuration of thicknesses, as shown in FIGS. 7-18B. The thicknesses are varied to take advantage of or provide different characteristics in different regions of the illustrated mask seal 2104. For example, the thicknesses in the various regions can be selected to address a desired characteristic for that region and/or the mask seal 2104 as a whole. Such characteristics can include, for example, allowing the mask seal 2104 to conform to the facial geometry of the user to enhance sealing properties or comfort, supporting the shape of the mask seal without significant internal gas pressure to facilitate fitment and/or in response to internal gas pressure and/or external pressure (e.g., caused by headgear forces) or providing strength or durability.

As described above, the mask seal 2104 can include various regions of different thickness. Examples of such arrangements are disclosed in Applicant's publication no. WO 2015/193821A1, the entirety of which is incorporated by reference herein. In general, the outer surface of the mask seal 2104 defines a relatively smoothly shaped or curved surface without abrupt changes in direction. The different thicknesses are created by changes in wall thickness that are apparent on or created by changes in shape of an interior surface of the mask seal 2104.

The supports 2163 can have a different thickness than other portions of the paddles 2126 and can have a greater thickness than other portions of the paddles 2126. In some configurations, the supports 2163 can have the largest thickness or among the largest thicknesses of the mask seal 2104. In some configurations, a portion or an entirety of the supports 2163 can have a thickness of between about 1.5 mm and about 3.5 mm. In the illustrated configuration, a portion or an entirety of the supports 2163 can have a thickness of about 2.5 mm. The thickness of the supports 2163 can be constant or variable.

In some configurations, support structures 2163 for the paddles are thicker than a nasal region 2168 and an upper front portion 2150. In some configurations, a relatively abrupt transition in thickness occurs between the nasal region 2168 and upper front portion 2150 and the paddles 2126. In contrast, transitions in thickness between outer peripheral portions 2162, the paddles 2126 and an upper rear portion 2151 are more gradual. In addition, in at least some configurations, transitions in thickness between the outer peripheral portions 2162, the upper rear portion 2151 and the oral opening 2122 are relatively gradual. The various portions of the mask seal 2104 are described further below.

To reduce the incidence of wrinkling of at least some of the face contacting regions of the mask seal 2104 during use, it has been found that the outer peripheral portions 2162 of the mask seal 2104, which are generally adjacent to some or all of the face contacting portions of the mask seal 2104, provide desirable performance when the outer peripheral portions 2162 are fairly rigid or relatively rigid compared to adjacent portions or other portions of the mask seal 2104. In the illustrated arrangement, the outer peripheral portions 2162 extend along the generally vertically extending portions on the rear of the mask seal 2104 and wrap slightly inward at a bottom of the rear of the mask seal 2104. In addition, the outer peripheral portions 2162 wrap from a rear facing side of the mask seal around to at least a portion of a laterally facing side of the mask seal 2104.

In the illustrated arrangements, the outer peripheral portions 2162 are located on each lateral side of the oral opening 2122. In some configurations, the outer peripheral portions 2162 extend along an entire height of the oral opening 2122. Upper ends of the outer peripheral portions 2162 can extend at least to about an upper end of the oral opening 2122. Lower ends of the outer peripheral portions 2162 can extend below a lower end of the oral opening 2122. As described above, in some configurations the outer peripheral portions 2162 wrap inwardly below the oral opening 2122 such that portions of the outer peripheral portions 2162 are positioned vertically below portions of the oral opening 2122.

The relatively increased thickness of the outer peripheral portions 2162 can assist in resisting or preventing collapse of the mask seal 2104 in the absence of significant internal gas pressure to facilitate fitment and provide feedback to the user, such as in response to applied forces (e.g., headgear forces). The outer peripheral portions 2162 can help maintain the curved shape of the lateral sides of the mask seal 2104 and/or help maintain a separation between a rear wall of the mask seal 2104 (defining a face contacting surface) and a front wall of the mask seal 2104 at least in response to forces experience during normal use. In some configurations, the thickness of a portion or an entirety of the outer peripheral portions 2162 can be between about 1.0 mm and about 2.0 mm. In the illustrated configuration, a portion or an entirety of the outer peripheral portions 2162 preferably have a thickness of about 1.5 mm. The thicknesses of the outer peripheral portions 2162 can be consistent or varied within a boundary of the outer peripheral portion 2162.

In some configurations, the cutout regions 2202 have a reduced wall thickness compared to surrounding seal surfaces (e.g., support structures 2163). For example, some or all of the cutout regions 2202 can have a reduced wall thickness compared to surrounding seal surfaces, all or a portion of which can be defined by all or a portion of the support structure 2163, in at least some embodiments. In some configurations, the surrounding seal surfaces include an approximate wall thickness of 3 mm. As described above, some or all of the surrounding seal surfaces, including the outer peripheral portions 2162 can have a thickness of between about 1.0 mm and about 2.0 mm. However, the cutout regions 2202 of the support structure 2163 may have a wall thickness between about 0.1 to 0.2 mm, 0.2 to 0.3 mm, 0.3 to 0.4 mm, 0.4 to 0.5 mm, 0.5 to 0.6 mm, 0.6 mm to 0.7 mm, 0.7 to 0.8 mm, 0.8 to 0.9 mm, and/or 0.9 to 1.0 mm or more, for example. In the illustrated configuration, a portion or an entirety of the cutout regions 2202 preferably have a wall thickness of about 0.3 mm. The thickness of the cutout regions 2202 can be consistent or varied within a boundary of the cutout regions 2202.

The reduced wall thickness of the cutout regions 2202 compared to the surrounding seal surfaces can desirably provide a region that is more deformable and/or compressible than the surrounding seal surfaces. For example, the cutout regions may be less rigid and/or more expandable than surrounding seal surfaces. This may be desirable when, for example, a lateral force is applied to the paddles 2126, such as by a wider nose. Thus, the cutout regions 2202 may be capable of compressing more easily compared to paddles 2126 without the cutout region 2202, and/or with or without support structures 2163, to better accommodate the lateral forces applied to the nasal region of the paddles 2126. Instead of remaining rigid, the cutout regions 2202 would allow the paddles 2126 to compress while at the same time maintain the structural integrity of the mask seal assembly (see, for example, FIGS. 10A-10C, 11A-11B). This configuration may be more comfortable to the patient wearing the mask seal assembly.

Figure 8:
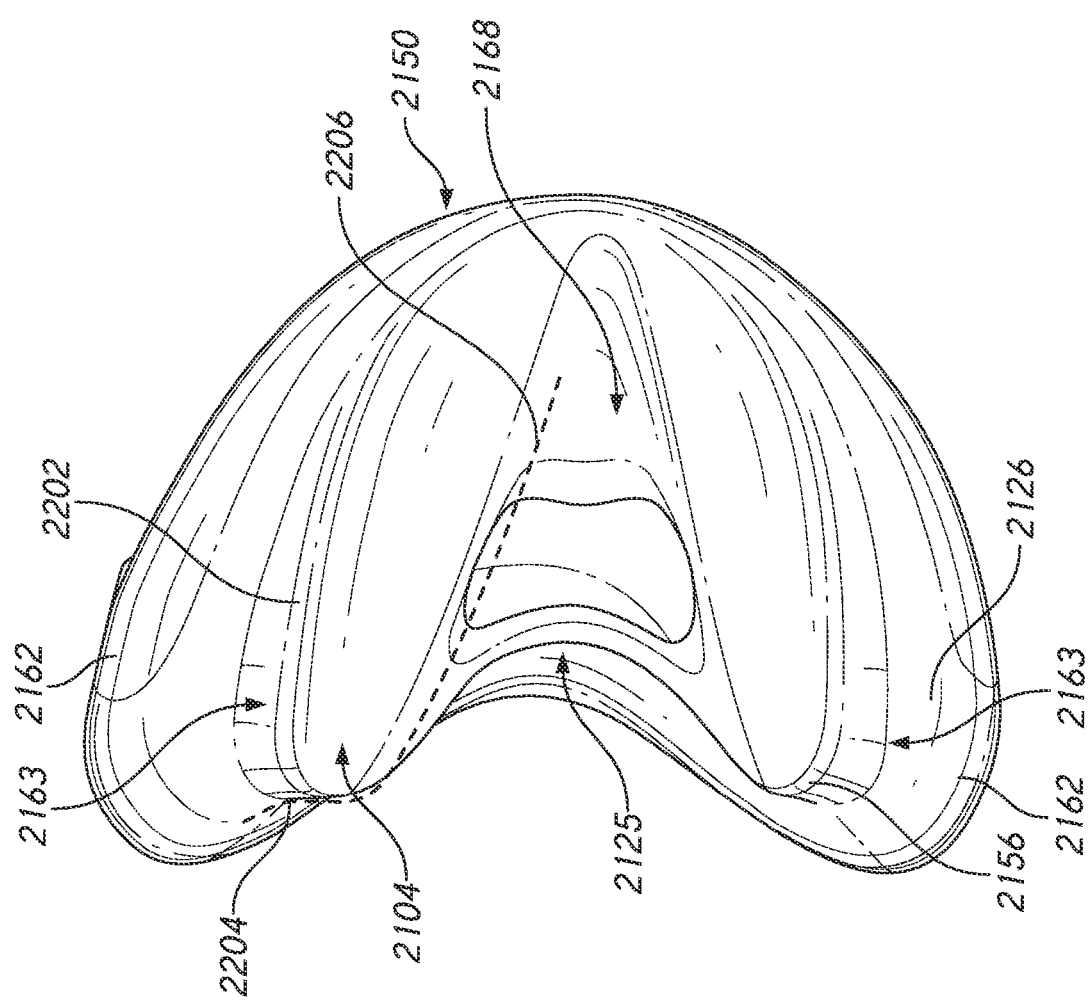
FIG. 8 is a top view of the mask assembly of FIG. 7 illustrating a cut-out region of the mask seal.

In some configurations, the cutout region 2202 of the support structure 2163 of the mask seal 2104 comprises a concave contour 2204. For example, FIG. 8 illustrates that the cutout regions 2202 include a concave contour 2204 at a rear portion 2160 of the cutout regions 2202. In the illustrated configuration, a relative low point of the concave contour 2204 is positioned at approximately a center of the rear portion 2160 of each of the cutout regions 2202. However, in other configurations, the concave contour is positioned closer to one side. In yet other configurations, the concave contour 2204 of the cutout regions 2202 is positioned closer to the nasal region of the paddles 2126.

In some configurations, the cutout regions 2202 include a concave contour 2204 along a portion or an entire length of the cutout region 2202. In the illustrated configuration, a relative low point of the concave contour 2204 is positioned at approximately a center of a width of each of the cutout regions 2202. However, in other configurations, the concave contour is positioned closer to one side. In yet other configurations, the concave contour 2204 of the cutout regions 2202 is positioned closer to the nasal region of the paddles 2126. As shown in FIG. 8, the concave contour 2204 smoothly transitions inwardly along the rear portion 2160 of the cutout regions 2202. In some configurations, the concave contour 2204 extends a relatively short distance inwardly towards the upper front portion 2150 of the mask seal 2104. In some configurations, the concave contour 2204 extends a more substantial distance inwardly towards the upper front portion 2150 of the mask seal 2104. In some configurations, the concave contour 2204 extends downwardly along the rear portion 2160 of the cutout regions 2202.

Generally, expansion of the paddles 2126 can assist in sealing against the face of the user, especially along the varying surface contours 2206 on and around the user's nose. For example, as shown in FIG. 8, nasal region 2168 includes a surface contour 2206. The surface contour 2206 can extend along an inner side of nasal region 2168. The surface contour 2206 can extend generally inwardly from the upper rear portion of the mask seal 2104 towards a center of the upper front portion 2150 of the mask seal 2104. The surface contour 2206 can desirably increase comfort to the patient and assist in ensuring a seal is formed with the user's face, while allowing outward movement, of the nasal region 2168, when necessary to accommodate a particular user.

FIGS. 9A-9D show a close up view of the concave contour 2204 of the cutout regions 2202 of the support structure 2163. As shown in the illustrated configuration, the concave contour 2204 can extend vertically downwardly (relative to the orientation shown in FIGS. 9A-9D) and inwardly towards an interior of the mask seal 2104. Thus, the concave contour 2204 can allow the cutout regions 2202 to fold inwardly towards an interior of the mask seal 2104 when a sufficient force is applied to the paddles 2126.

Generally, the concave contour 2204, the surface contour 2206 and/or the reduced thickness of the walls of the cutout regions 2202 can contribute to reduced material. This can desirably reduce bulk and increase comfort to the patient. In some configurations, the concave contour 2204 can encourage walls of the cutout regions 2202 to fold inwardly towards an interior chamber 2125 of the mask seal assembly. This can advantageously reduce bulk, as the mask seal 2104 folds against the patient's face. Similarly, the concave contour 2204 of the cutout regions 2202 can assist in minimizing leaks by forming a better seal with the user's face when the mask seal 2104 is worn by the user. For example, rather than expanding outwardly and or popping outwardly as the mask seal 2104 expands laterally, the cutout portions 2202 can advantageously fold inwardly to maintain engagement with the user's face and prevent the mask seal 2104 from shifting to an undesirable position.

In some configurations, the concave contour 2204 allows for better compression of the cutout regions 2202 when a force is applied to the paddles 2126. As described above, the concave contour 2204 can allow the cutout regions 2202 to fold laterally and/or vertically and inwardly when a lateral force is applied to the paddles 2126.

Figure 10C:
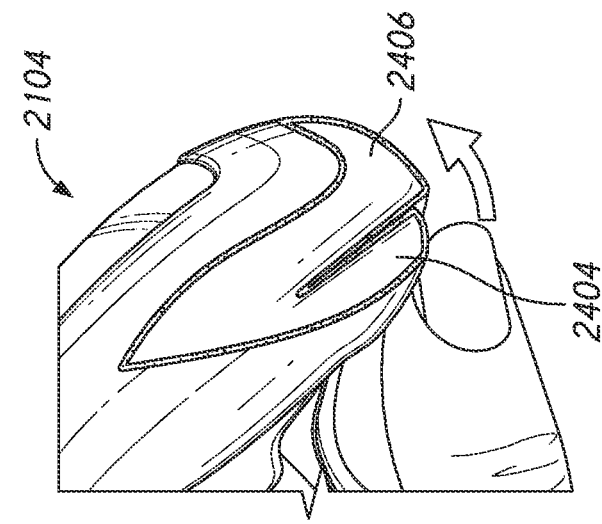
FIG. 10C is a top view of the mask assembly of FIG. 10A illustrating the cut-out region of the mask seal that is partially compressed.
Figure 10B:
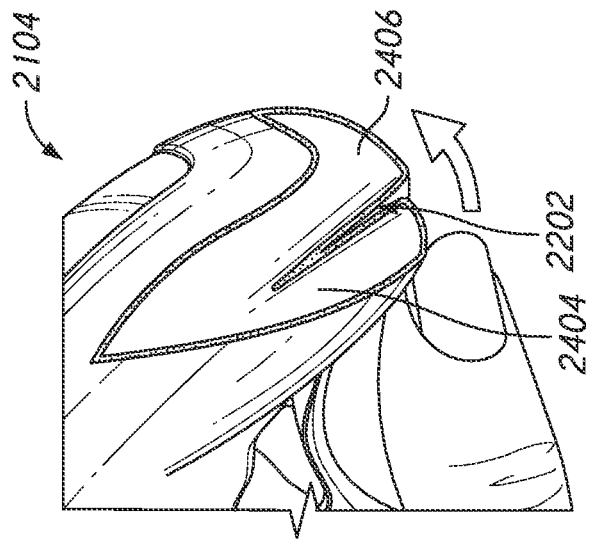
FIG. 10B is a top view of the mask assembly of FIG. 10A illustrating the cut-out region of the mask seal that is partially compressed.
Figure 10A:
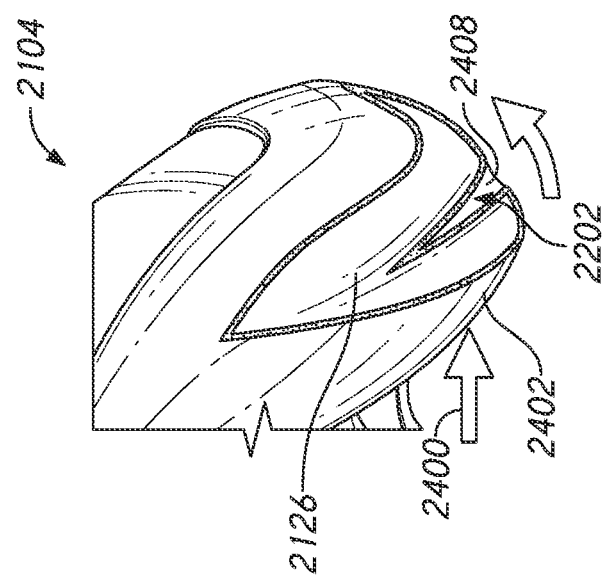
FIG. 10A is a partial top view of a mask assembly illustrating a cut-out region of a mask seal of the mask assembly that is generally uncompressed.
Figure 11A:
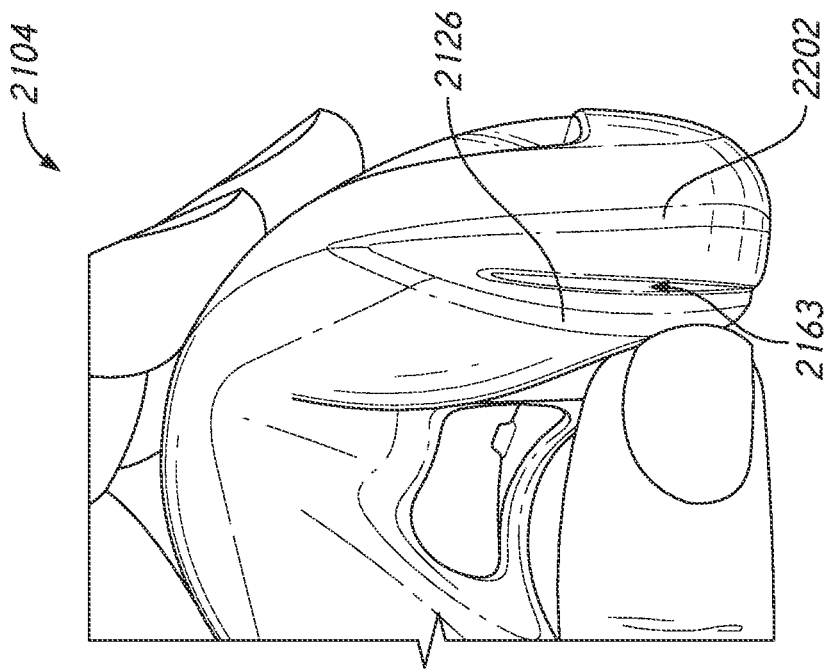
FIG. 11A is a top perspective view of the mask assembly of FIG. 10A illustrating the cut-out region of the mask seal that is generally uncompressed.
Figure 11B:
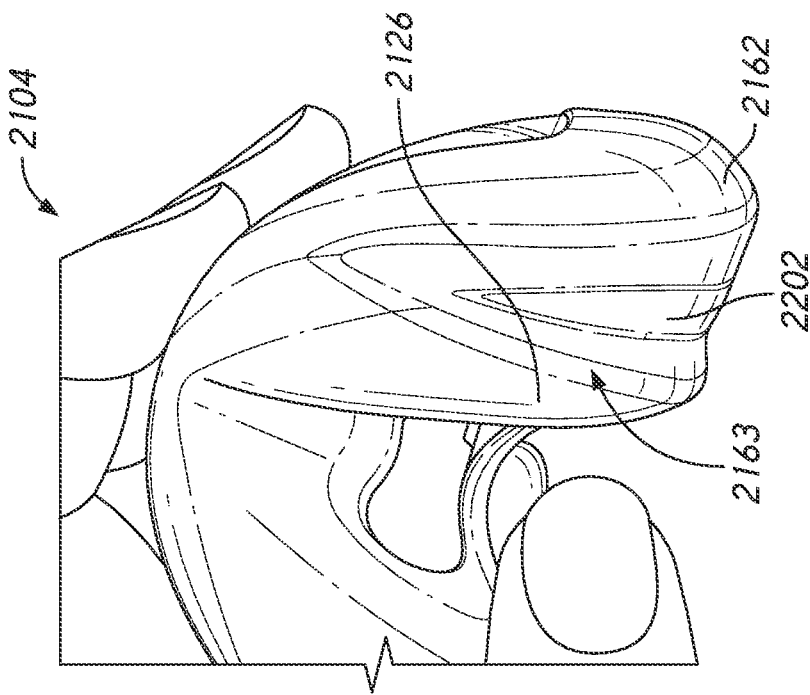
FIG. 11B is a top view of the mask assembly of FIG. 10A illustrating the cut-out region of the mask seal that is partially compressed.
Figure 12:
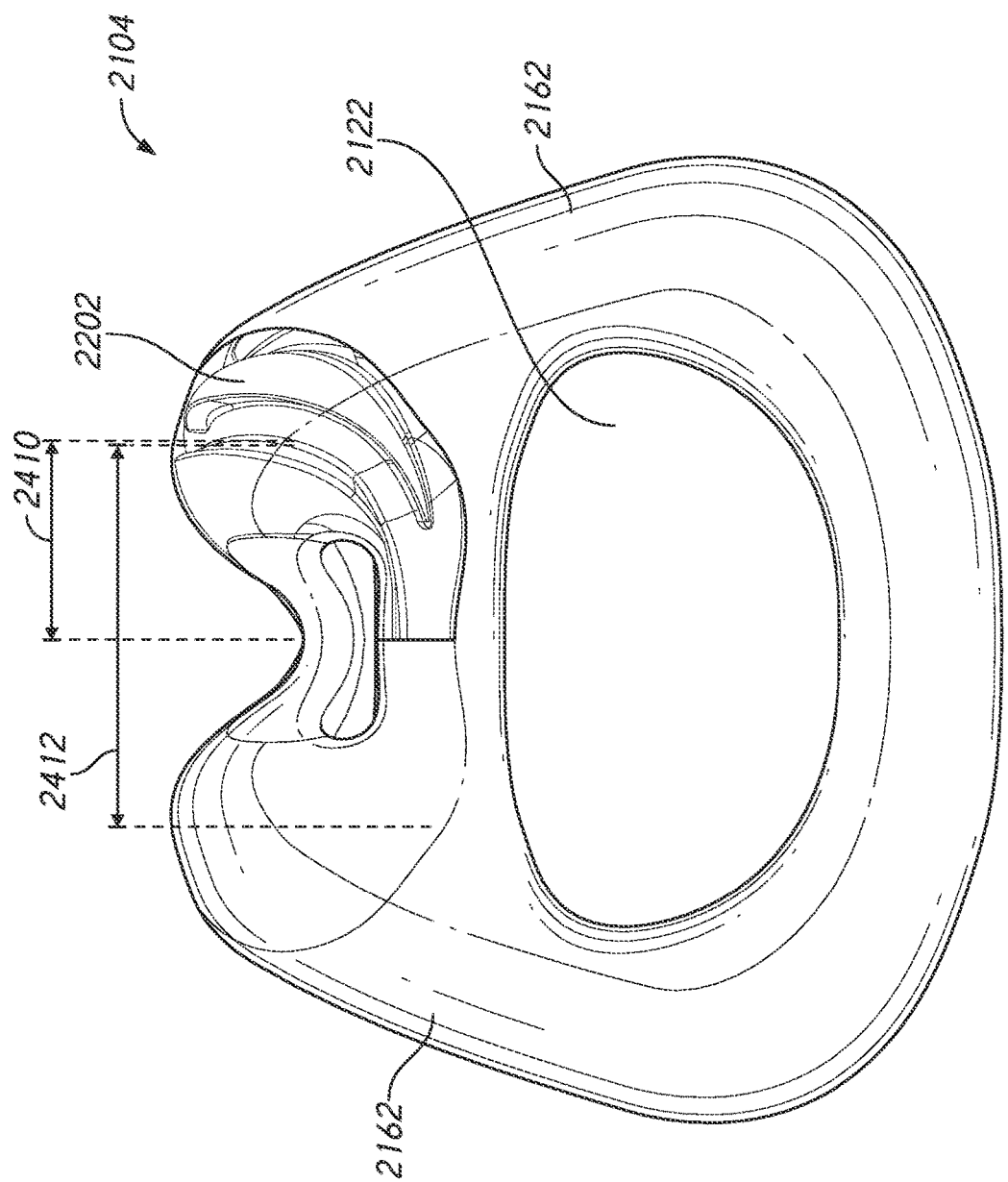
FIG. 12 is a rear view of a mask seal of a mask assembly illustrating a cut-out region of the mask seal.
Figure 13:
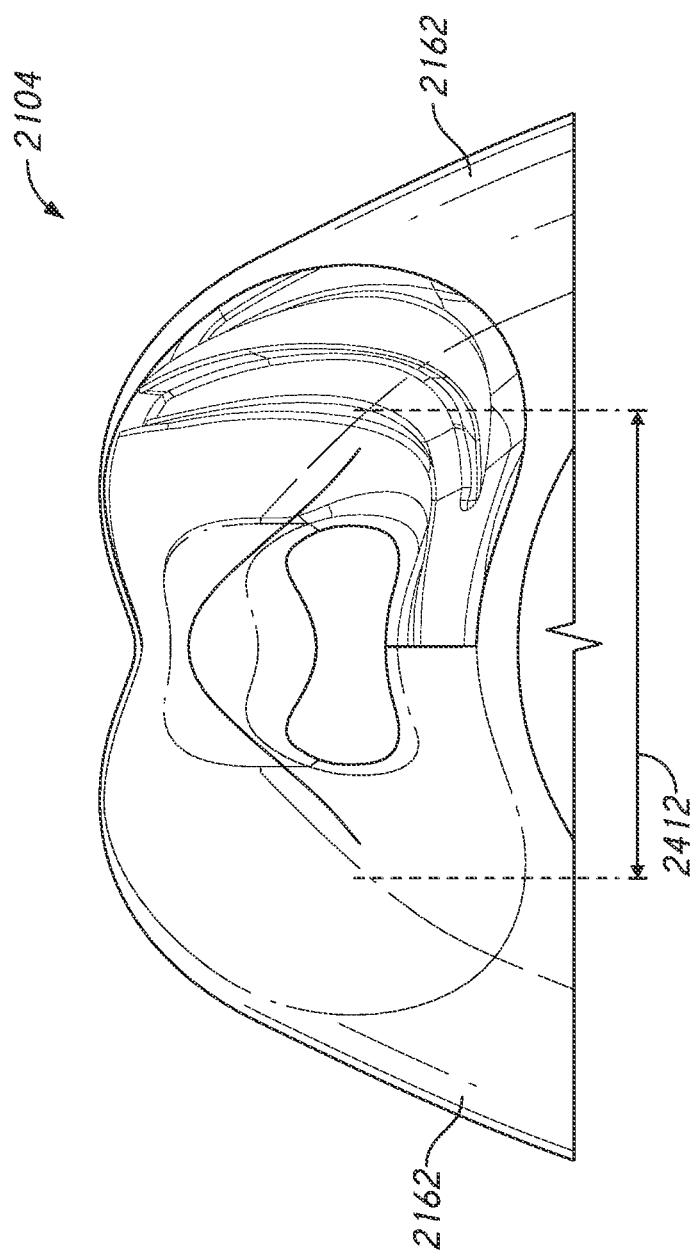
FIG. 13 is a partial rear view of the mask assembly of FIG. 12 illustrating the cut-out region of the mask seal.
Figure 14:
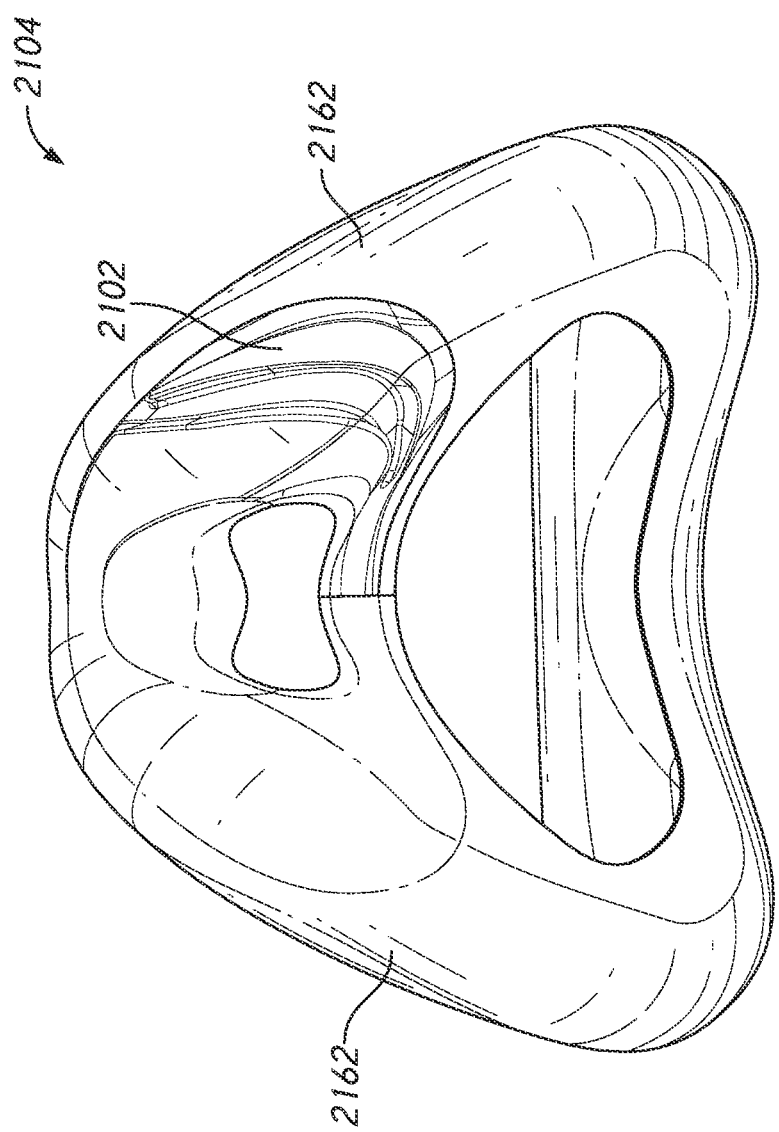
FIG. 14 is a top and rear perspective view of the mask assembly of FIG. 12 illustrating the cut-out region of the mask seal.
Figure 15:
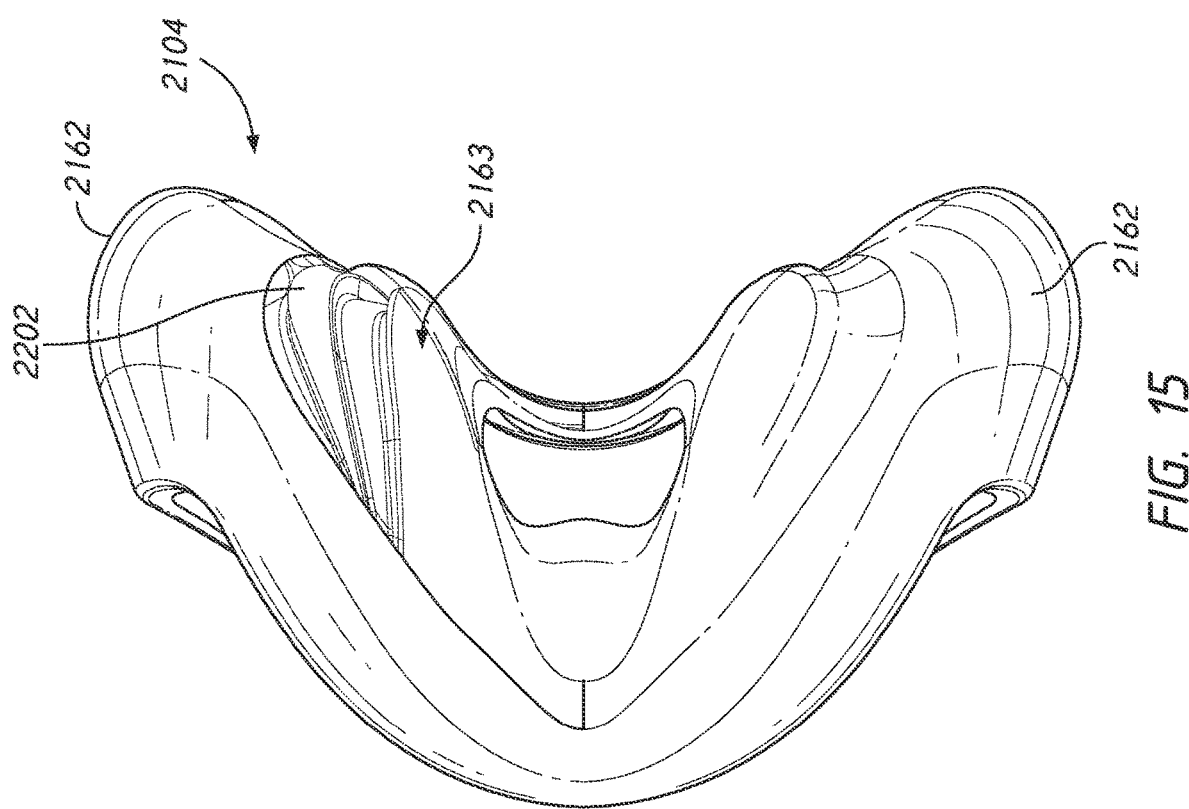
FIG. 15 is a top view of the mask assembly of FIG. 12 illustrating the cut-out region of the mask seal.

For example, FIGS. 10A-10C and 11A-11B illustrate a top view of the mask assembly illustrating the cut-out region 2202 of the mask seal 2104. In this example, a constant lateral force 2400 is applied to a nasal region 2402 of the paddles 2126. In some configurations, the lateral force 2400 is caused by a user's nose being wider than a neutral width of the nasal region 2402 (e.g., when no or minimal lateral force is applied to the nasal region 2402). However, in other configurations not shown, a force can be applied in any direction and/or can be varied. As shown in the illustrated example, the cutout regions 2202 can compress when the force 2400 is applied to the paddles 2126. FIG. 10A illustrates an example configuration when no or little force is applied. As shown, the support structure 2163 includes an inner region 2404 and an outer region 2406, which cooperate to define the cutout regions 2202. In such configurations, the cutout regions 2202 separate the inner region 2404 and the outer region 2406. When no or a small force is being applied to the paddles 2126, outer ends of the inner region 2404 and the outer region 2406 are spaced apart by a gap 2408 of the mask seal 2104. FIG. 10B illustrates a configuration of the mask seal 2104 when the lateral force 2400 is applied to the nasal region of the paddles 2126. As shown in the illustrated configuration, the inner region 2404 compresses towards the outer region 2406 of the cutout regions 2202 In the illustrated configuration, the outer region 2406 remains relatively stationary when the lateral force 2400 is applied to the nasal region of the paddles 2126. As shown in FIG. 10B, a size of the gap 2408 of the mask seal 2104 decreases as the inner region 2404 of the cutout regions 2202 is compressed. As the paddles 2126 are compressed, the inner region 2404 moves towards the outer region 2406. In some configurations, depending on the amount of force that is applied to the nasal region, the inner region 2404 of the cutout regions 2202 does not touch and/or overlap with the outer region 2406. However, as shown in FIG. 10C, the inner region 2404 can touch and/or at least partially overlap with the outer region 2406.

In some configurations, the mask seal 2104 provides flexibility in the nasal sealing surface to cater to various nasal geometries and differently sized nasal regions of users, in particular various nasal widths. In some such configurations, the seal 2104 described herein improves a seal with the lower nasal surfaces of the user by pinching inwardly on the outside of the user's nose.

As illustrated in FIGS. 12-15, the masks seal can include a reduced nasal region width 2410 compared to other mask seals. The reduced nasal region width 2410 can desirably provide a feel of increased positive engagement with the sides of the user's nose. For example, the nasal region width 2410 can be approximately one-half a width of an upper portion of the mask seal 2104. In some configurations, the nasal region width 2410 is about ¼ of a width of an upper portion of the mask seal 2104. In some configurations, the nasal region width 2410 can extend from a center of the mask seal 2104 outwardly towards the outer peripheral portions 2162 of the mask seal 2104 a distance less than a lateral width of the oral opening 2122. In some configurations, the nasal region width 2410 extends from a center of the mask seal 2104 outwardly towards the outer peripheral portions 2162 of the mask seal 2104 a distance about the same as and/or greater than a lateral width of the oral opening 2122. In some configurations, the nasal region width 2410 extends from a center of the mask seal 2104 outwardly to the cutout regions 2202.

In some configurations, a total nasal region width 2412 is approximately 20 mm to 25 mm wide, 25 mm to 30 mm wide, 30 mm to 35 mm wide, 35 mm to 40 mm wide, 40 mm to 45 mm wide, 45 mm to 50 mm wide and/or 50 mm or more wide. Preferably, the total nasal region width 2412 is approximately 40 mm wide.

In some configurations, the reduced total nasal region width 2412 causes increased engagement with the sides of the user's nose when worn. Thus, as described above, the mask seal 2104 can provide a better seal with the user's face. Such configurations can allow the user to feel that the mask seal 2104 is correctly positioned and/or properly sealed with the user's nose. In some configurations, the paddles 2126 of the mask seal 2104 can pinch inwardly on the user's nose by increasing a sealing force applied to the user's nose.

Figure 16:
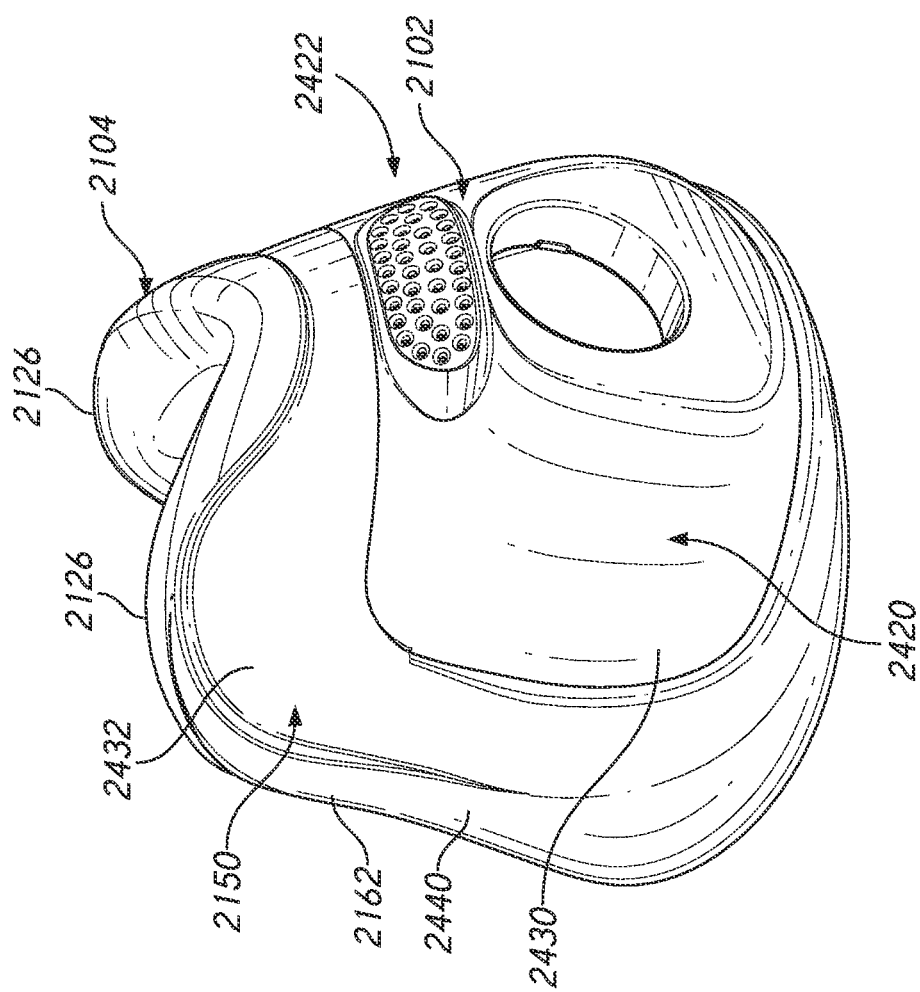
FIG. 16 is a front perspective view of a mask assembly illustrating recessed surfaces of the mask assembly.

In some configurations, the mask assembly includes a front portion 2420. The front portion 2420 can include a recessed front surface 2430 and one or more scalloped lateral sides 2440. For example, FIG. 16 illustrates an example of a mask assembly 2100 including a recessed front surface 2430 formed by the housing or mask shell 2102. The recessed surface 2430 can be positioned on the front of the mask seal 2104 and can be configured to receive the frame 2178. The recessed front surface 2430 can be formed along a portion or an entirety of a perimeter of the housing or mask shell 2102 where it is joined to the seal 2104. In the example shown, the recessed front surface 2430 forms a step in the surface of the front portion 2420. The recessed front surface 2430 generally extends along sides and a lower edge of a perimeter of the housing 2102. In some configurations, the step is tapered in depth along its length such that there is no or little step along an upper edge of the perimeter of the housing 2102, and the seal 2104 is flush with the housing 2102 along the upper edge of the perimeter of the housing 2102.

The depth of the step can be dependent on the size of the seal 2104. For example, the seal 2104 can be provided in a range of sizes to fit users with a range of facial dimensions and facial geometries. In some configurations, the seal 2104 is joined to a single-sized housing 2102. In some configurations, the difference in size of the seal 2104 relative to the housing 2102 determines the depth of the step. In some configurations, the recessed front surface 2430 is recessed at a constant depth or a varying depth. For example, the depth of the recessed front surface 2430 can be constant throughout the entire surface of the recessed front surface 2430. However, in some configurations, upper recessed surfaces 2432 (described in more detail below) are recessed at a depth less than and/or greater than the depth of the remaining area of the recessed front surface 2430.

In some configurations, the front portion 2420 includes an upper recessed surface 2432 formed within the seal 2104. The upper recessed surface 2432 can be positioned at the upper front portion 2150. In the illustrated configuration the upper recessed surface 2432 is positioned along the front side of the paddles 2126. The upper recessed surface 2432 can extend along the outer peripheral portions 2162 of the front side 2422 of the mask seal 2104. The upper recessed surface 2432 can extend rearwardly around the sides of the mask seal 2104. In some configurations, the upper recessed surface 2432 wraps substantially around the outer peripheral portions 2162 of the mask seal 2104. In some configurations, the upper recessed surface 2432 is positioned on only a part of the outer peripheral portions 2162. For example, the upper recessed surface 2432 can extend downwardly approximately half a height of the front side 2422 on each side of the seal 2104. In some configurations, the upper recessed surface 2432 extends downwardly less than half of the front side 2422 and in some instances about ⅓ of the front side 2422.

In some configurations, the upper recessed surface 2432 forms a stepped transition between an upper periphery of the upper front portion 2420 that extends along the curvature of a periphery or an upper edge of the paddles 2126. In some configurations, the stepped transition extends at a constant depth or a varying depth. For example, the depth of the stepped transition can be constant throughout the entire stepped transition between the upper periphery of the upper front portion 2420 and recessed front surface 2430. However, in some configurations, the stepped transition varies. For example, the stepped transition can be tapered. In this arrangement, the depth may be smallest at a lower or lateral extreme of the stepped transition. In some embodiments, however, the depth is smallest at an upper extreme of the stepped transition.

The depth of the stepped transition can depend on a number of factors, including a size of the mask seal. For example, the depth of the taper of the stepped transition can be larger for a larger sized mask seal or smaller for a smaller sized mask seal. In some configurations, the upper front portion 2420 includes a plurality of upper corners. For example, the upper front portion 2420 can include a first upper corner and/or a second upper corner. The plurality of upper corners can be formed on a front portion of the paddles 2126. The plurality of upper corners may define all or a portion of a perimeter of the upper recessed surface 2432 extending along the periphery of the upper front portion 2420.

In some configurations, the depth of the stepped transition and/or the taper of the stepped transition is greater at the plurality of corners compared to a central upper portion positioned generally between upper corners (e.g., the first upper corner and the second upper corner).

In some configurations, the recessed front surface 2430 and/or the upper recessed surface allows the frame 2178 to be inserted into the mask seal 2104. For example, the upper recessed surface 2432 can receive all or a portion of the frame 2178. Thus, in some configurations, the stepped transition of the upper recessed surface 2432 has a maximum depth that is greater than or equal to a thickness of the frame. Similarly, the recessed front surface 2430 can receive all or a portion of the frame 2178. These configurations can advantageously provide a somewhat flush finish that is more aesthetically pleasing to the user. In some configurations, the visual size of the mask seal 2104 may be reduced and/or the amount of material used in the mask seal can be reduced. Thus, in some configurations, the mask seal 2104 is less bulky and/or is less obtrusive (see, for example, FIG. 17) to users.

In some configurations the upper recessed surface 2432 may only be provided in certain seal cushion sizes. For example, the upper recessed surface 2432 could only be provided on certain medium or large-sized mask seals 2104. In some configurations, the upper recessed surface 2432 is provided in certain small or medium-sized mask seals 2104. In some configurations the upper recessed surface 2432 may be present in all sizes of mask seals 2104. The depth of the upper recessed surface 2432 can vary dependent on the size of the mask seal 2104. In some configurations the depth of the upper recessed portion may be substantially the same as a thickness of the frame 2178 for a small and/or medium mask seal 2104, and the depth may be greater than the thickness of the frame 2178 for a large sized mask seal 2104 (e.g., a size larger than the small and/or medium sized mask seal 2104). In such configurations, this may result in the mask seal 2104 hanging over and/or extending beyond the frame 2178. In some configurations, the upper recessed surface 2432 is configured to allow a single-sized frame to be used with a plurality of various-sized mask seals 2104 without the frame 2178 being too large or small for the plurality of mask seals 2104.

Figure 17:
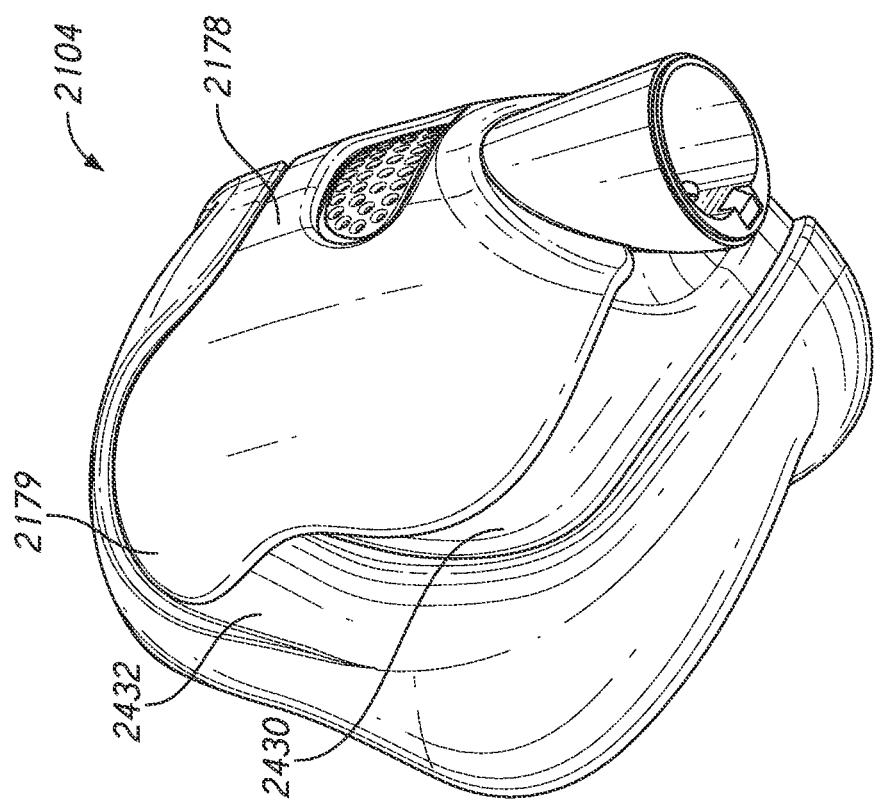
FIG. 17 is a front and side perspective view of the mask assembly of FIG. 16 illustrating the recessed surfaces of the mask assembly and a frame.

In some configurations, the upper recessed surface 2432 provides better support to the nasal sealing surfaces. For example, FIG. 17 shows a frame 2178 and frame paddles 2179 positioned inset and/or within the upper recessed surface 2432. As shown in the illustrated configuration, the frame paddles 2179 can be positioned within the upper recessed surface 2432. In this configuration, an outer surface of the frame paddles 2179 sits flush with the upper recessed surface 2432. This arrangement can provide additional support to the nasal sealing surfaces by providing additional rigidity to the front side 2422 of the mask seal 2104 and paddles 2126. In some configurations, the frame paddles 2179 desirably provide support to the seal paddles 2126. In such configurations, the frame paddles 2179 can help to prevent the seal paddles 2126 from deflecting away from the user's nose in use. In some configurations, this arrangement can help to prevent the frame paddles 2179 from contacting or digging into the user's face if the mask seal 2104 becomes overly deformed. Thus, in some configurations, the recessed front surface 2430 can advantageously allow the mask seal 2104 to maintain its structure over time and can increase the durability of the mask seal 2104. In some configurations, the recessed front surface 2430 allows the use of a single-sized frame 2178 to be implemented with mask seals 2104 having varying sizes. Thus, in some configurations, the recessed front surface 2430 reduces manufacturing costs of the mask assembly.

FIGS. 18A and 18B illustrated an example of a mask seal 2104 including scalloped lateral sides 2440. The scalloped lateral sides 2440 can advantageously reduce the amount of material of the mask seal 2104 and can provide a more aesthetically pleasing or visually smaller mask seal 2104. As shown in the illustrated configuration, an outer wall of the mask seal 2104 transitions smoothly along the outer peripheral portions 2162 of the mask seal 2104. However, in other configurations, the outer peripheral portions 2162 can comprise at least three distinct sections (e.g., an upper portion, a central portion, and a lower portion) and the outer peripheral portions 2162 may not transition smoothly between each section.

In the illustrated configuration, the scalloped lateral sides 2440 form a concave portion along the sides of the mask seal 2104. The scalloped lateral sides 2440 can be positioned below the paddles 2126 along the outer peripheral portions 2162 of the mask seal 2104. In some configurations, the scalloped lateral sides 2440 are positioned at least partially overlapping with a bottom of the paddles 2126. In some configurations, the scalloped lateral sides 2440 are positioned entirely below the paddles 2126. In some configurations, a center 2442 of the concave portion of the scalloped lateral sides 2440 is approximately aligned with a top of the oral opening 2122. In some configurations, the center 2442 of the concave portion is positioned above the oral opening 2122, but below the nasal region 2168. In some configurations the center 2442 of the concave portion is positioned above the nasal region 2168.

In some configurations, the scalloped lateral sides 2440 extend along approximately one half of the outer peripheral portions 2162 of the mask seal 2104. In some configurations, the scalloped lateral sides 2440 extend along approximately ⅛, ¼, ⅓, ¾, or more of the outer peripheral portions 2162 of the mask seal 2104.

As shown in the illustrated configuration, the scalloped lateral sides 2440 can provide additional vertical support for the nasal regions 2168. For example, the scalloped lateral sides 2440 can provide additional support when a lateral force is applied to the nasal region and/or when the pressure within the mask seal 2104 increases. For example, the scalloped lateral sides 2440, among other portions of the mask seal 2104 can advantageously assist in transferring a load from the cheeks to the frame 2178 on the sides of the mask seal 2104, which helps to maintain engagement with the user's face. Thus, the scalloped lateral sides 2440 can provide an improved seal between the user's nose and the mask seal 2104.

FIGS. 19A and 19B illustrate an example of a mask assembly 2100 including the recessed front surface 2430 formed by the housing or mask shell 2102. The recessed front surface 2430 can be positioned on the front of the mask seal 2104 and can receive various configurations of the frame 2178. For example, as shown in FIGS. 19A and 19B, the frame 2178 and the frame paddles 2179 are positioned inset and/or within the upper recessed surface 2432, which can be defined in whole or in part by the seal 2104.

In some configurations, the housing 2102 can include a bias vent 2502. The bias vent 2502 can include a plurality of orifices configured to exhaust air and flush $CO_2$ to reduce the likelihood of rebreathing expired carbon dioxide by the user. While the orifices of the bias vent 2502 are shown exclusively on the housing 2102, in some configurations, the bias vent 2502 can be provided on the mask seal 2104, the elbow 2520 or other conduit connector, or on any combination of the housing 2102, the mask seal 2104, the elbow 2520, or on any other component of the interface assembly or associated breathing circuit. The orifices can have any suitable cross-section and can be cylindrical, hour-glass shaped, tapered in either direction, fully or partially tapered, fully or partially cylindrical, contoured to vary in cross-section or the like. The cross-section of the orifices can increase or decrease exhausted air through the orifices.

In some configurations, the frame 2178 can attach and/or otherwise include an elbow 2520. While FIGS. 19A and 19B show an example of the mask assembly 2100 having an elbow 2520 attached to the frame 2178, in some configurations, the elbow is attached directly to the mask housing 2102 and/or the mask seal 2104, among other mask components. The elbow can be removable and/or permanently attached to the frame 2178 and/or housing 2102. The elbow 2520 can form a non-horizontal connector. For example, the elbow 2520 can include a bend. In some configurations, the elbow 2520 bends at an angle of approximately 10 to 20 degrees, 20 to 30 degrees, 30 to 40 degrees, 40 to 50 degrees, 50 to 60 degrees, 60 to 70 degrees, 70 to 80 degrees, and/or 80 to 90 degrees, among other ranges. Such configurations can desirably reduce the bulkiness of the mask assembly, reduce materials, and/or redirect airflow in a desirable direction. In some configurations, the elbow 2520 is horizontal, vertical, or straight.

The elbow 2520 can include an upper portion and a lower portion. The upper portion and the lower portion can be separated by the bend, as discussed above. The elbow 2520 can include various connection features, such as a frame connection slot 2532, a retention notch 2534, and an inlet connector 2530, among others. The inlet connector 2530 can form the upper portion of the elbow 2520 such that the inlet connector 2530 can connect with an inlet 2510 of the mask housing 2102. The inlet connector 2530 can removably connect the elbow 2520 to the inlet 2510 by snap fit, press fit, interference fit, and/or other fit configurations. Accordingly, in some configurations, the elbow 2520 can be connected to a gas supply conduit (not shown) at one end (e.g., the lower portion) and the inlet connector 2530 positioned at another end (e.g., the upper portion) of the elbow 2520 provides a flow path through which a flow of pressurized gas is provided to the user through the interior chamber 2125 of the mask seal 2104.

Figure 21A:
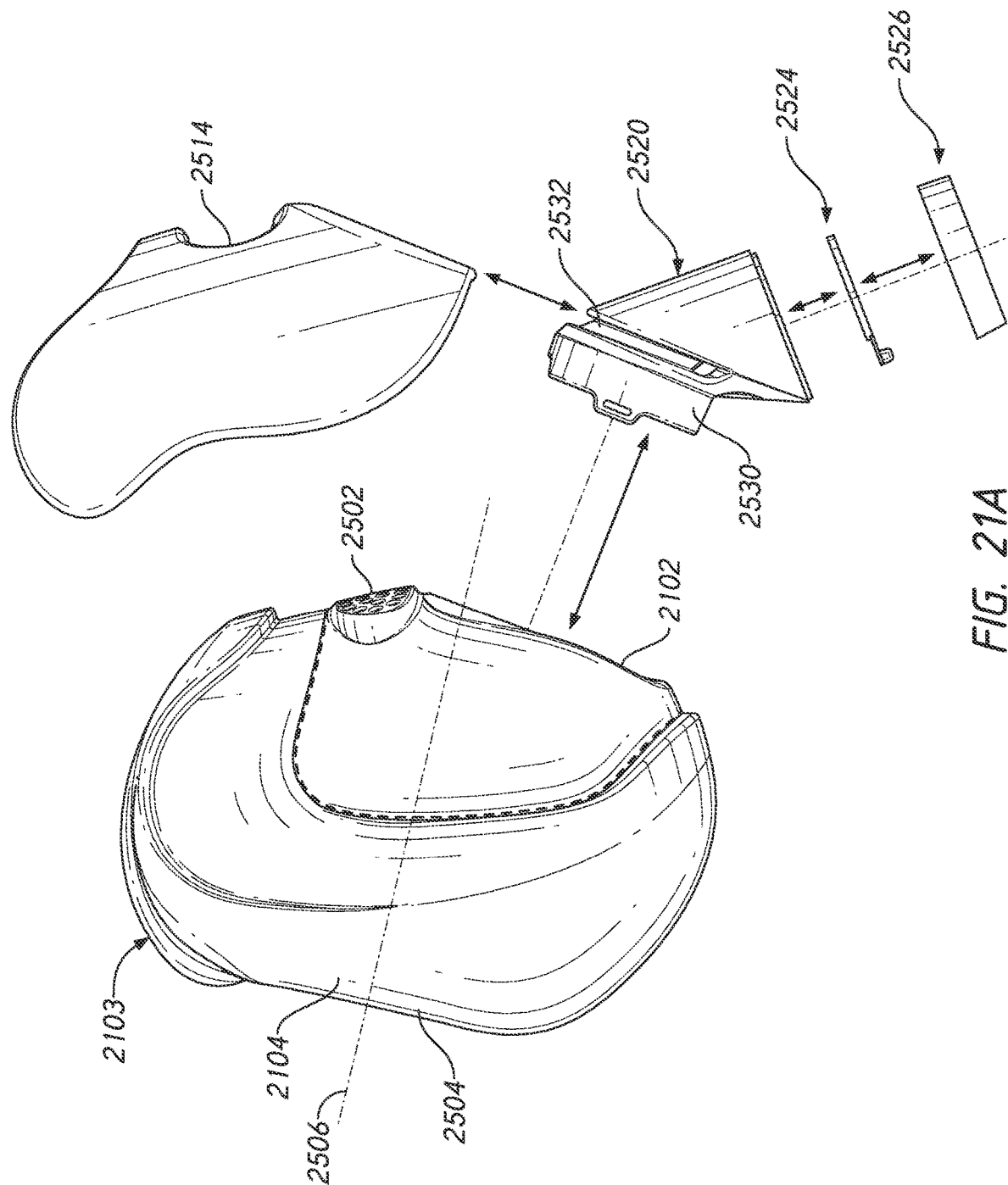
FIG. 21A is an exploded view of the mask assembly of FIG. 19A illustrating an assembly of the mask assembly.
Figure 21B:
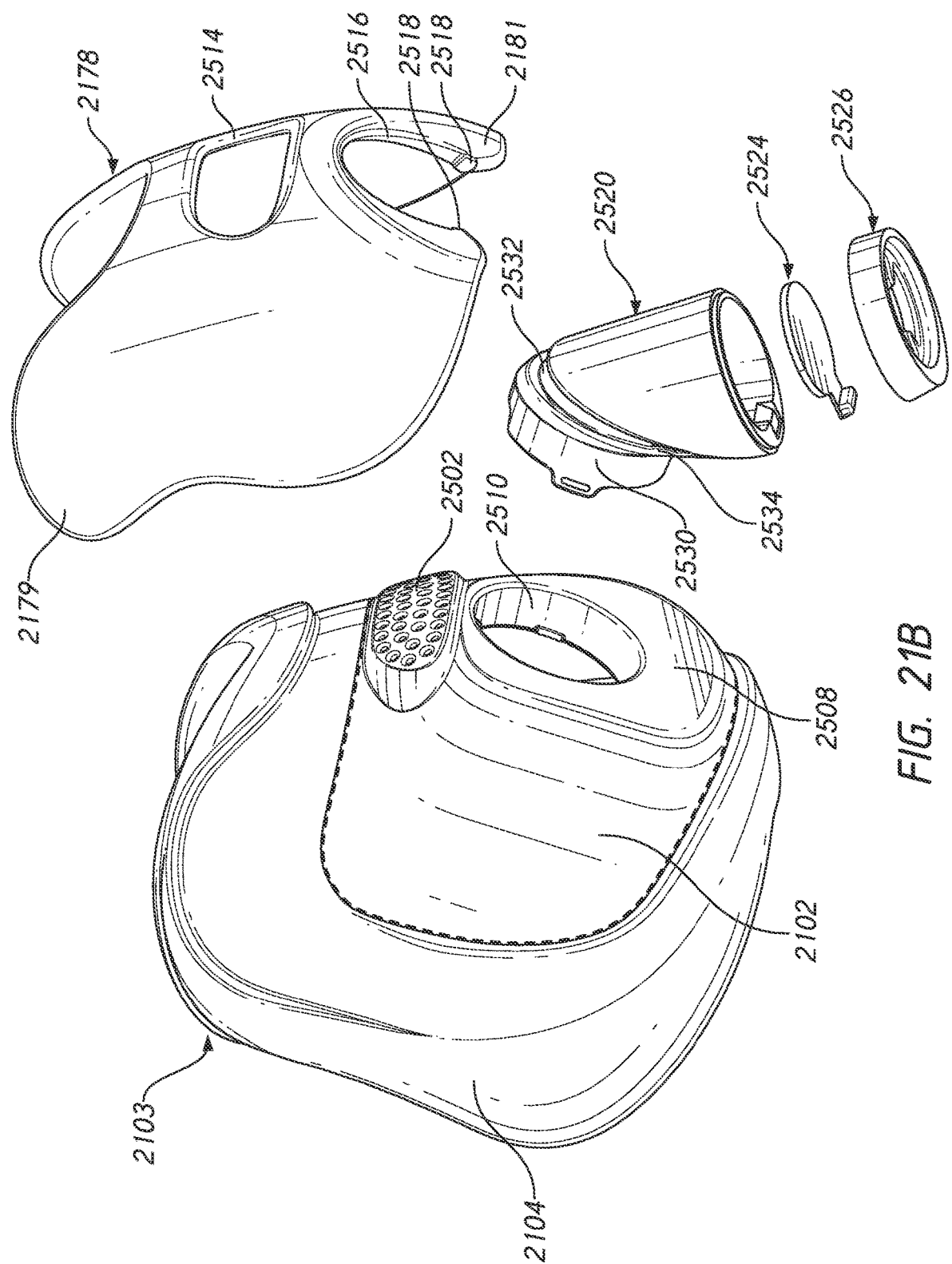
FIG. 21B is an exploded view of the mask assembly of FIG. 19A illustrating an assembly of the mask assembly.
Figure 22B:
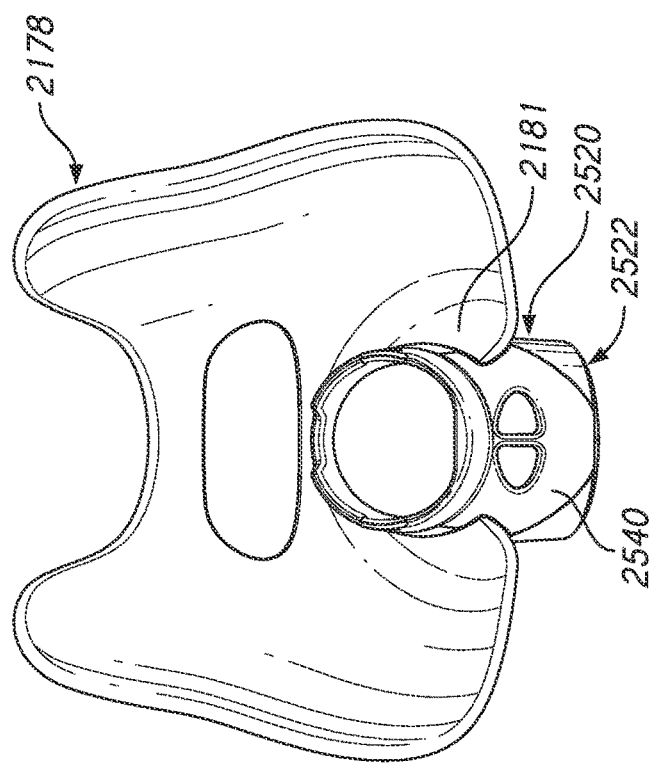
FIG. 22B is a rear view of the mask assembly of FIG. 22A illustrating an assembly of the mask frame.
Figure 22A:
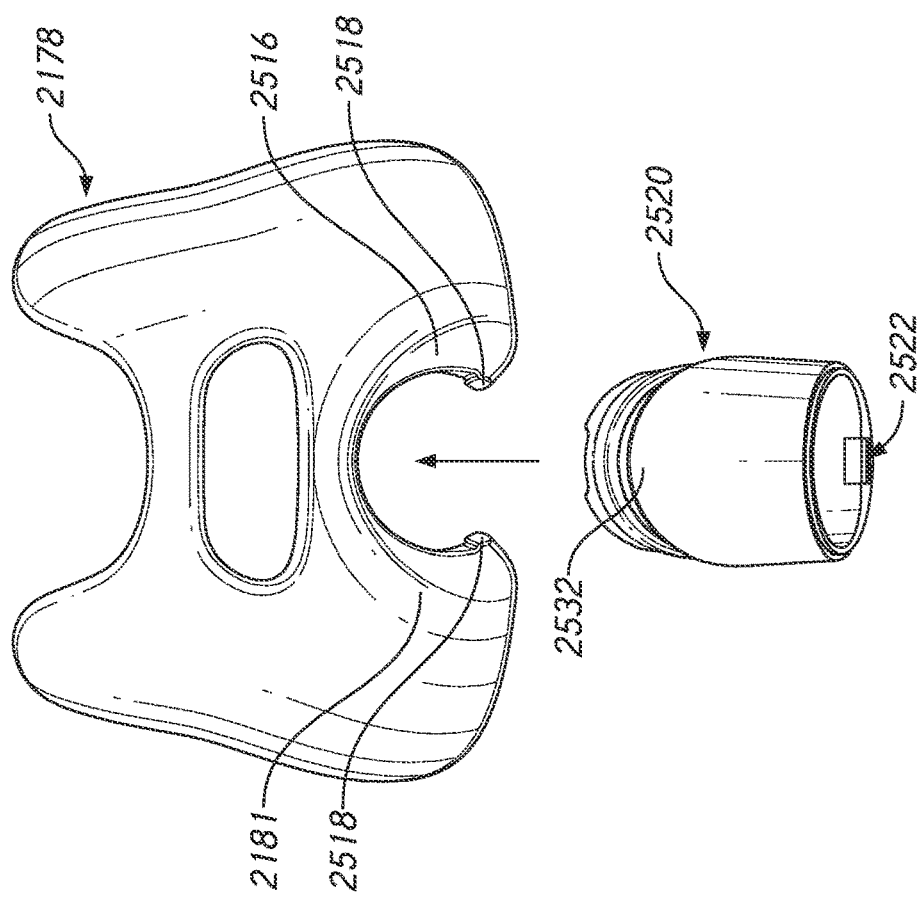
FIG. 22A is a front view of a mask assembly illustrating an assembly of a mask frame.
Figure 25:
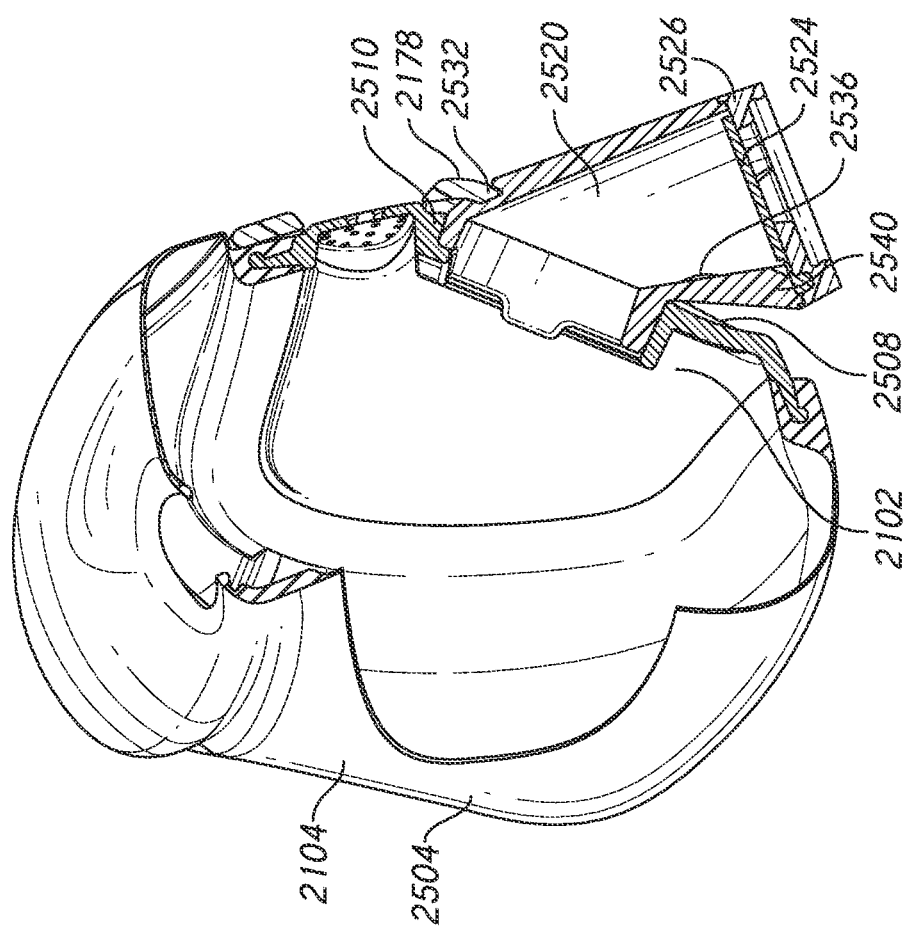
FIG. 25 is a sectional side view of the mask assembly of FIG. 24 illustrating recessed surfaces of the mask assembly.
Figure 26:
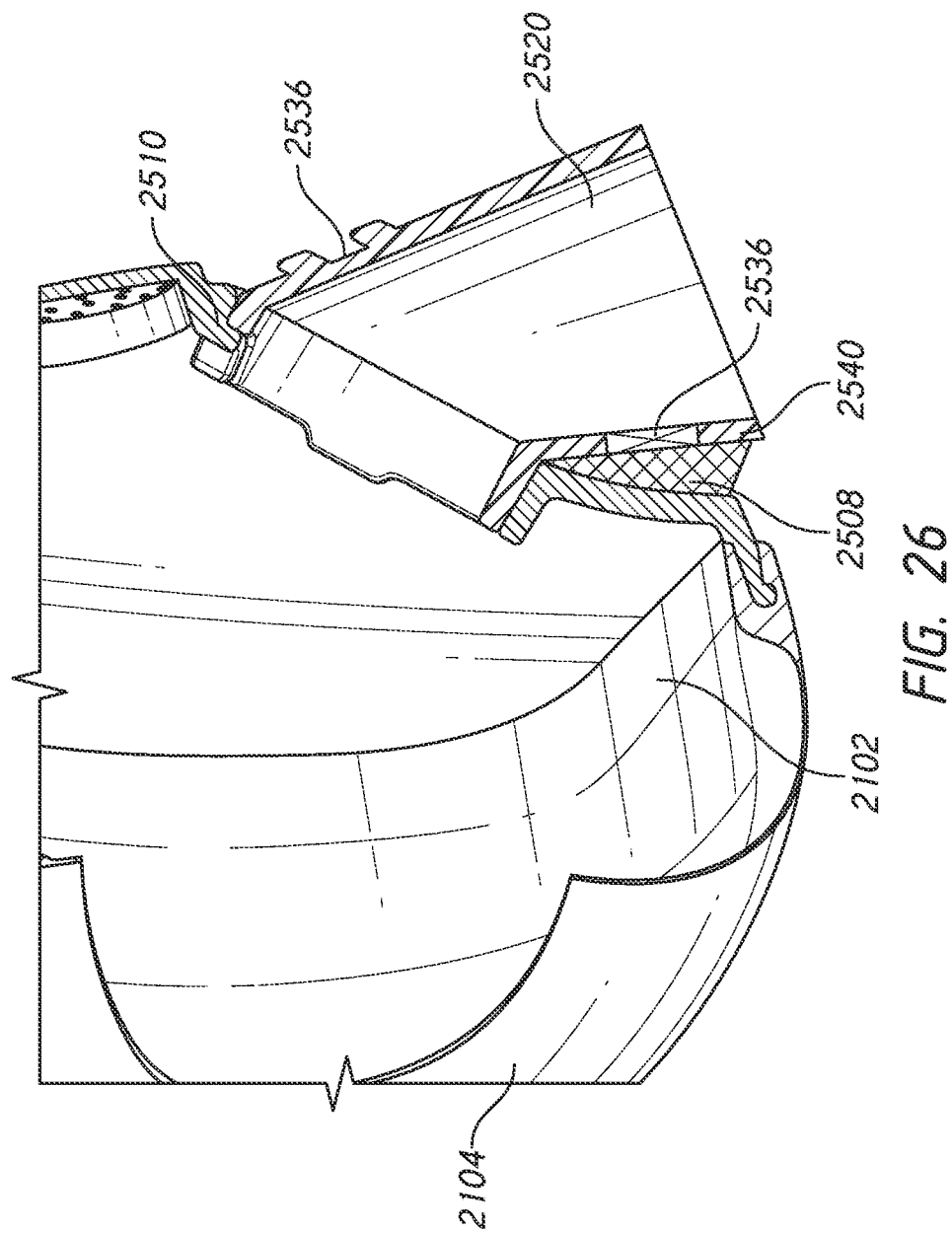
FIG. 26 is a partial sectional side view of a mask assembly illustrating recessed surfaces of the mask assembly.
Figure 28:
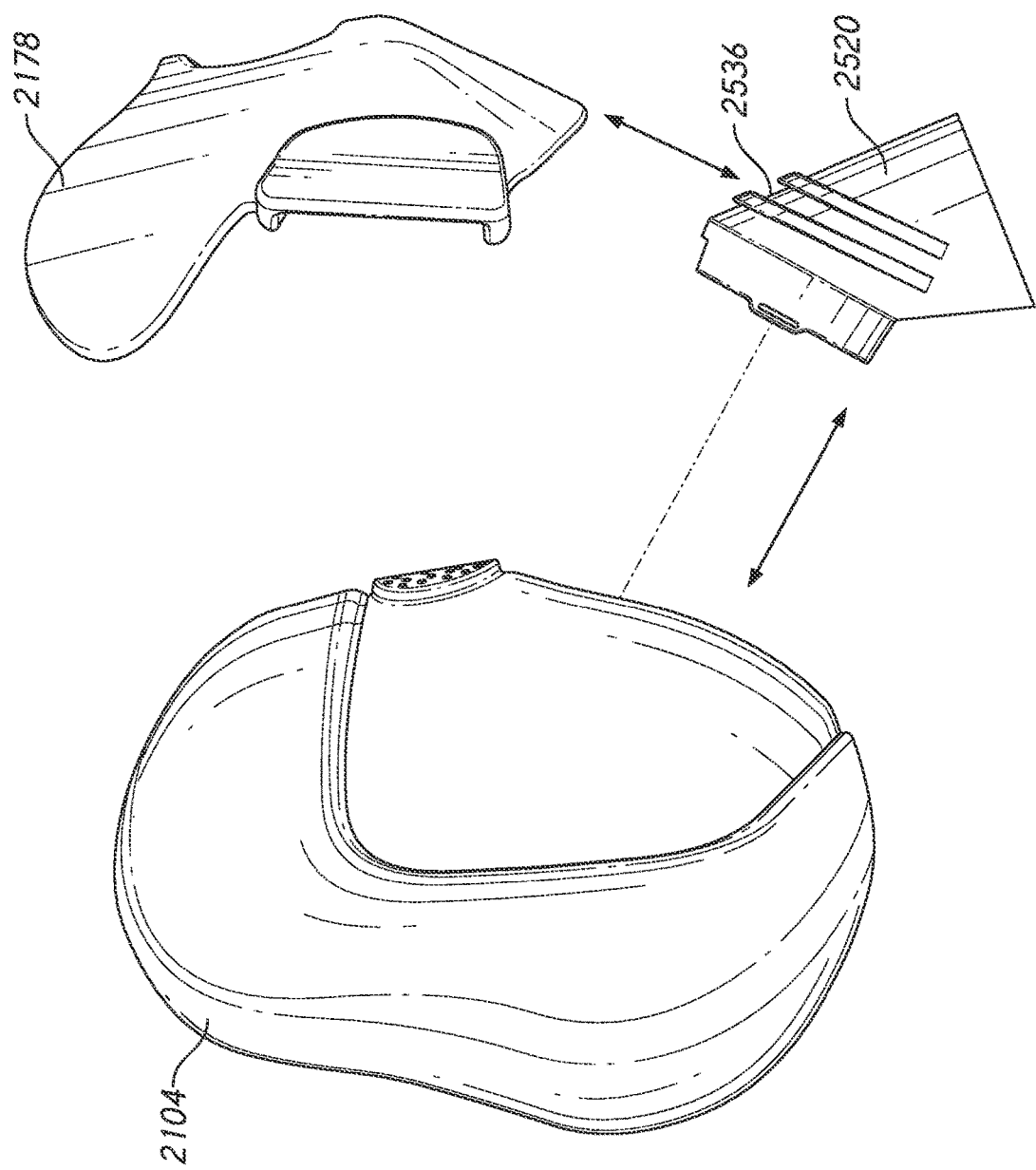
FIG. 28 is an exploded view of a mask assembly illustrating an elbow design of FIG. 26.
Figure 29:
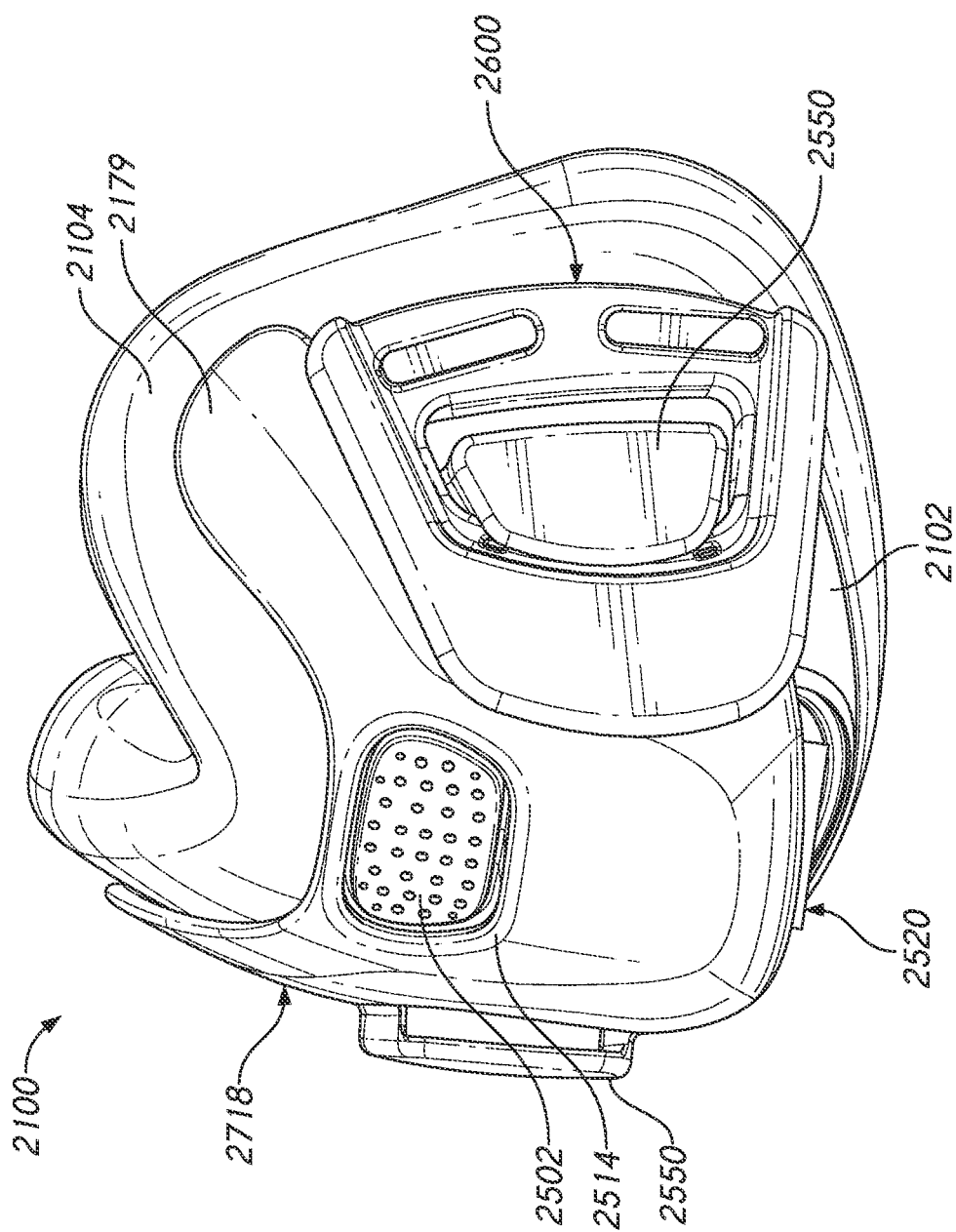
FIG. 29 is a front and side perspective view of a mask assembly illustrating a headgear clip and clip retention features.

The frame connection slot 2532 can be formed by a slot or cut out in the elbow 2520. In some configurations, the frame connection slot 2532 can be formed by a plurality of protrusions, such as ribs extending outwardly from adjacent surface portions of the elbow 2520. For example, as shown in FIGS. 26 and 28, the elbow 2520 includes two ribs extending outwardly from the elbow 2520 to receive and/or retain an elbow connector 2516 of the frame 2178. The frame connection slot 2532 can, as shown in FIGS. 21A and 21B, be positioned offset from an end of the upper portion of the elbow 2520. In some configurations, the frame connection slot 2532 is positioned on the lower portion of the elbow 2520 on one side of the bend. The frame connection slot 2532 can wrap entirely around the elbow 2520. In some configurations, as illustrated, the frame connection slot 2532 extends around only a portion of the elbow 2520.

In some configurations, the elbow 2520 can include an anti-asphyxia (A-A) valve 2522. The A-A valve 2522 can provide a flow path through which ambient air can enter the mask 2100. For example, in some instances if a flow generator fails to provide a supply of gas to the mask, the valve 2522 provides the user with access to ambient air.

The A-A valve 2522 can include a valve flap 2524, a valve seat or retainer 2526, and a valve port 2536, among other components. The valve port 2536 can include one or more openings to provide a path for air to flow from the atmosphere to the interior chamber 2125 of the mask seal 2104. The valve port 2536 can be positioned at one end of the elbow 2520. For example, the valve port 2536 can be positioned on a rear side 2540 of a lower portion of the elbow 2520 such that the valve port 2536 forms an opening facing generally towards the mask seal 2104 or a front concave surface 2508 of the mask seal 2104 (as discussed below). In some configurations, the valve port 2536 is positioned below the inlet connector 2530 of the elbow 2520. In some configurations, the valve port 2536 is generally parallel to the front concave surface 2508 of the mask seal 2104. In some configurations, the valve port 2536 is angled downwardly towards the front concave surface 2508 of the mask seal 2104.

The valve flap 2524 can be positioned to fit within the elbow 2520 and/or within at least a portion of the valve seat 2526. The valve flap 2524 can open and close the valve port 2536 to allow air to flow through the valve port 2536. For example, when a flow generator provides airflow to the user through the mask seal 2104, the valve flap 2524 is opened relative to the valve seat 2526, thereby closing the valve port 2536. When a flow generator does not provide airflow to the mask seal 2104, the valve flap 2524 is closed relative to the valve seat 2526 and the valve port 2536 is opened to allow the user in inhale ambient air through the valve port 2536. The valve seat 2526 can support the valve flap 2524 in an operable position. In some configurations, the valve seat 2526 defines a stop that prevents the valve flap 2524 from inverting or extending downwardly out of the elbow 2520. As described in more detail below, the elbow 2520, including the valve 2522 in some configurations, can be positioned forward of a concave front surface of the mask seal 2104.

FIG. 20 illustrates an example frame 2178 that can be implemented in the mask assembly 2100 and can be connected to embodiments of the housing 2102 described herein. The frame 2178 can be attached to the housing 2102 through various arrangements. For example, the frame 2178 can slide into the mask seal 2104, and/or attach to the mask seal 2104 through a snap fit or press fit, among other suitable attachment arrangements. As discussed above, the frame 2178 can fit into the front recessed surface 2430, including the upper recessed surface 2432, of the mask seal 2104. In some configurations, the frame 2178 is configured to be repeatedly removable from the mask seal 2104 to allow one or both of the mask seal 2104 and the frame 2178 to be interchangeable. In some configurations, however, the frame 2178 can be permanently attached to the mask seal 2104.

In some configurations, the frame 2178 can include at least one headgear connector 2512, a vent aperture 2514, and/or an elbow connector 2516, among other features or components. The at least one headgear connector 2512 can connect to and/or receive headgear. In some configurations, the headgear connector 2512 can be formed in the frame 2178. For example, the frame 2178 can include one, two, three, four, five, and/or six or more headgear connectors 2512. As shown in FIG. 20, the illustrated frame 2178 includes a pair of opposing headgear connectors 2512, which form slots to each receive at least a portion of headgear, such as a connector clip of the headgear.

The at least one headgear connector 2512 can be positioned along a front side of the frame 2178. For example, the at least one headgear connector 2512 can extend outwardly (e.g., forwardly and/or laterally outward) from the front side of the frame 2178 and at least partially define a boundary of an aperture in the frame 2178 for connecting headgear. As shown in FIG. 20, the headgear connector 2512 can extend along only a portion of the front side of the frame 2178 in the height and/or width direction. The headgear connector 2512 can extend vertically or can be angled between a top side of the frame 2178 and a lower side of the frame 2178. In the illustrated arrangement, the upper ends of the headgear connectors 2512 are positioned forward and/or inward relative to the lower ends of the headgear connectors 2512. The headgear connector 2512 can be positioned at least partially below each of the paddles 2126 and/or a nasal region of the frame 2178. In some configurations, the headgear connector 2512 can be positioned on the housing 2102 or other component of the mask assembly 2100.

As shown in FIG. 20, the frame 2178 can include a vent aperture 2514 shaped to accommodate or receive the bias vent 2502. Accordingly, in some configurations, the vent aperture 2514 aligns with the bias vent 2502. Some arrangements can advantageously allow exhausted air, as discussed above, to pass through the frame 2178 to the atmosphere. For example, the bias vent 2502 can preferably be provided in the housing 2102 and communicate with or align with any opening in the frame 2178 and/or headgear. In some configurations, the bias vent 2502 is located within at least a portion of the housing 2102 not covered by the frame 2178 or a space defined between the frame 2178 and the housing 2102. In some configurations, the bias vent 2502 is at least partially covered by the frame 2178. Such arrangements can affect the flow rate if exhausted air contacts the frame 2178.

In some configurations, when the frame 2178 is connected to the mask seal 2104, the bias vent 2502 can extend at least partially through the vent aperture 2514 of the frame 2178 (see for example, FIGS. 19A and 19B). In some configurations, the bias vent 2502 is positioned flush with the frame 2178 when the bias vent 2502 is positioned within the vent aperture 2514.

In some configurations, the frame 2178 can include the elbow connector 2516. The elbow connector 2516 can receive and/or connect to the elbow 2520, as shown in FIGS. 22A-23B. The elbow connector 2516 can be defined by or comprise a cut-out located on a lower edge of the frame 2178 that can be configured to receive at least a portion of the elbow 2520. For example, the cut-out of the elbow connector 2516 can connect to the elbow 2520 such that the frame 2178 fits into the frame connection slot 2532 of the elbow 2520.

In some configurations, the elbow connector 2516 can connect to the elbow 2520 by a snap fit, press fit, interference fit, and/or other fit configurations. For example, the elbow connector 2516 can preferably include a pair of retention bumps 2518. The retention bumps 2518 can be positioned opposite from one another on lower corners of the elbow connector 2516. The retention bumps 2518 can engage with a corresponding connection feature of the elbow 2520, such as retention notches 2534. The retention notches 2534 can be positioned at lower ends of the frame connection slot 2532 of the elbow 2520. In some configurations, the frame 2178 can be permanently connected to the elbow 2520 by connecting means, such as welding, overmoulding and/or adhesives, among others.

As described above, the elbow 2520 can connect to the frame 2178. In some configurations, as shown in FIGS. 22A-23B, the elbow 2520 can connect to the frame 2178 before the frame 2178 is connected to the mask seal 2104. For example, the elbow can slide into the cut-out of the elbow connector 2516 such that the elbow connector 2516 aligns with the frame connection slot 2532. When the elbow connector 2516 slides into the frame connection slot 2532, the retention bumps 2518 can align with the corresponding retention notches 2534. Accordingly, the elbow 2520 can be retained by the frame 2178 to form a sub-assembly that is then coupled to the mask seal 2104.

In some configurations, as shown in FIGS. 21A and 21B, for example, the elbow 2520 connects directly to the inlet 2510 of the housing 2102 via the inlet connector 2530 of the elbow 2520. In some configurations, the elbow 2520 can connect to the housing 2102 before or after the frame 2178 is connected to the elbow 2520. However, in other configurations, the elbow 2520 must first be connected to the frame 2178 and then the elbow 2520/frame 2178 sub-assembly can be connected to the housing 2102. In some configurations, the elbow 2520 can provide a connection between the housing 2102 and the frame 2178. For example, in such configurations, the frame 2178 may not connect to the housing 2102 without the connection provided by the elbow 2520. In some configurations, the elbow connects and/or disconnects from the housing 2102 in a direction that is angled downward from a plane 2506 that is approximately perpendicular with a sealing surface 2504 of the mask seal 2104. For example, the plane 2506 can be substantially perpendicular to the direction the elbow 2520 is connected to the frame 2178. In some configurations, the plane 2506 can be substantially perpendicular to the direction the frame 2178 is connected to elbow 2520. The elbow 2520 can be removably attached to the housing 2102 by a number of connection arrangements, such as a snap fit arrangement.

When the elbow 2520 is connected to the housing 2102, the elbow 2520 may be non-rotatable. For example, the frame 2178 may not be able to rotate relative to the housing 2102 when the frame 2178, elbow 2520, and housing 2102 are assembled. In some configurations, the connection arrangement between the housing 2102 and the elbow 2520 advantageously allows hose drag forces generated by the CPAP hose to be isolated from the mask. In such configurations, a flexible conduit (not shown) can form an intermediate component that connects the CPAP hose to the elbow 2520. In some configurations, the connection arrangement between the housing 2102 and the elbow 2520 is desirably angled to provide a lower profile mask assembly 2100 that is less obtrusive for users to wear. As such, the elbow 2520 may not extend as far from the user's face when worn compared to traditional mask assemblies. Such configurations can reduce the moment arm caused by the elbow 2520 and potential hose drag on the mask assembly 2100.

Figure 24:
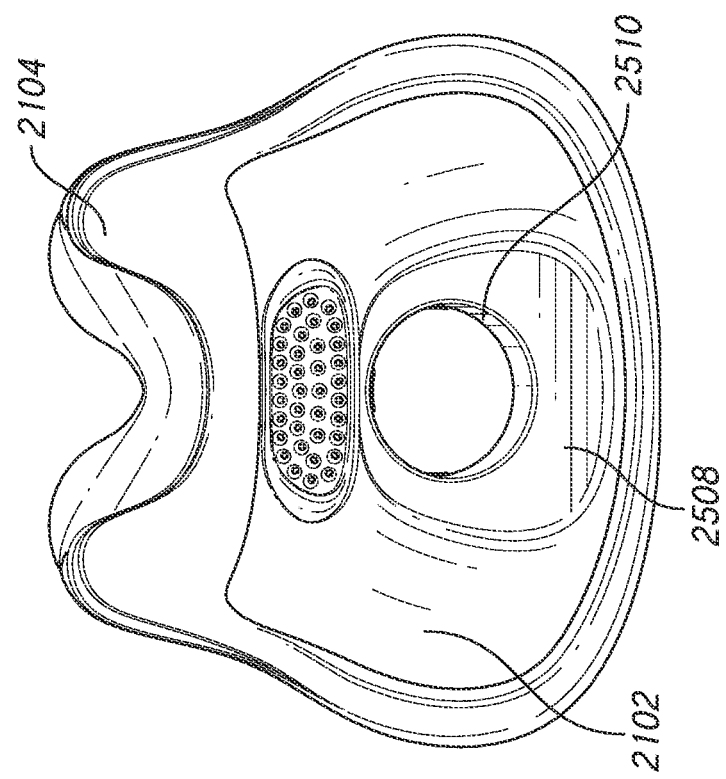
FIG. 24 is a front view of a mask assembly illustrating recessed surfaces of the mask assembly.

In some configurations, the housing 2102 includes a front concave surface 2508 that at least partially surrounds the inlet 2510 (see, for example, FIGS. 21B and 24). For example, the front concave surface 2508 can be offset relative to the inlet 2510 such that a portion of the front concave surface 2508 below the inlet 2510 is larger than a portion of the front concave surface 2508 above the inlet 2510. In some configurations, the area of the portion of the front concave surface 2508 below a lowermost point of the inlet 2510 is at least two times, three times, four times, and/or five times larger than the area of the portion of the front concave surface 2508 above a center of the inlet 2510. In some configurations, the area of the portion of the front concave surface below the inlet 2510 is larger than the portion of the front concave surface to the sides of the inlet 2510.

The front concave surface can advantageously assist in aligning the mask assembly 2100 such that the front concave surface directs the elbow 2520 and/or the frame 2178 into the inlet 2510 of the housing 2102 during assembly.

Figure 27:
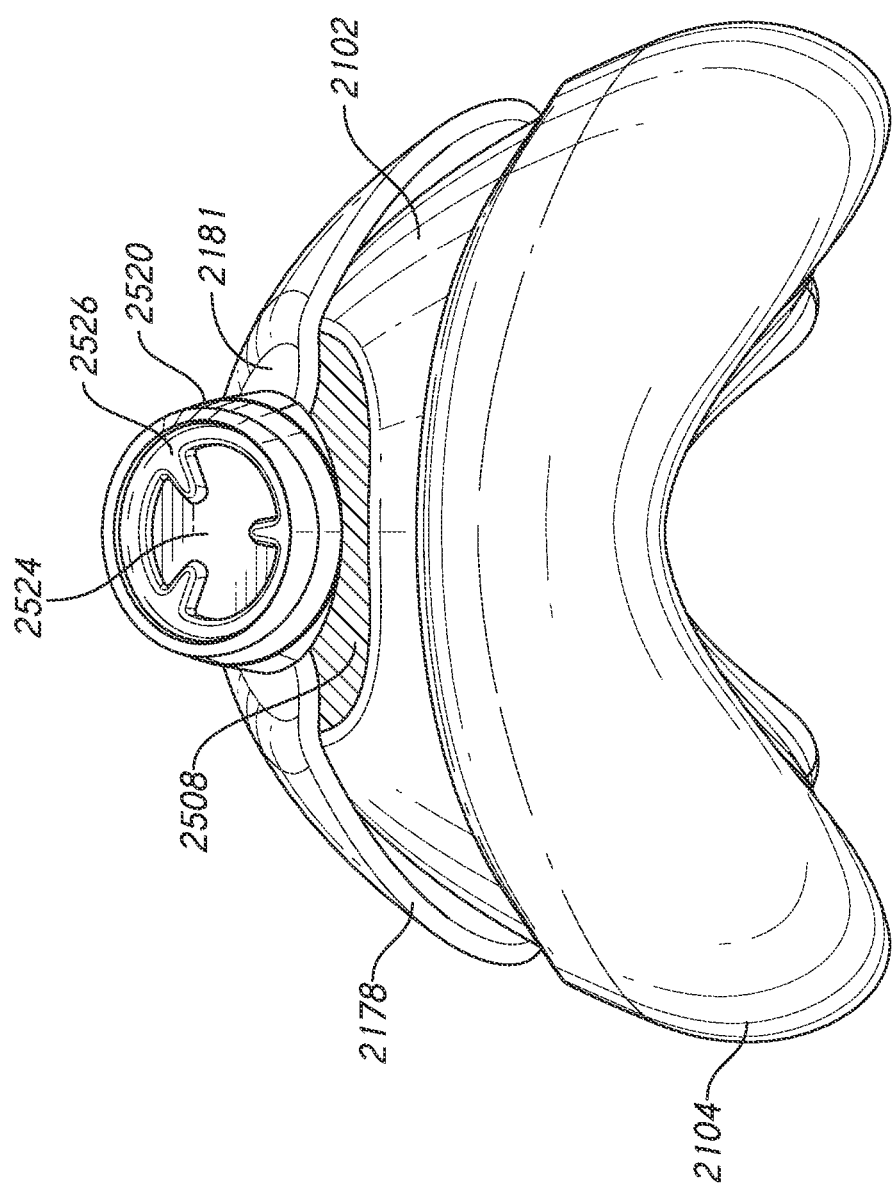
FIG. 27 is a bottom view of a mask assembly illustrating recessed surfaces of the mask assembly.

When assembled, as shown in FIGS. 26-28, for example, the concave surface 2508 is spaced away from a rear side 2540 of the elbow 2520. Accordingly, a gap is formed between the rear side 2540 of the elbow 2520 or an internal surface of the frame 2178 on one side and the housing 2102 on the other side. In some configurations, the gap provides a flow path for air to flow in and out of the interior mask breathing chamber when the valve port 2536 is in the opened position. As shown in FIGS. 26 and 27, for example, the gap has a cross-sectional area that is greater than an area of the valve port 2536. Thus, in some configurations, the flow path through the valve port 2536 defines the smallest area of the flow path from the ambient air, through the gap, the valve port 2536 and into the interior of the elbow 2520. This arrangement can desirably ensure that airflow through the A-A valve is not restricted. Thus, this arrangement can allow ample ambient air to flow into the interior mask breathing chamber and $CO_2$ to be adequately flushed from the interior mask breathing chamber, thereby preventing a restriction in airflow.

In some configurations, the front concave surface 2508 can desirably diffuse airflow from the valve port 2536 away from the user. For example, air can flow through the valve port 2536 towards the front concave surface 2508 such that the air disperses laterally along the front concave surface 2508 and/or reflects off of the front concave surface 2508 and out of the gap formed between the elbow and housing 2102 away from the user to the atmosphere.

In some configurations, this arrangement allows the elbow 2520 to be closer to the user's face in use than typical mask assemblies. For example, the front concave surface 2508 can reduce a depth of the housing 2102 and cause the inlet 2510 to be positioned closer to the sealing surfaces 2504 of the mask seal 2104. At the same time, this arrangement can allow for a sufficient amount of airflow through the valve port 2536.

Similarly, the elbow 2520 can be positioned at least partially within a space defined by the front concave surface 2508 of the housing 2102. Arrangements described herein can allow the elbow to include a wall (e.g., the rear side 2540) to be angled downwardly relative to a portion of the elbow 2520 (e.g., the inlet connector 2530) in connection with the housing 2102. Accordingly, such arrangements may reduce the distance the elbow 2520 extends outwardly away from the housing 2102.

By reducing, relative to arrangements without a front concave surface 2508, or minimizing the distance the elbow 2520 extends outwardly away from the housing 2102, arrangements described herein may desirably reduce hose drag on the mask assembly 2100 caused by the CPAP hose, as discussed above. Excessive hose drag may undesirably cause the mask seal 2104 to disengage from the user's face when worn, resulting in a partial or total loss of therapy. Generally, hose drag forces can be counteracted by headgear, which includes headgear straps to maintain an engagement between the mask assembly 2100 and the user's face with a sufficient amount of force. However, if larger hose drag forces are caused by excess material and by the elbow extending too far away from the mask housing 2102, forces applied by the headgear straps may cause discomfort to the user. Accordingly, the arrangements described herein may advantageously reduce discomfort to the user by limiting excessive forces applied to the user by the headgear straps and/or by reducing or minimizing hose drag forces.

In some configurations, the arrangements described herein can reduce the moment arm applied to the elbow 2520, as discussed above. Similarly, the front concave surface 2508 can minimize the overall size of the housing 2102 or mask assembly 2100 by providing a less obtrusive mask assembly.

As shown in at least FIGS. 21B-23B and 27, the frame 2178 includes a shielding surface 2181. The shielding surface 2181 surrounds the elbow connector 2516 and forms a front boundary of a flow path formed between the frame 2178 and the front concave surface 2508 of the housing 2102. The shielding surface 2181 can be formed by a truncated or concave portion on the front surface of the frame 2178. In some configurations, the shielding surface 2181 is offset from the front concave surface 2508 of the housing 2102 when the frame 2178 is connected to the housing 2102. For example, the shielding surface 2181 can be planar and positioned substantially parallel to the concave surface 2508 of the housing 2102 when the frame 2178 and the housing 2102 are assembled. Such an arrangement can advantageously reduce an overall size of the mask assembly 2100 to allow the mask assembly 2100 to be less obtrusive to the user, and provide sufficient support to the elbow 2520. This arrangement can help to diffuse and/or direct airflow through and/or out of the valve port 2536.

FIGS. 29-33E illustrate configurations of the mask assembly 2100. For example, the mask assembly 2100 can include a full-face mask that forms a seal under at least a portion of the user's nose and/or around at least a portion of the user's mouth. As shown in FIGS. 29-33E, the mask assembly 2100 can include a mask seal 2104, a housing 2102, a frame 2178, at least one headgear clip 2600, and an elbow 2520 or other type of inlet conduit connector.

In some configurations, the mask seal 2104 may be permanently joined or coupled to the housing 2102, for example, by over-moulding. The housing 2102 can be positioned forward of the mask seal 2104 and, alone or together with the seal 2104, can define a breathing chamber about at least a portion of the user's mouth and/or nose (e.g., the user's nostrils). In some configurations, the housing 2102 can include a bias vent 2502 as described herein.

Figure 5:
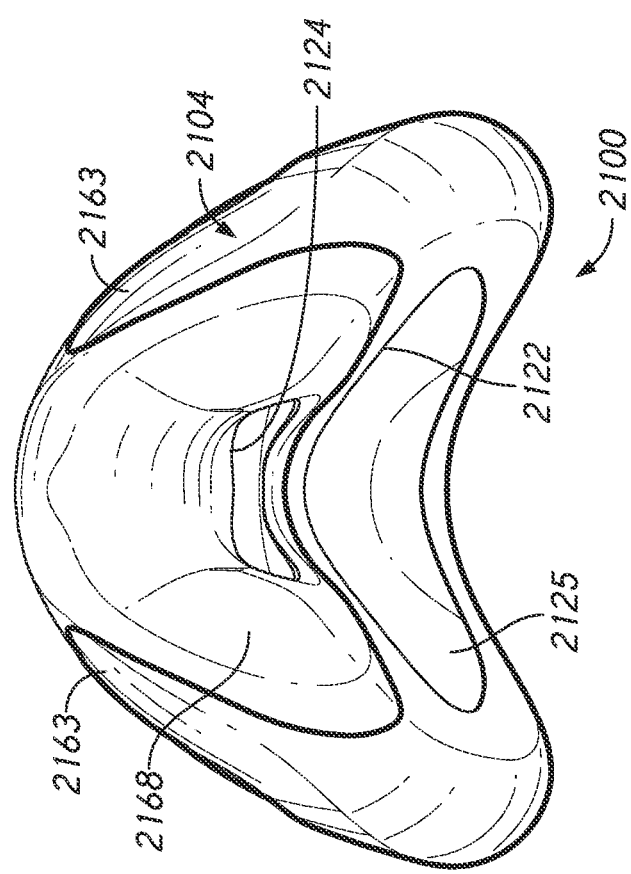
FIG. 5 is a rear view of the mask assembly of FIG. 4 illustrating a thickened region of a mask seal of the mask assembly.

As described above, the mask assembly 2100 can be engaged with or otherwise supported by the frame 2178 that allows for a connection to a head strap or headgear 2180 (see FIG. 1) of any suitable arrangement. In some configurations, the head strap or headgear 2180 could be coupled directly to at least a portion of the mask assembly 2100 and/or the frame 2178. For example, the frame 2178 can include at least one clip retention feature 2550. Preferably, the frame 2178 can include a pair of clip retention features 2550 positioned on opposite lateral sides of the frame 2178. For example, the clip retention features 2550 can be positioned lateral of a center portion of the frame 2178. The frame 2178 may include frame paddles 2179 to support the paddles 2126 of the mask seal 2104. In some configurations, the frame 2178 can include a vent aperture 2514 through which the bias vent 2502 can vent exhaust from an interior chamber 2125 (see FIG. 5).

In some configurations, the mask assembly 2100 includes at least one headgear clip 2600. Preferably the mask assembly 2100 can include a pair of headgear clips 2600. The headgear clips 2600 can connect to the clip retention features 2550 on opposing sides of the mask frame 2178. The headgear clips 2600, as described in more detail below, can provide a connection between at least a portion of the headgear 2180, such as headgear straps, and the frame 2178.

In some configurations, the elbow 2520 can be attached to the housing 2102, frame 2178 or otherwise supported and adapted to communicate with an interior chamber 2125 of the mask assembly 2100. The elbow 2520, as described herein, can connect to an air supply conduit to deliver a supply of pressurized air, for example, to the interior chamber 2125. Together, the frame 2178 and the headgear 2180 can support the mask assembly 2100 in place on the user's face.

Figures 30A, 30B:
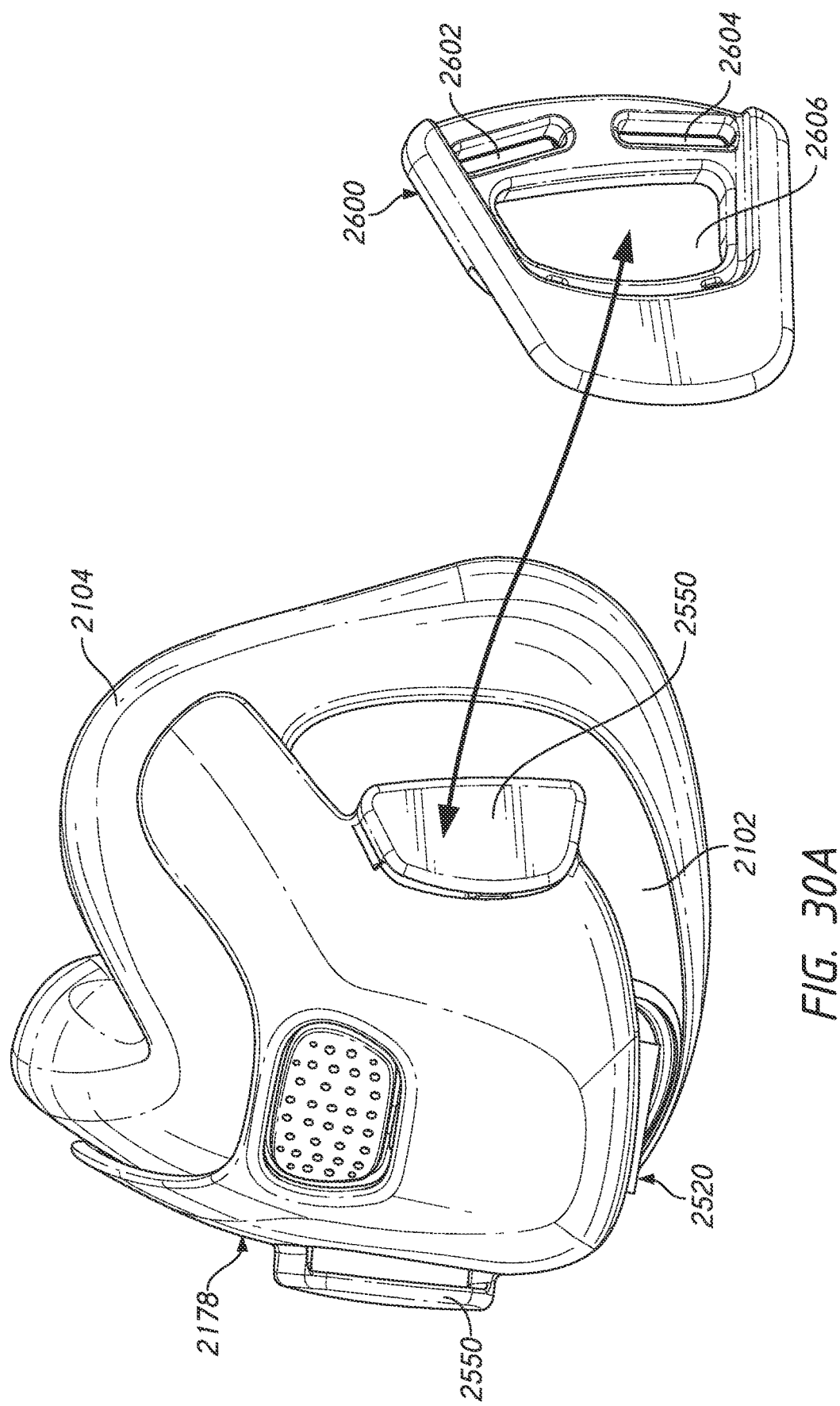
FIG. 30A is a front and side perspective view of the mask assembly of FIG. 29 illustrating clip retention features.
FIG. 30B is a front and side perspective view of a headgear clip of the mask assembly of FIG. 29.

FIGS. 30A and 30B illustrate a configuration of the mask assembly 2100 showing clip retention features 2550 and a headgear clip 2600. In some configurations, as shown in FIGS. 30A and 30B, the headgear clips 2600 can be removably connected to the frame 2178. For example, the headgear clips 2600 can removably clip and/or snap onto, or otherwise attach to the clip retention features 2550 of the frame 2178. In some configurations, the headgear clips 2600 can adjustably attach to the headgear 2180. For example, the headgear clip 2600 can include an aperture 2606 that can fit over the corresponding retention feature 2550 of the frame 2178 and/or slide in a rearward direction or towards the user's face when worn such that the clip retention feature 2550 catches the headgear clip 2600.

For example, FIG. 30B illustrates an example of the headgear clip 2600. The headgear clip 2600 can include at least one strap slot, such as an upper strap slot 2602 and a lower strap slot 2604. The headgear 2180 can include at least one headgear strap to connect to each of the upper and lower strap slots 2602, 2604. For example, the headgear 2180 (as shown in FIG. 1) can include an upper strap that connects to the upper strap slot 2602 and a lower strap that connects to the lower strap slot 2604. In some configurations, the headgear straps can be adjustably attached to the upper and lower strap slots 2602, 2604 of the headgear clip 2600.

FIGS. 31A and 31B show additional examples of the mask assembly 2100 including the mask seal 2104 connected to the mask frame 2178 and the elbow 2520. Advantageously, the headgear clips 2600 of the mask assembly 2100 can connect at least one, and/or preferably two headgear straps in a single action. This configuration can allow various components of the interface assembly, such as the frame 2178, the headgear clips 2600, and the headgear 2180 to be easily assembled and/or disassembled. In such configurations, the user may have limited and/or restricted visibility when assembling and/or disassembling the interface assembly. In some configurations, the arrangements described herein can allow the user to assemble and/or disassemble the interface assembly with one hand. As described herein, the headgear clips 2600 and/or the frame 2178 can provide various features to direct the headgear 2180 to the frame 2178 such that the headgear 2180 and/or headgear clips 2600 are properly positioned within the interface assembly during assembly and/or the interface assembly does not inadvertently disconnect in use.

Figure 32A:
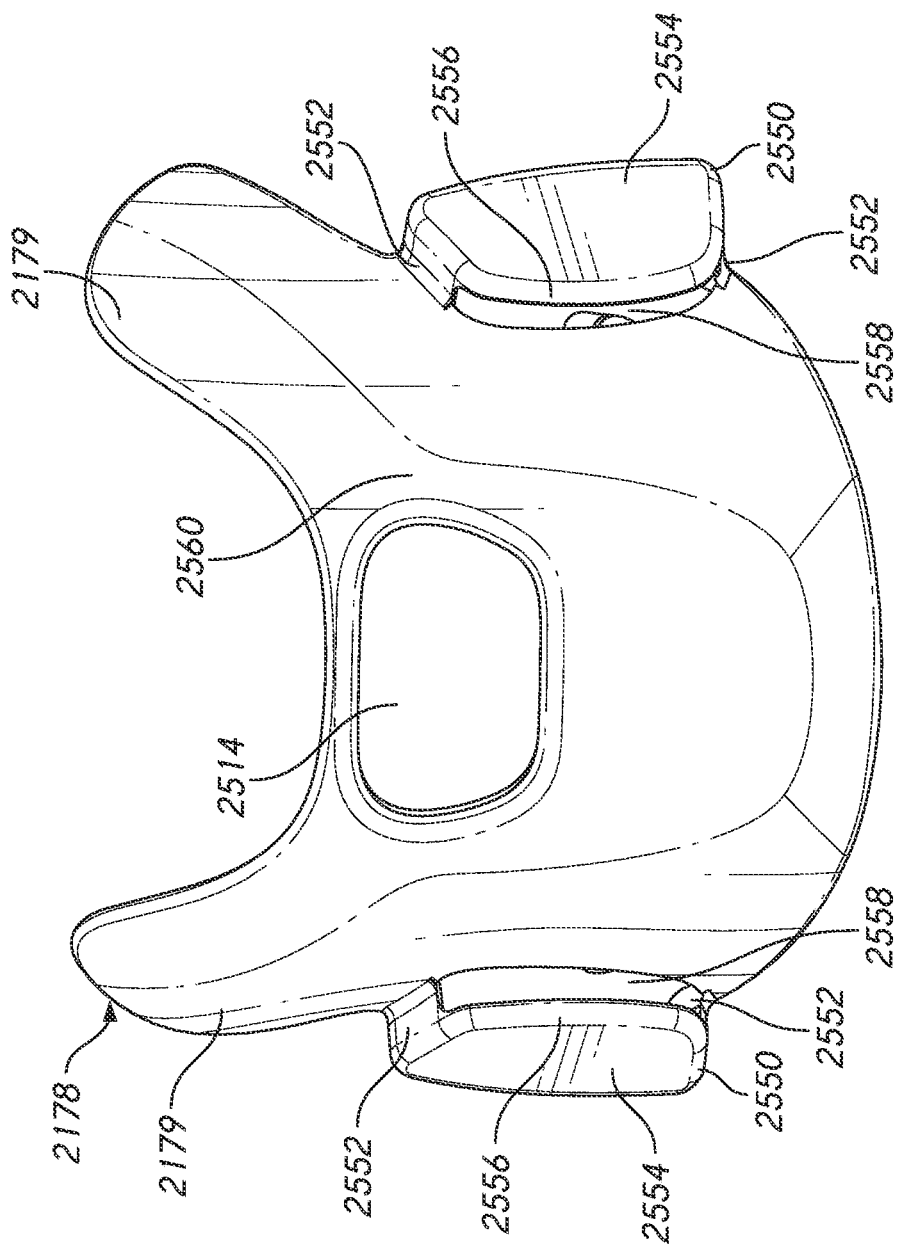
FIG. 32A is a front view of a frame of the mask assembly of FIG. 29.
Figure 32B:
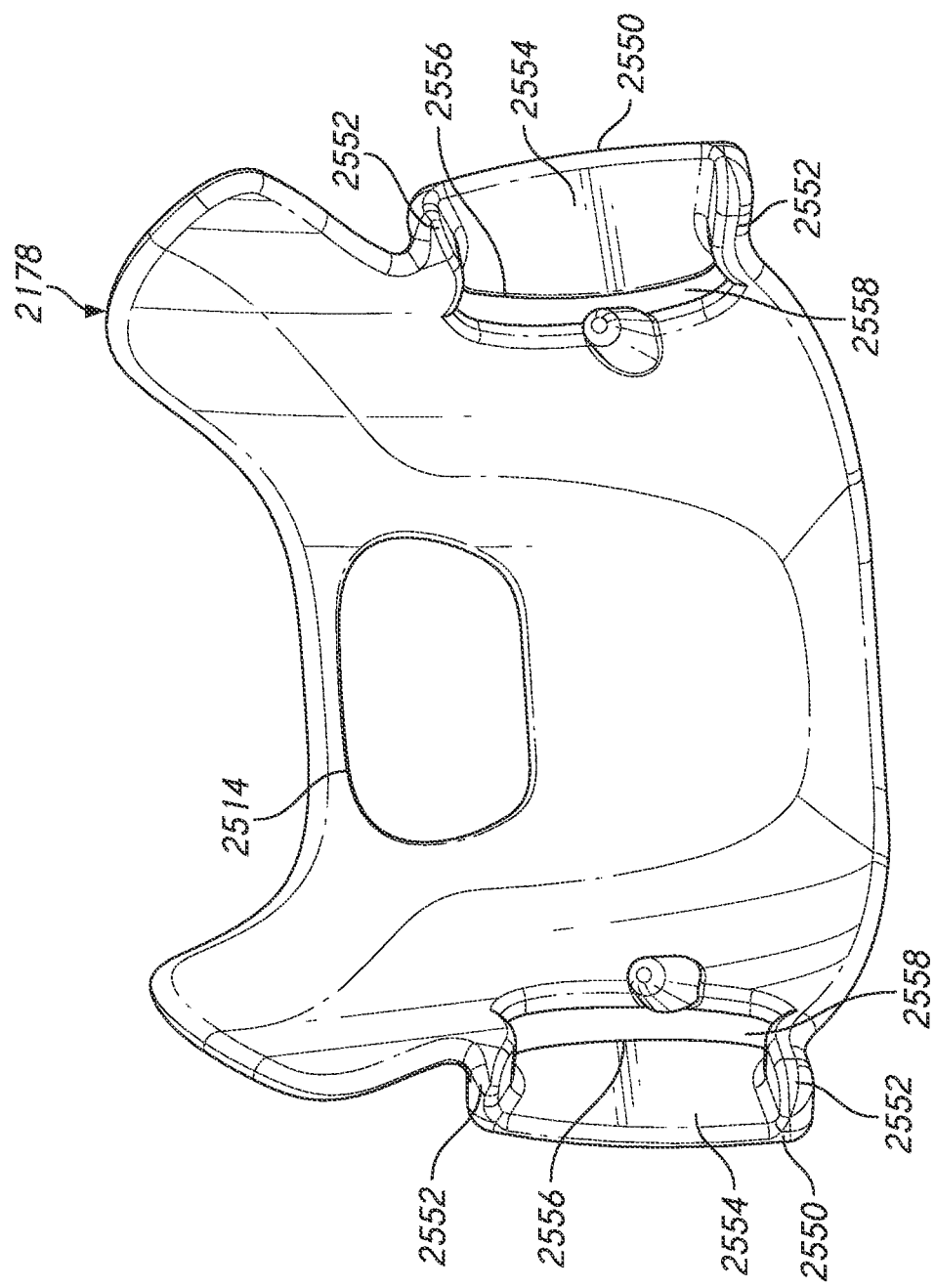
FIG. 32B is a rear view of a frame of the mask assembly of FIG. 29.

FIGS. 32A and 32B illustrate various configurations of the frame 2178 of the mask assembly 2100. As shown in FIGS. 32A and 32B, the frame 2178 can include a plurality of clip retention features 2550 and a vent aperture 2514. The clip retention features 2550 can be positioned along lateral sides of the frame 2178. For example, the clip retention features 2550 can be positioned laterally offset from a center portion of the frame 2178. In some configurations, the clip retention features 2550 are positioned along and/or extend from outermost lateral sides of the frame 2178. As shown in the illustrated configuration, the clip retention features 2550 can be positioned at least partially below the paddles 2179 of the frame 2178.

In some configurations, as shown FIGS. 32A and 32B, the clip retention features 2550 can include a raised wall 2554 and at least one support 2552. The raised wall 2554 can be offset forwardly or laterally from adjacent portions of the mask frame 2178. For example, the raised wall 2554 can provide a front face of the clip retention feature 2600 such that the raised wall 2554 is positioned forwardly from adjacent portions of a front surface 2560 of the frame 2178. In some configurations, the raised wall 2554 can follow a contour of the front surface 2560 of the frame 2178. For example, the raised wall 2554 can be substantially flat and/or curved to conform to the shape of the frame 2178. In such configurations, the raised wall 2554 can extend substantially parallel to the mask frame 2178 and can extend from a lateral side of the frame 2178 towards a center portion of the mask frame 2178. In some configurations, the raised wall 2554 extends from a bottom region of the paddles 2179 toward or to a lower region of the mask frame 2178. For example, in some configurations, the raised wall 2554 extends along an entire lateral side of the mask frame 2178 below the paddles 2179. If desired, the raised wall 2554 could extend along an entirety or a substantial entirety of the lateral side of the mask frame 2178.

In some configurations, the raised wall 2554 is connected to the frame 2178 by at least one support 2552. Preferably, each clip retention feature 2550 can include at least two supports 2552 spaced apart from one another on, for example, upper and lower edges of the raised wall 2554. The support 2552 can connect the raised wall 2554 to the frame 2178 along an upper side, a lower side, and/or a lateral side of the raised wall 2554. In some configurations, the support 2552 extends outwardly from the mask frame 2178 to connect to the raised wall 2554 in a direction substantially perpendicular to the front surface 2560 of the frame 2178. Thus, the support 2552 can support the raised wall 2554 at a position offset forward of the front surface 2560 of the frame 2178. Accordingly, a gap 2558 of the frame 2178 can be formed within the clip retention feature 2550 and the frame 2178. The gap 2558 of the frame 2178 can provide an aperture in the frame 2178 to receive at least a portion of the headgear 2180 and/or at least a portion of the headgear clips 2600. As shown in the illustrated configuration, the gap 2558 of the frame 2178 can be defined by a front edge 2556 of the raised wall 2554, the supports 2552, and the front surface 2560 of the frame 2178. In some configurations, the front edge 2556 of the raised wall 2554 extends forward of the supports 2552 to form a lip. The lip can desirably engage and/or retain the headgear clip 2600 in use.

FIGS. 33A-33E illustrate an example configuration of the headgear clip 2600. The headgear clip 2600 can include an upper strap slot 2602, a lower strap slot 2604, an aperture 2606, a step 2608, a pull tab 2630, and a front surface 2620. In some configurations, the headgear clip 2600 can form a substantially "D" shape. For example, the aperture 2606 can be centrally located within the headgear clip 2600. In some configurations, the aperture 2606 can be laterally positioned between the pull tab 2630 and the upper and lower strap slots 2602, 2604. In some configurations, the aperture 2606 can have a maximum height that is greater than a maximum width of the aperture 2606.

In such configurations, the clip retention feature 2550 can extend entirely through the aperture 2606 during assembly of the mask assembly 2100. For example, the aperture 2606 can be formed in at least a portion of the headgear clip 2600. In some configurations, the aperture 2606 is formed through an insert 2614 of the headgear clip 2600 (described in more detail below). In some configurations, the headgear clip 2600 can clip over, attach, and/or snap onto a corresponding clip retention feature 2550 of the frame 2178. For example, the aperture 2606 can receive at least a portion of the clip retention feature 2550. When assembled, the aperture 2606 can pass over the clip retention feature 2550 of the frame 2178 and can slide rearwardly into the gap 2558 of the frame 2178 formed at the front of the clip retention feature 2550. In such configurations, a forward portion of a perimeter formed by the aperture 2606 can sit between the raised wall 2554 of the clip retention feature 2550 and the front surface 2560 of the frame 2178. Thus, the forward portion of the perimeter of the aperture 2606 can be retained beneath the lip formed at the front edge 2556 of the clip retention feature 2550.

As shown in FIGS. 33C-33E, the headgear connector 2600 can include an over-mould arrangement. For example, the headgear connector 2600 can include an insert 2614. In some configurations, the insert 2614 can be formed by a plastic. For example, the plastic of the insert 2614 can be substantially rigid. The insert 2614 can be over-moulded with a relatively flexible and/or soft material, such as silicone or TPE. In some configurations, the over-mould can form the pull tab 2630.

In some configurations, the aperture 2606 and/or the upper and lower strap slots 2602, 2604 can be formed through and/or within the insert 2614. In some configurations, the insert 2614 can provide structure to the headgear clip 2600. For example, the insert 2614 can provide a substantially rigid connection between headgear straps of the headgear 2180 and the frame 2178. As shown in the illustrated examples, the upper and lower strap slots 2602, 2604 can be spaced apart to allow upper and lower headgear straps to be connected to the frame 2178. For example, the upper strap slot 2602 can be positioned offset above the lower strap slot 2604. When worn, this arrangement can allow the upper strap of the headgear 2180 to pass above the user's ear and the lower strap of the headgear 2180 to pass below the user's ear. Such configurations can desirably improve the mask's stability when the interface assembly is worn on the user's face.

As shown in the illustrated arrangements, the over-mould can surround at least a portion of the insert 2614. In some configurations, the over-mould forms a perimeter around substantially the entire insert 2614 or the entire insert 2614. The over-moulded arrangement can desirably provide a surface that can be soft to touch and/or easily gripped by a user. For example, the over-moulded arrangement can provide flexibility to at least a portion of the headgear clip 2600 (e.g., the pull tab 2030). The over-moulded arrangement can provide at least some rigidity to support the connection between the frame 2178 and the headgear 2180.

In some configurations, the over-mould can form the pull tab 2630 and a rotation lock 2616. In some configurations, the rotation lock 2616 can include a protrusion that extends rearwardly from a rear surface 2624 of the headgear clip 2600. In some configurations, protrusion can be substantially L-shaped. However, in some configurations, the protrusion can form various shapes. The protrusion can extend along at least a portion of a rear and/or lower edge of the headgear clip 2600. For example, the protrusion can extend along at least a portion of a lower portion of the insert 2614. The protrusion may extend laterally beyond a lateral edge of the lower portion of the insert 2614. In some configurations, the protrusion extends vertically along the rear surface of the headgear clip 2600. In some configurations, a rear surface of the protrusion extends approximately parallel to the rear surface 2624 of the headgear clip 2600.

The rotation lock 2616 can abut and/or be positioned adjacent a lower edge of the frame 2178. In some configurations, the rotation lock 2616 can abut and/or be positioned adjacent the support 2552 of the clip retention feature 2550. In configurations described herein, the rotation lock 2616 can desirably prevent rotation of the headgear clip 2600 about an axis that extends approximately perpendicular to the raised wall 2554 of the clip retention feature 2550.

In some configurations, the vertical portion of the rotation lock 2616 of the headgear clip 2600 can include the upper and lower strap slots 2602, 2604 that form apertures that pass through the protrusion. As shown in FIG. 33B, the upper and lower strap slots 2602, 2604 can include a strap guide 2612. The strap guide 2612 can form a cut out in a rear edge 2622 of the rotation lock 2616. In some configurations, the strap guide 2612 can provide a smooth surface. For example, the strap guide 2612 can desirably align and/or direct headgear straps into a proper arrangement within the upper and lower strap slots 2602, 2604 of the headgear connector 2600. Such configurations may advantageously help to reduce the bulkiness caused by the headgear straps connecting to the headgear connector 2600 and/or the depth of the headgear straps when assembled. For example, the strap guide 2612 can allow the headgear straps to lay substantially flat against the headgear clip 2600.

In some configurations, the rotation lock 2616 includes a keyed portion to indicate a proper position to connect to the mask frame 2178. For example, the rotation lock 2616 can prevent a left headgear connector 2600 from being connected to a right clip retention feature 2550 and/or a right headgear connector 2600 from being connected to a left clip retention feature 2550. Similarly, the rotation lock 2616 can prevent the headgear connectors 2600 from being positioned in the incorrect vertical arrangement.

In some configurations, the pull tab 2630 includes a front surface that can have portions extending above and/or below the aperture 2606 formed in the headgear clip 2600. The front surface of the pull tab 2630 can be raised and/or extend outwardly relative to a front surface of at least a portion of the headgear clip 2600. For example, the front surface of the pull tab 2630 can be raised and/or extend outwardly relative to a front surface of a portion of the headgear clip 2600 that surrounds the aperture 2606 and/or is adjacent to the aperture 2606.

Figure 33A:
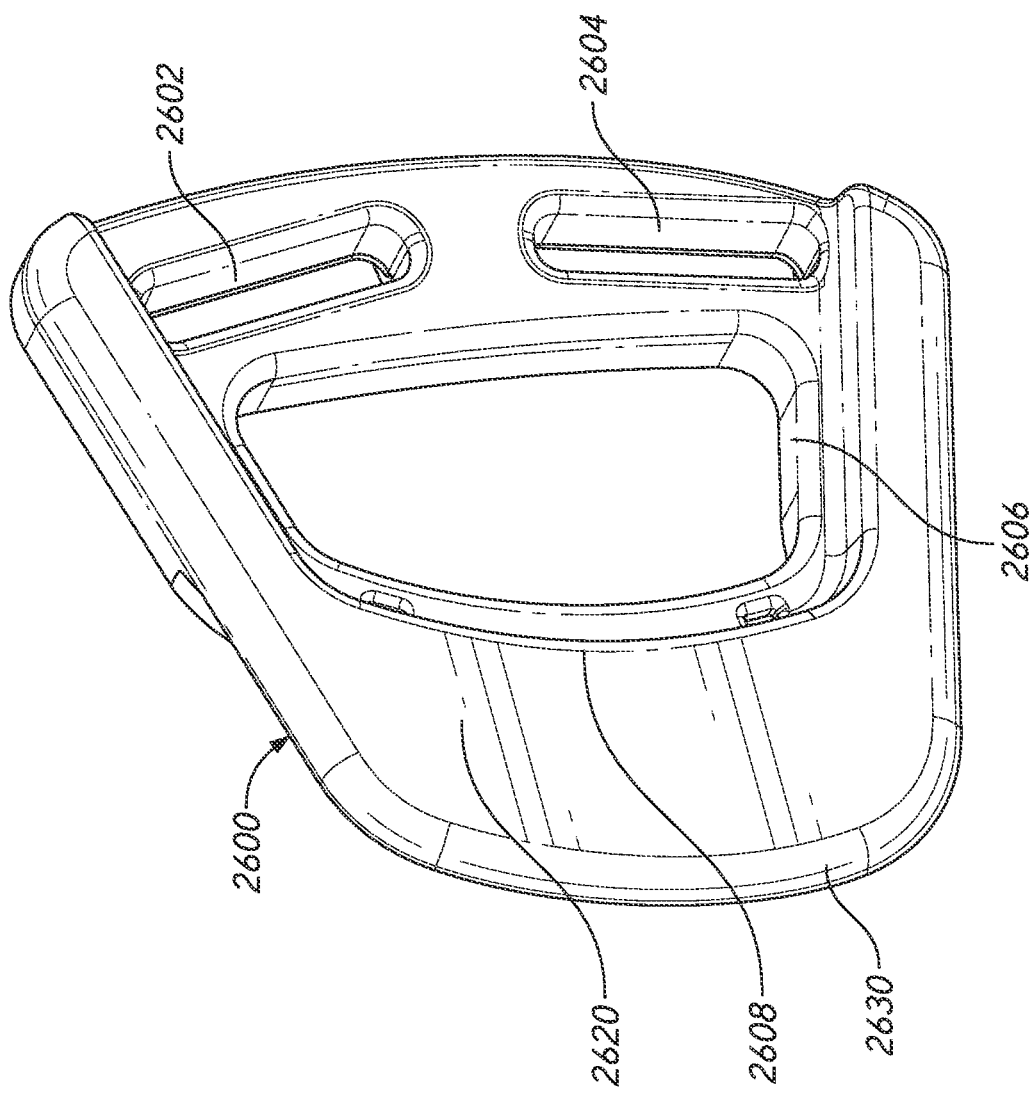
FIG. 33A is a front view of a headgear clip of the mask assembly of FIG. 29.

As shown in FIG. 33A, for example, the raised front surface 2620 of the pull tab 2630 can form a step 2608. The step 2608 can form the front surface and can form at least a portion of the perimeter surrounding the aperture 2606. The step 2608 can desirably prevent the headgear clip 2600 from being incorrectly attached and/or aligned with the frame 2178 during assembly of the mask assembly 2100. For example, the step 2608 can prevent the headgear clip 2600 from attaching to the frame 2178 in an incorrect back-to-front orientation, by providing a surface that is offset from the aperture 2606. That is, the step 2608 can prevent the clip 2600 from engaging the clip retention feature 2550 when the front side (visible in FIG. 33A) is positioned inwardly against or adjacent to the frame 2178 instead of the correct outwardly-facing orientation. Such configurations can prevent the aperture 2606 from sliding under and/or receiving the corresponding clip retention feature 2550 of the frame 2178.

In some configurations, the pull tab 2630 can be somewhat elastic and/or flexible. For example, the pull tab 2630 can be formed of a substantially flexible material that allows the pull tab 2630 to stretch and/or flex when a force is applied to the pull tab 2630. For example, the pull tab 2630 may stretch when pulled to disconnect the headgear clip 2600 from the corresponding clip retention feature 2550. Such an arrangement may encourage a peeling-type action to disconnect the headgear clip 2600 from the clip retention feature 2550. Such arrangements may ensure that the user properly disconnects the clip 2600 from the clip retention feature 2550. For example, such arrangements may ensure that the user does not inadvertently remove and/or disconnect the clip 2600 from the clip retention feature 2550 and/or may minimize the risk that the user does so. In some configurations, the pull tab 2630 can provide a sufficient tensile force to allow only a portion of the headgear clip 2600 to flex laterally.

As shown in FIGS. 33C-33E, for example, the over-mould may not form the upper and lower strap slots 2602, 2604. For example, the upper and lower strap slots 2602, 2604 can be formed by a material having a greater thickness and/or rigidity than the surrounding surfaces, which can be the insert 2614 in some configurations. Such arrangements can provide a low-friction surface finish that allows headgear straps to pass through the upper and lower strap slots 2602, 2604 to be easily adjusted and/or slide within the upper and lower strap slots 2602, 2604.

FIGS. 34A-35B illustrate configurations of the mask assembly 2100. The mask assembly 2100 can include the frame 2178 and first and second headgear clips 2600A, 2600B. The first and second headgear clips 2600A, 2600B can be defined as right and left headgear clips 2600A, 2600B from the perspective of the wearer of the mask assembly 2100. FIGS. 34A and 34B illustrate example configurations of the first and second headgear clips 2600A, 2600B connected to the frame 2178.

Figure 35A:
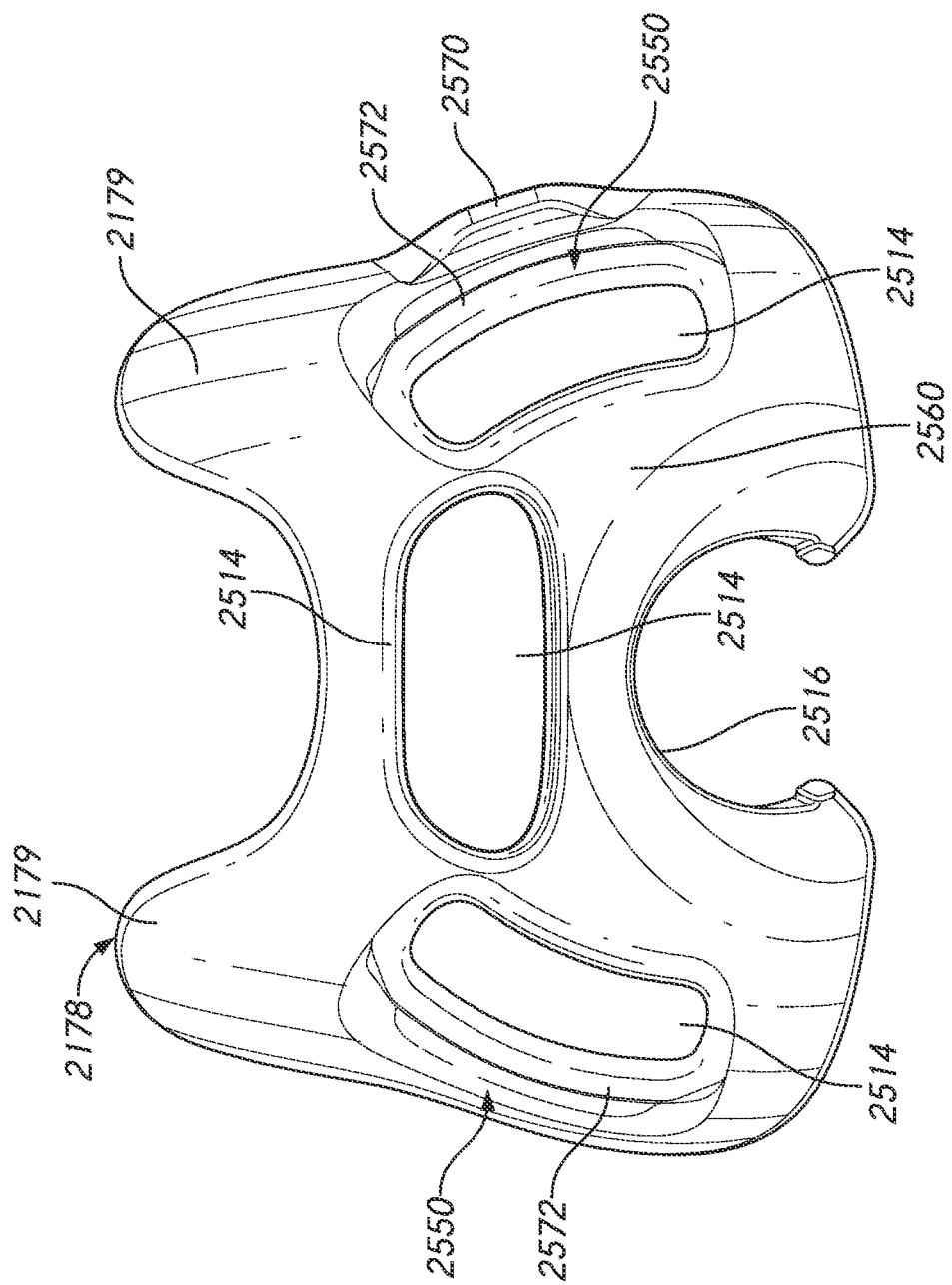
FIG. 35A is a front view of a frame of the mask assembly of FIG. 34A.
Figure 35B:
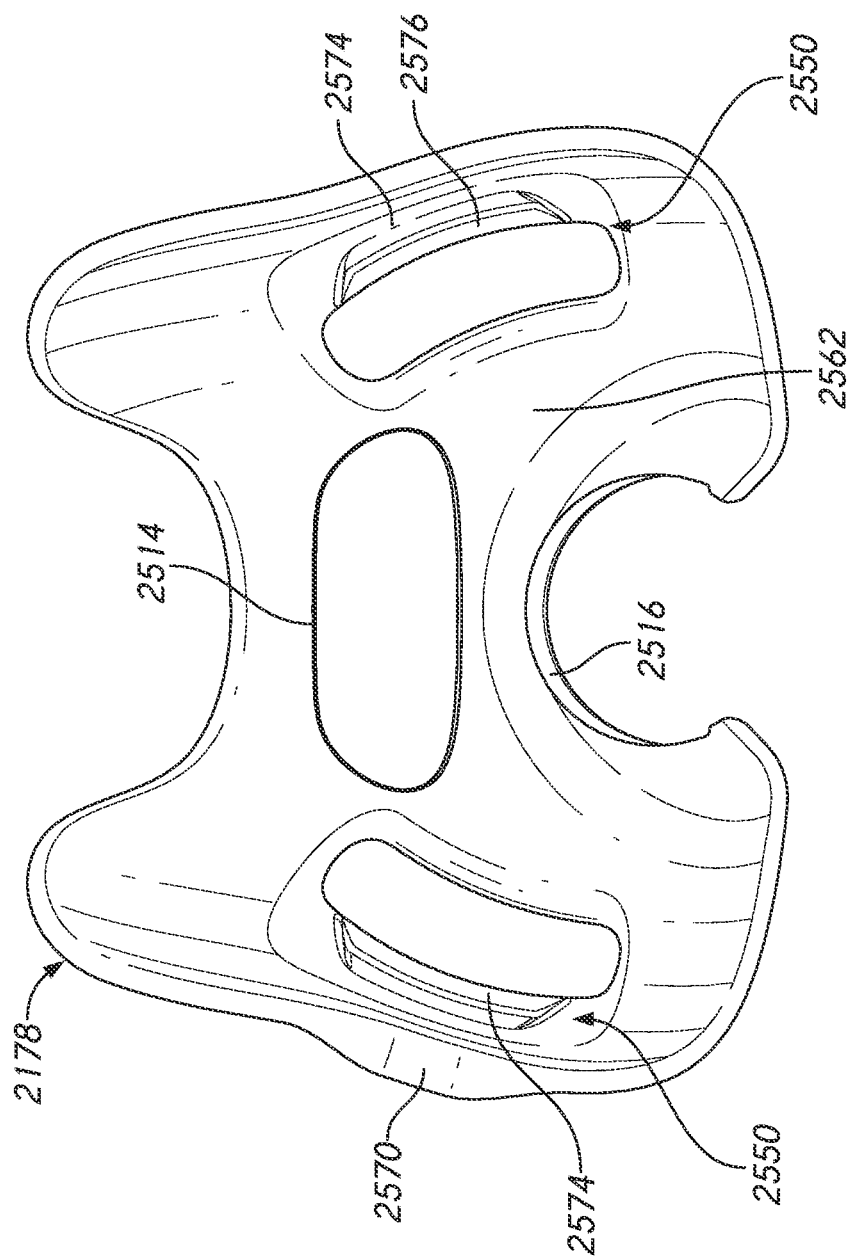
FIG. 35B is a rear view of a frame of the mask assembly of FIG. 34A.

As shown in FIGS. 35A and 35B, the frame 2178 can include at least one clip retention feature 2550 and at least one vent aperture 2514. For example, the frame 2178 can include at least two vent apertures. In some configurations, the frame 2178 can include at least three openings. The clip retention feature 2550 can at least partially form a vent aperture 2514 that extends through the frame 2178. The vent aperture 2514 can provide an opening in the frame 2178 to receive at least a portion of a headgear clip 2600. The vent aperture 2514 can be substantially rectangular, circular, and/or oval-shaped. For example, the vent aperture 2514 can include a top side, a bottom side, and at least one lateral side. As shown in FIGS. 35A and 35B, the top side and the bottom side of the vent aperture 2514 can be curved. In some configurations, the top side and the bottom side of the vent aperture 2514 can be concave and can face a center portion of the frame 2178. For example, the concave top side and bottom side of the vent aperture 2514 can generally face towards an apex of the elbow connector 2516.

In some embodiments, the connection feature 2550 can include a raised edge 2572. The raised edge 2572 can be formed by a lateral-most side of the aperture of the connection feature 2550 that is positioned close to an outermost lateral side of the frame 2178. For example, the raised edge 2572 can extend outwardly from the contoured front surface 2560 of the frame 2178. The raised edge 2572 can include an increased thickness relative to portions of the frame 2178 that surround the raised edge 2572.

In some configurations, the raised edge 2572 extends along the length of the lateral edge of the vent aperture 2514, forming a connection point for the headgear clip 2600. For example, the raised edge 2572 can form a post 2576 to connect to a hook 2654 of the headgear clip 2600 (see, e.g., FIG. 40). Such arrangements may provide clearance for the hook 2654 of the headgear clip 2600 to pass through the aperture. Such configurations can allow the headgear clip 2600 to be easily aligned with and/or connected to the frame 2178.

For example, the raised edge 2572 can form an alignment feature 2574 that properly aligns the headgear clip 2600 with the frame 2178 (see, for example, FIG. 35B). Accordingly, the raised edge 2572 can form a stepped region and/or a recess on a rear surface of the frame 2178. In some configurations, the alignment feature 2574 can receive at least part of the hook 2654 of the headgear clip 2600. In some configurations, the alignment feature 2574 can have a varied wall thickness. For example, the wall thickness may be greater at the raised edge 2572, such as at the post 2576 compared to the surrounding surfaces, including the surfaces adjacent the post 2576 and the surrounding lateral surfaces of the rear surface of the frame 2178. In such configurations, the alignment feature 2574 can abut with the hook 2654 of the headgear clip 2600 to desirably minimize and/or prevent rotation about an axis that is substantially perpendicular to the front surface 2560 of the frame 2178 proximal to the clip retention features 2550. Such arrangements may prevent the clip from dislodging from the clip retention features 2550 as a result of the headgear being pulled up, down, and/or away from the mask assembly 2100. The alignment feature 2574 can desirably provide an anti-sliding or anti-slip surface.

Thus, the alignment feature 2574 can prevent the headgear clip 2600 from sliding along the post 2576 of the clip retention feature 2550. Such arrangements can provide a more secure connection between the headgear 2180 and the mask assembly 2100. Similarly, such arrangements can provide greater stability to the connection between the headgear 2180 and the mask assembly 2100.

As shown in FIGS. 34A-35B, the frame 2178 can include a keying bump 2570. In some configurations, the keying bump 2570 can be formed in the frame 2178 adjacent only one of the clip retention features 2550. In some configurations, the keying bump 2570 can be formed in the frame 2178 positioned adjacent a plurality of clip retention features 2550. For example, the keying bump 2570 can allow the headgear clips 2600 to be keyed to the frame 2178 to permit assembly in only a proper orientation. In some configurations, the keying bump 2570 can extend outwardly from the front surface 2560 of a left lateral side of the frame 2178. The keying bump 2570 can preferably be positioned laterally offset from the left clip retention feature 2550 towards an outermost lateral edge of the frame 2178. The keying bump 2570 can align with a corresponding keying notch 2650 on the second and/or left headgear clip 2600B, for example. In some configurations, the keying bump 2570 can desirably prevent the incorrect headgear clip 2600 (in this example, the right headgear clip 2600A) from connecting to the left side of the frame 2178. In some configurations, the keying bump 2570 desirably prevents the headgear 2180 from being attached to the frame 2178 in the incorrect horizontal alignment, vertical alignment, and/or front-back orientation. Thus, the keying bump 2570 can enhance the usability of the mask assembly 2100 and/or allow the mask assembly 2100 to be easily assembled and/or disassembled.

FIGS. 36A-43 illustrate configurations of the first and second headgear clips 2600A, 2600B and/or the first and second headgear clips 2600A, 2600B connected to the frame 2178. The first and second headgear clips 2600A, 2600B are similar or identical to other examples of the headgear clips 2600 discussed above in many respects. As shown in the illustrated configurations, the first and second headgear clips 2600A, 2600B include an aperture that can clip over and/or receive at least a portion of corresponding clip retention feature 2550 (e.g., the post 2576) of the frame 2178. In some configurations, the first and second headgear clips 2600A, 2600B are formed of a substantially rigid material, such as nylon, polycarbonate, and/or polypropylene, among other materials. Thus, the first and second headgear clips 2600A, 2600B can desirably provide support to the headgear 2180 and/or maintain the connection between the headgear 2180 and the frame 2178.

The first and second headgear clips 2600A, 2600B can include an aperture 2606, a thumb grip 2640, a finger grip 2642, an upper strap slot 2602, a lower strap slot 2604, an over-moulded grip 2644, a hook 2654, and a keying notch 2650. For example, the first and second headgear clips 2600A, 2600B can form a substantially arcuate loop that surrounds aperture 2606. Accordingly, the aperture 2606 can be centrally positioned within the first and second headgear clips 2600A, 2600B. In some configurations, the aperture 2606 can receive at least a portion of the clip retention features 2550 (e.g., a raised lip 2652) of the frame 2178. For example, when the first and second headgear clips 2600A, 2600B are connected to the frame 2178 via the clip retention features 2550, the first and second headgear clips 2600A, 2600B can sit substantially flush with the front surface 2560 of the frame 2178.

In some configurations, the first and second headgear clips 2600A, 2600B can include the thumb grip 2640. The thumb grip 2640 can be defined by a raised tab positioned along an outer lateral edge of the first and second headgear clips 2600A, 2600B relative to a central plane extending vertically between the first and second headgear clips 2600A, 2600B. Such configurations can desirably provide a grip for a user's thumb. For example, the user can rest their thumb against the thumb grip 2640. In some configurations, the thumb grip 2640 can have a greater thickness than the surrounding portions of the thumb grip 2640. Such configurations can desirably provide an increased contact area for the user's thumb to grip, thereby allowing the user to easily connect and/or disconnect the first and second headgear clips 2600A, 2600B from the corresponding clip retention features 2550.

Figure 36B:
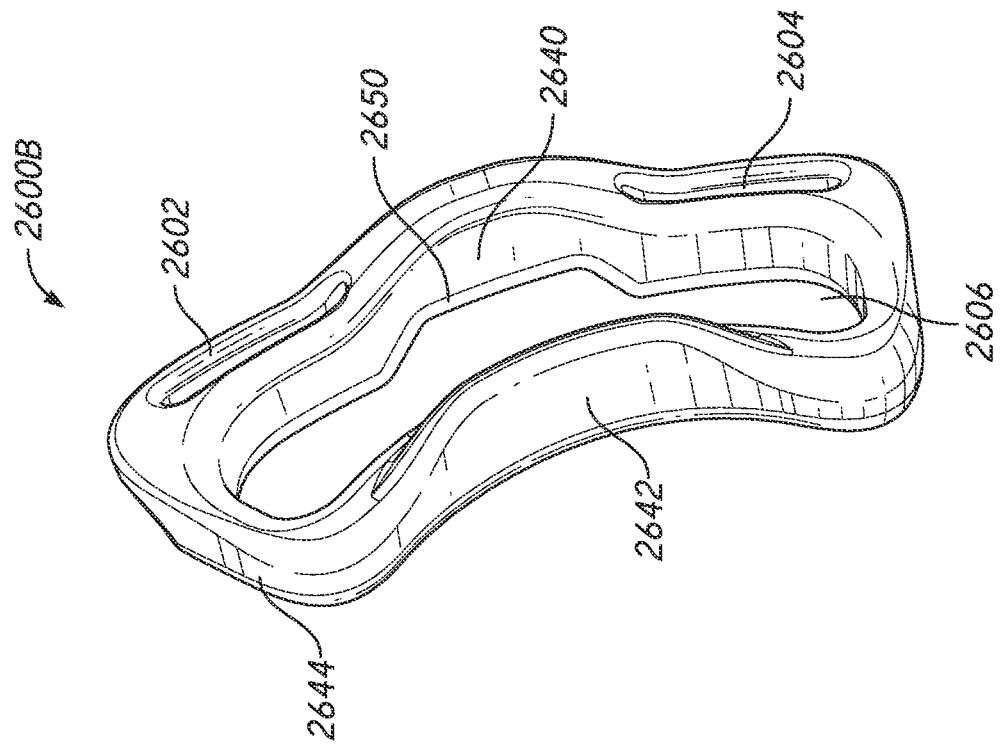
FIG. 36B is a front view of a second headgear clip of the mask assembly of FIG. 34A.
Figure 36A:
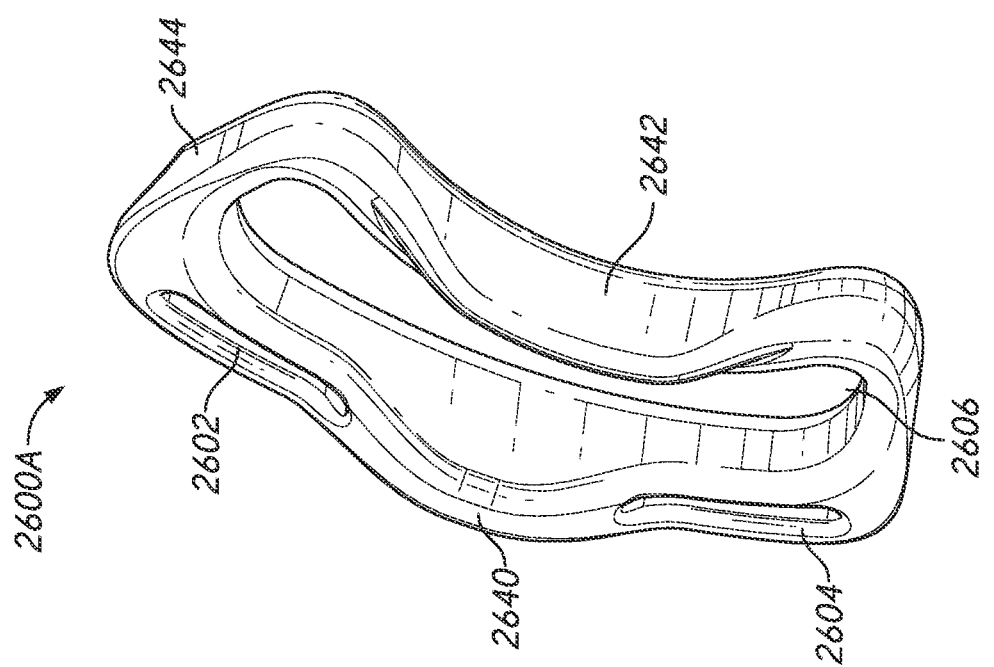
FIG. 36A is a front view of a first headgear clip of the mask assembly of FIG. 34A.

As shown in at least FIGS. 36A and 36B, the first and second headgear clips 2600A, 2600B forms a concave surface along at least a portion of the first and second headgear clips 2600A, 2600B (e.g., along a portion of an outer lateral edge of the first and second headgear clips 2600A, 2600B). For example, the thumb grip can be centrally positioned along an outer lateral edge of the first and second headgear clips 2600A, 2600B. The concave surface of the thumb grip 2640 can provide a comfortable gripping surface for the user. In some configurations, the concave surface can provide a visual indicator that can indicate to the user that the surface of the thumb grip 2640 should be gripped by the user.

In some configurations, the first and second headgear clips 2600A, 2600B includes a finger grip 2642. The finger grip 2642 can be defined by a raised tab positioned along an inner lateral edge of the first and second headgear clips 2600A, 2600B. Such configurations can desirably provide a grip for one or more of a user's fingers. For example, the user can rest their finger against the finger grip 2642. In some configurations, the finger grip 2642 can have a greater thickness than the surrounding portions of the finger grip 2642. Such configurations can desirably provide an increased contact area for the user's finger to grip, thereby allowing the user to easily connect and/or disconnect the first and second headgear clips 2600A, 2600B from the corresponding clip retention features 2550.

As shown in at least FIGS. 36A and 36B, the finger grip 2642 of the first and second headgear clips 2600A, 2600B forms a concave surface along at least a portion of the first and second headgear clips 2600A, 2600B (e.g., along a portion of an inner lateral edge of the first and second headgear clips 2600A, 2600B). For example, the finger grip 2642 can be centrally positioned along an inner lateral edge of the first and second headgear clips 2600A, 2600B. The concave surface of the finger grip 2642 can provide a comfortable gripping surface for the user. In some configurations, the concave surface can provide a visual indicator that can indicate to the user that the surface of the finger grip 2642 should be gripped by the user.

In some configurations, the finger grip 2642 can be positioned along a lateral edge of the first and second headgear clips 2600A, 2600B opposite the thumb grip 2640. For example, the finger grip 2642 and the thumb grip 2640 can be positioned on opposite sides of the aperture 2606. Such configurations can encourage the user to grip the first and second headgear clips 2600A, 2600B with their fingers towards a front edge of the clip. Such configurations can improve the user's control over the angle of the first and second headgear clips 2600A, 2600B during assembly and/or disassembly, thereby allowing the first and second headgear clips 2600A, 2600B to be easily connected to the clip retention features 2550. For example, the first and second headgear clips 2600A, 2600B can more easily align with the clip retention features 2550. In some configurations, the positioning and/or the shape of the finger grip 2642 relative to the thumb grip 2640 can encourage the user to grip a first outer side and a second outer side of the first and second headgear clips 2600A, 2600B.

In some configurations, the first and second headgear clips 2600A, 2600B can include upper and lower strap slots 2602, 2604. The upper and lower strap slots 2602, 2604 can be similar or identical to other examples of the upper and lower strap slots 2602, 2604 discussed above in many respects. Thus, the upper and lower strap slots 2602, 2604 can receive corresponding upper and lower headgear straps of the headgear 2180.

In some configurations, the over-moulded grip 2644 of the first and second headgear clips 2600A, 2600B can extend around at least a portion of the first and second headgear clips 2600A, 2600B. For example, the over-moulded grip 2644 can extend around the perimeter of the first and second headgear clips 2600A, 2600B. As shown in FIGS. 36A and 36B, the over-moulded grip 2644 can form at least a portion of the concave surfaces of the thumb grip 2640 and/or the finger grip 2642. In some configurations, the over-moulded grip 2644 can form the concave surfaces of the thumb grip 2640 and/or the finger grip 2642.

In some configurations, the over-moulded grip 2644 can include various materials, such as an elastomeric material. For example, the over-moulded grip 2644 can include silicone and/or TPE, among other materials. The over-moulded grip 2644 can provide a soft touch finish, providing a more comfortable grip on the first and second headgear clips 2600A, 2600B. In some configurations, the over-moulded grip 2644 can provide a grip to the user. In such configurations, the over-moulded grip 2644 can have a coefficient of friction greater than the surrounding portions of the first and second headgear clips 2600A, 2600B.

Figure 37B:
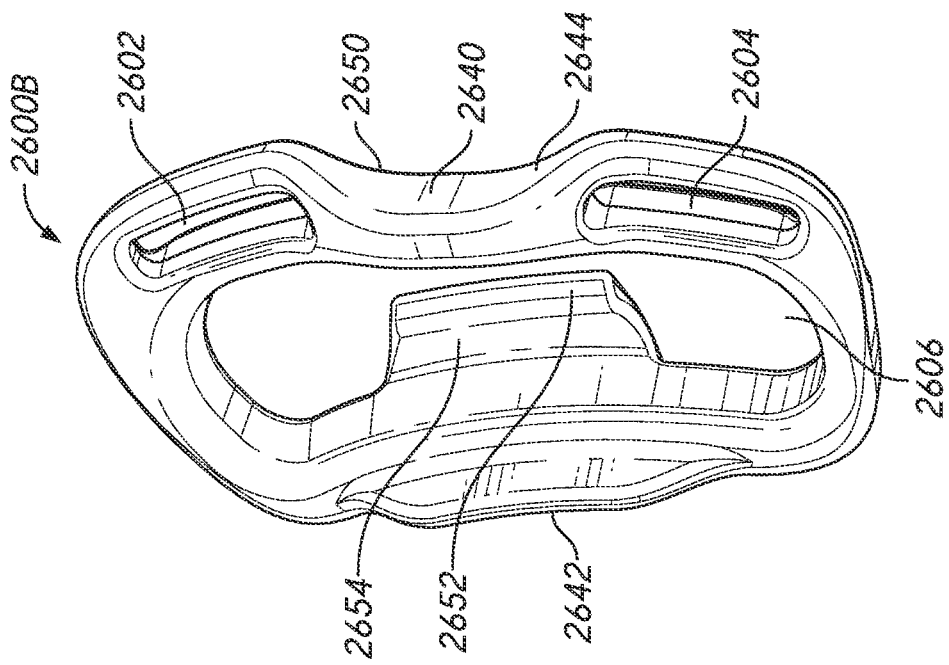
FIG. 37B is a side view of a second headgear clip of the mask assembly of FIG. 34A.
Figure 37A:
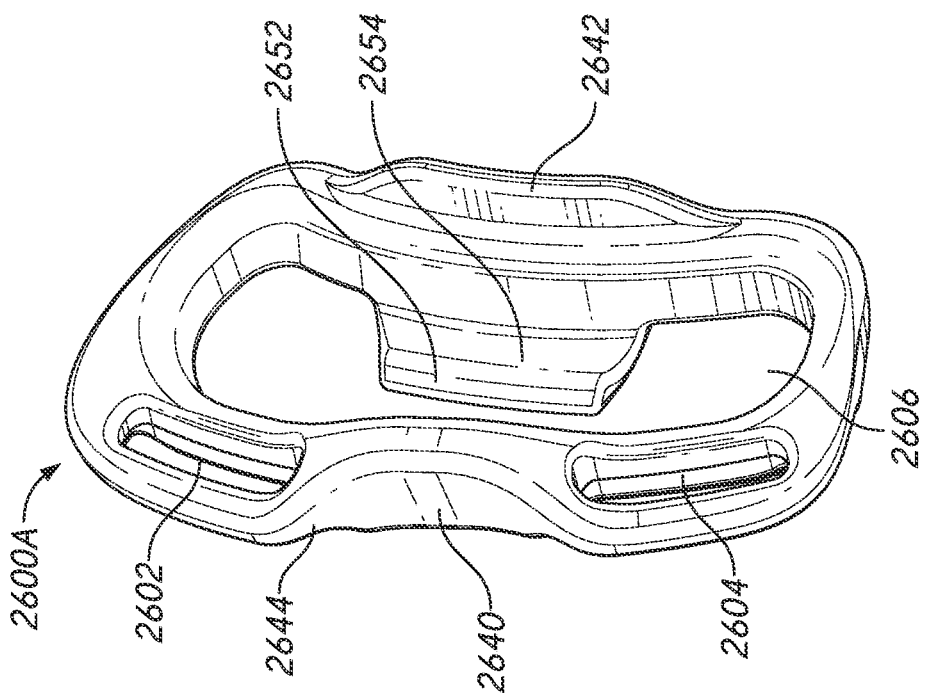
FIG. 37A is a side view of a first headgear clip of the mask assembly of FIG. 34A.
Figure 37D:
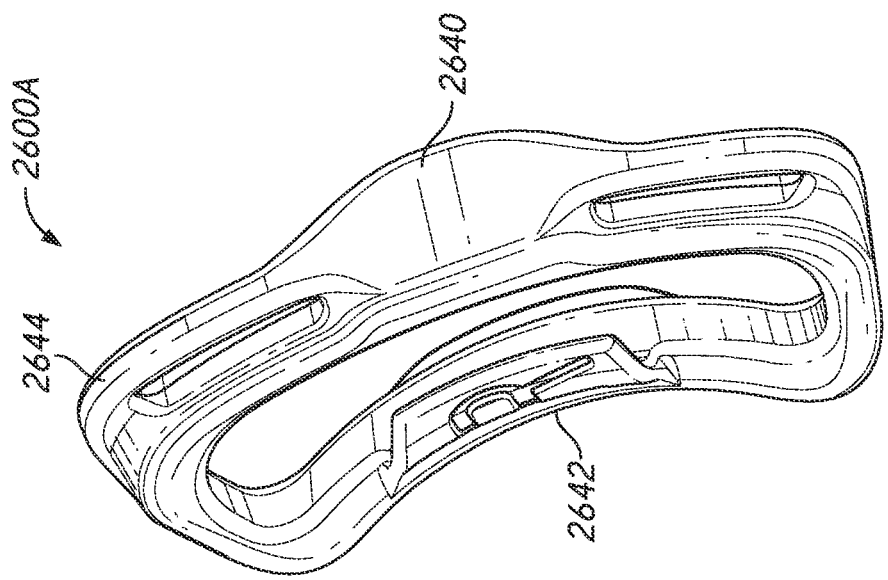
FIG. 37D is a rear view of a first headgear clip of the mask assembly of FIG. 34A.
Figure 37C:
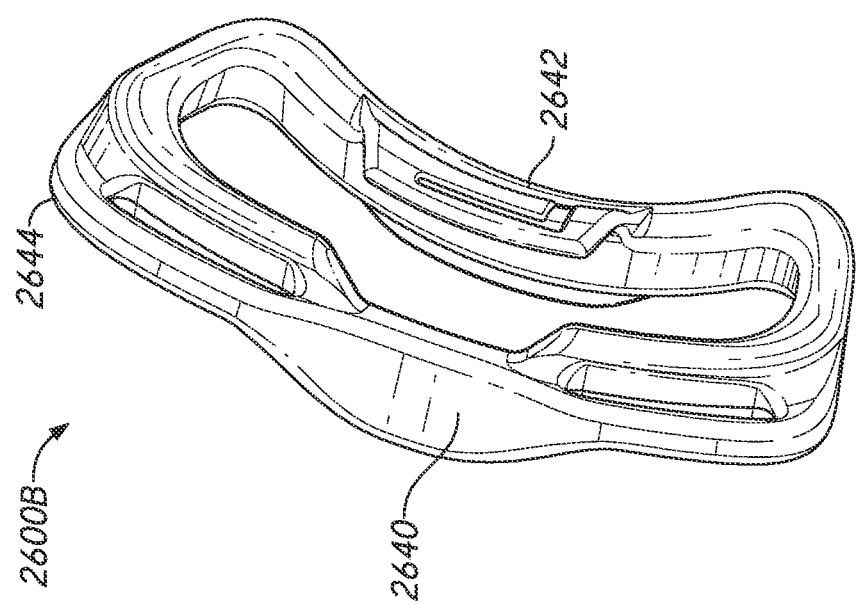
FIG. 37C is a rear view of a second headgear clip of the mask assembly of FIG. 34A.
Figure 38B:
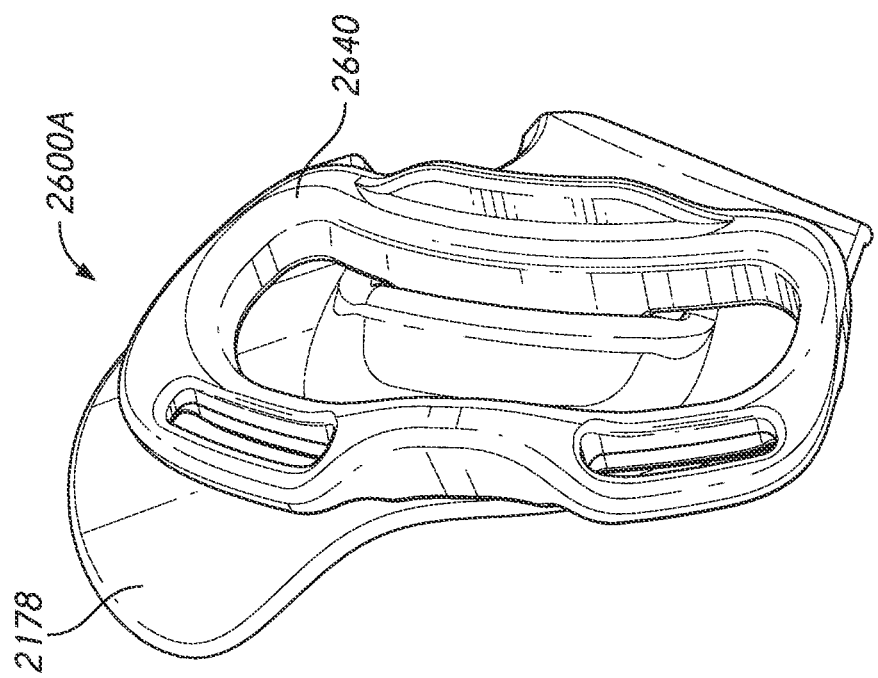
FIG. 38B is a side view of a first headgear clip assembly of the mask assembly of FIG. 34A.
Figure 38A:
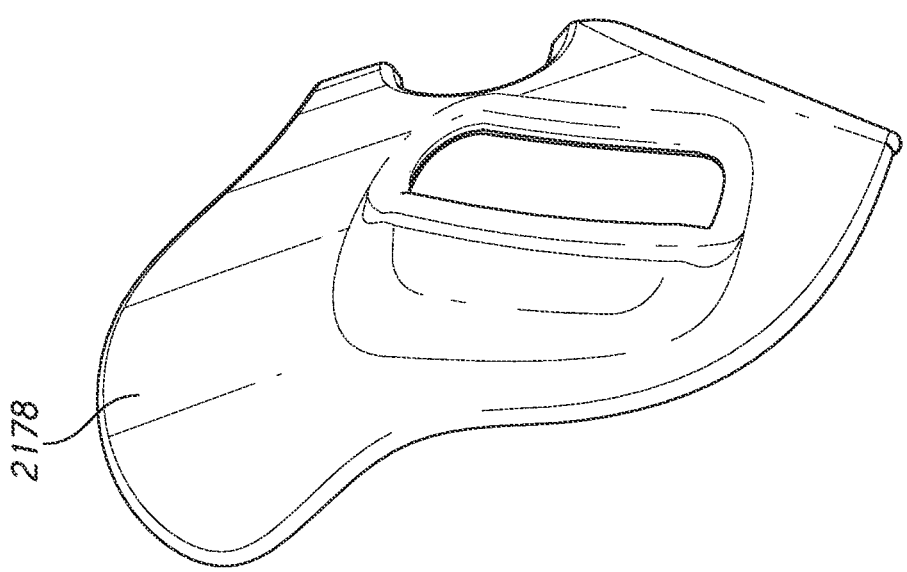
FIG. 38A is a side view of a first clip retention feature of the mask assembly of FIG. 34A.
Figure 39C:
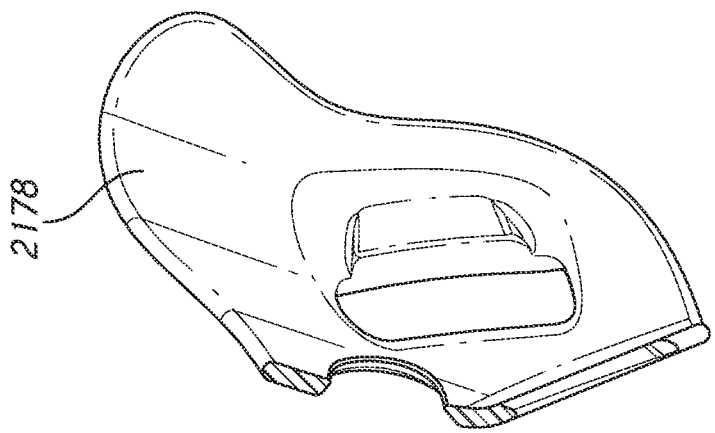
FIG. 39C is an interior side view of a second clip retention feature of the mask assembly of FIG. 34A.
Figure 39B:
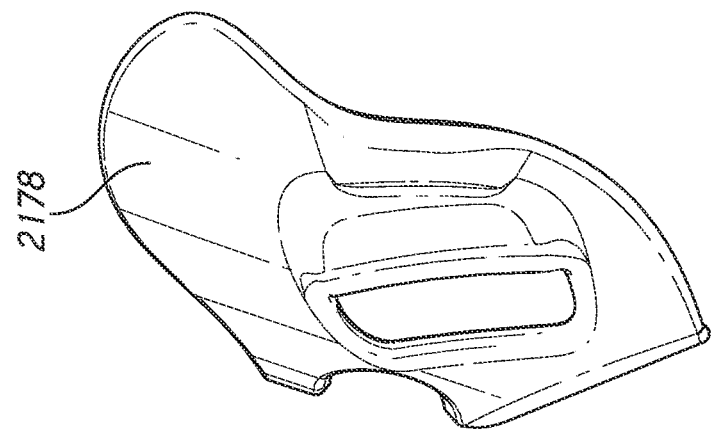
FIG. 39B is an exterior side view of a second clip retention feature of the mask assembly of FIG. 34A.
Figure 39A:
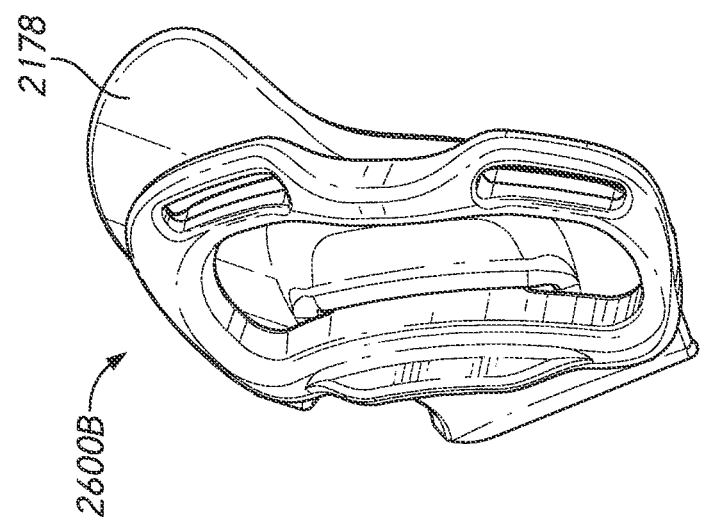
FIG. 39A is a side view of a second headgear clip assembly of the mask assembly of FIG. 34A.
Figure 41:
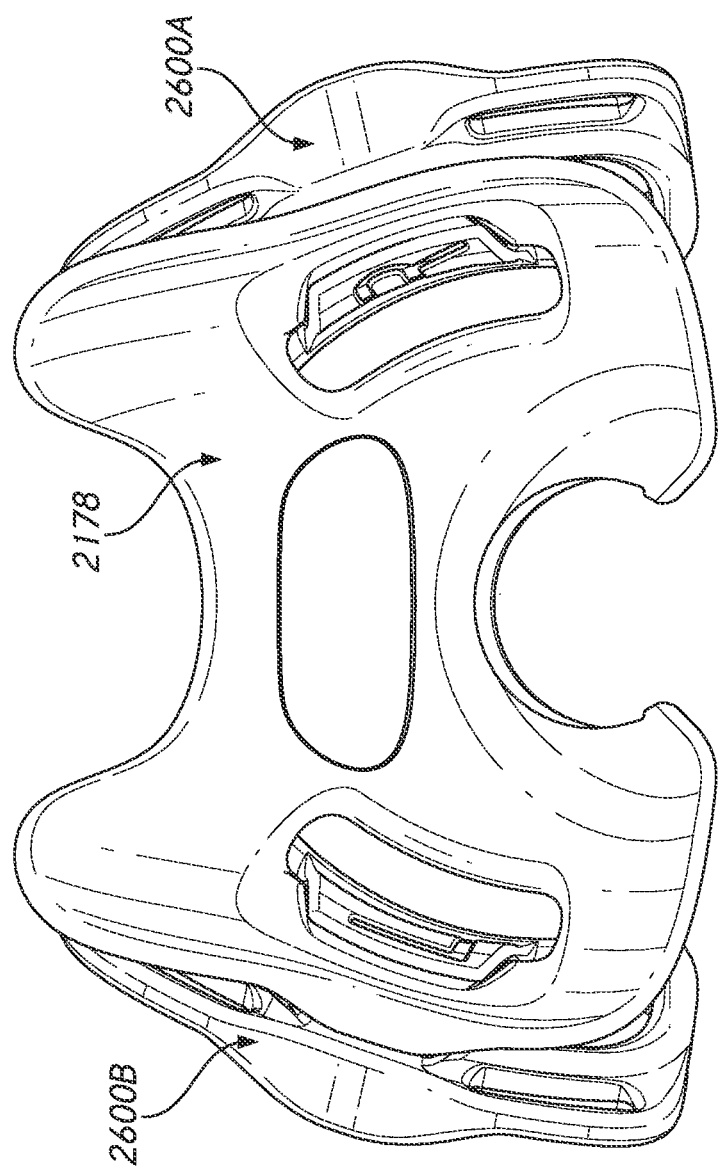
FIG. 41 is a rear view of a frame assembly of the mask assembly of FIG. 34A.
Figure 42:
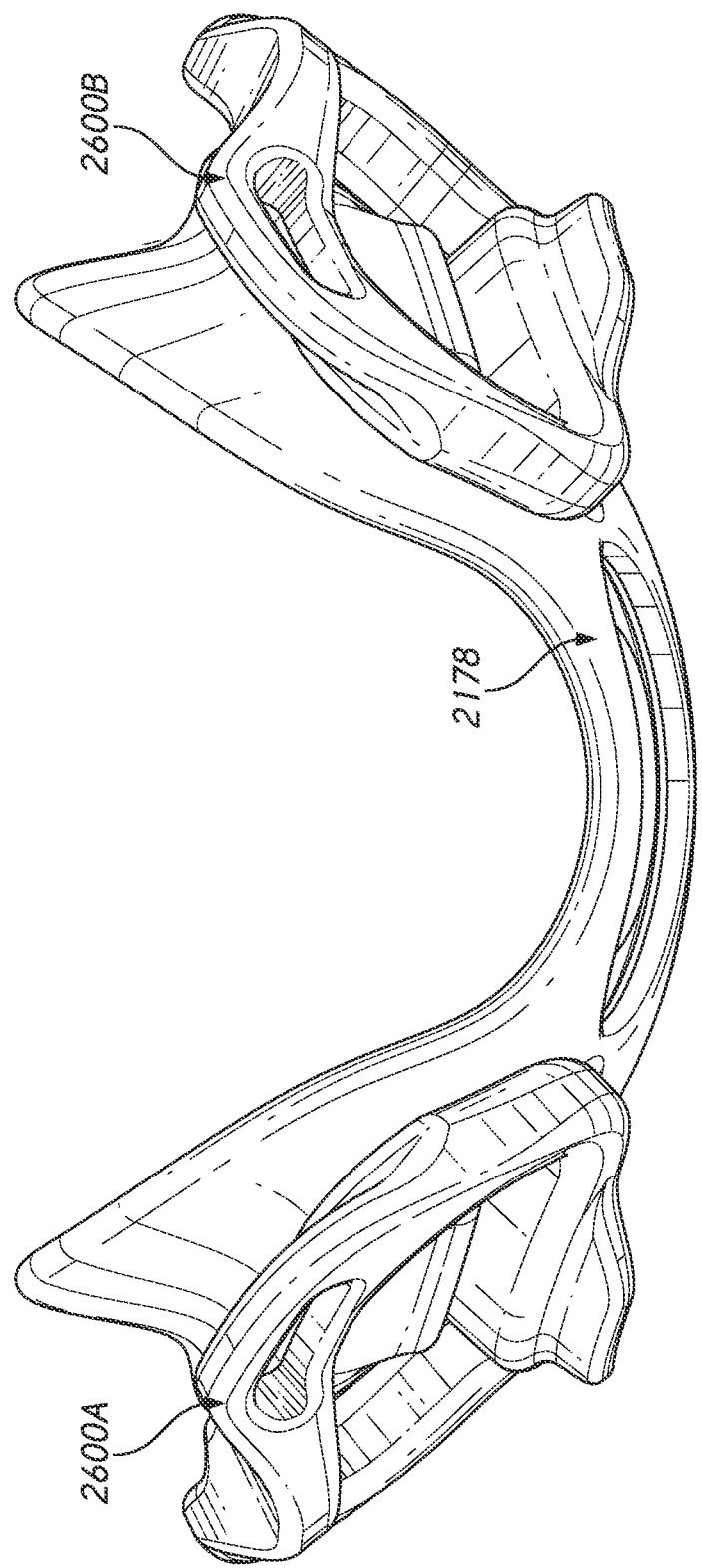
FIG. 42 is a top and front perspective view of a frame assembly of the mask assembly of FIG. 34A.
Figure 43:
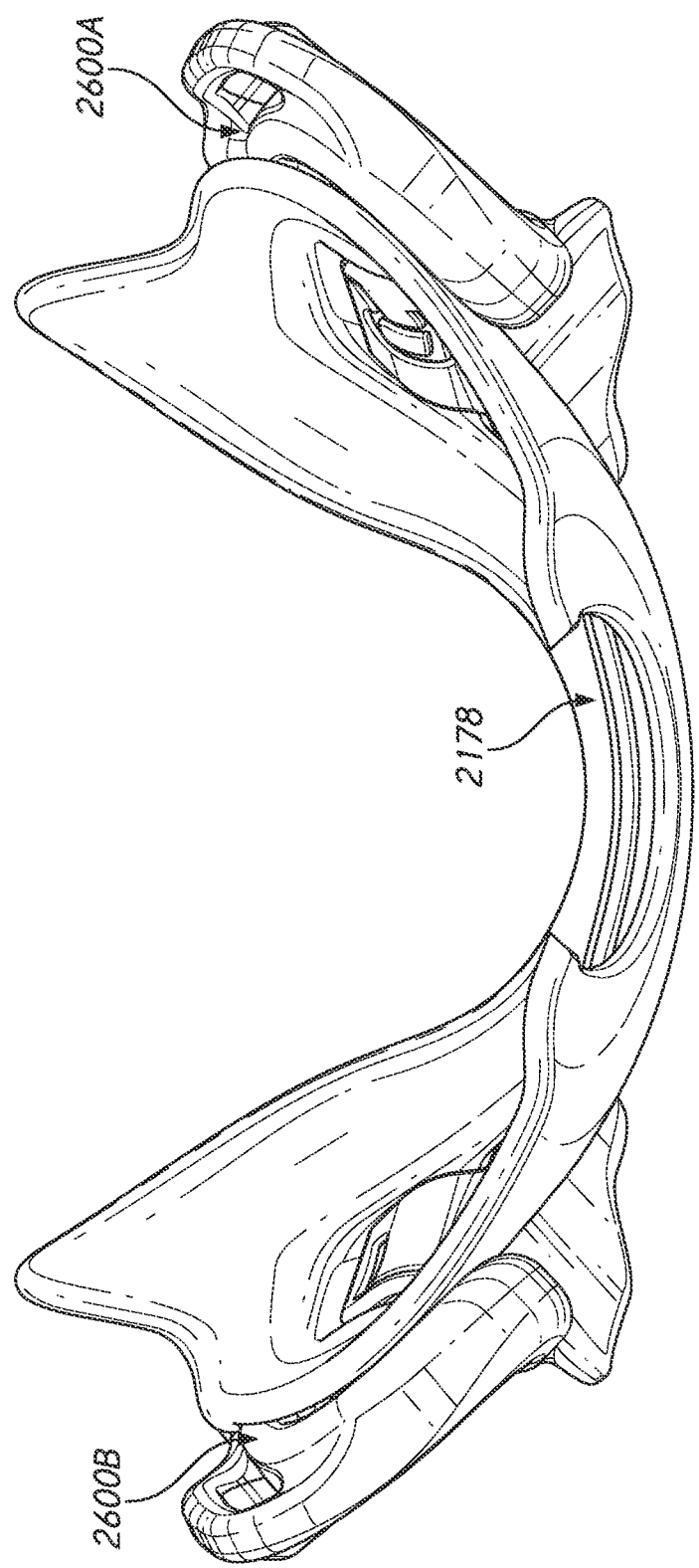
FIG. 43 is a bottom and front perspective view of a frame assembly of the mask assembly of FIG. 34A.

As shown in FIGS. 37A and 37B, the first and second headgear clips 2600A, 2600B can include a hook 2654. The hook 2654 can form a tongue that protrudes rearwardly and laterally from a rear portion of the finger grip 2642 towards a center of the aperture 2606. For example, the hook 2654 can extend inwardly into the aperture 2606. In some configurations, during assembly, the hook 2654 can slide under at least a portion of the clip retention features 2550 (e.g., the raised edge 2572). In some configurations, the hook 2654 can include a raised lip 2652. The raised lip 2652 can extend along an inner edge of the hook 2654. The raised lip 2652 can engage with at least a portion of the clip retention features 2550 (e.g., the post 2576). Thus, the hook 2654 can secure the first and second headgear clips 2600A, 2600B to the frame 2178.

In some configurations, at least one of the first and second headgear clips 2600A, 2600B includes a keying notch 2650. The keying notch 2650 can form a recess, for example, along an edge of at least one of the first and second headgear clips 2600A, 2600B. For example, the keying notch 2650 can be positioned along a rear surface of at least one of the first and second headgear clips 2600A, 2600B. The keying notch 2650 can correspond with and/or receive the keying bump 2570 of the frame 2178 such that the headgear clip sits substantially flush with the front surface of the frame 2178 when the headgear clip is connected to the frame 2178. For example, as shown in FIG. 36B, a left headgear clip can include the keying notch 2650. The keying notch 2650 can correspond to the keying bump 2570 positioned on the left lateral side of the frame 2178. The keying notch 2650 can indicate to the user that the headgear clip 2600 is a left headgear clip 2600B or a right 2600A, for example. In such configurations, the keying notch 2650 may desirably prevent the headgear clips 2600 from connecting to the incorrect clip retention feature 2550.

Figure 44:
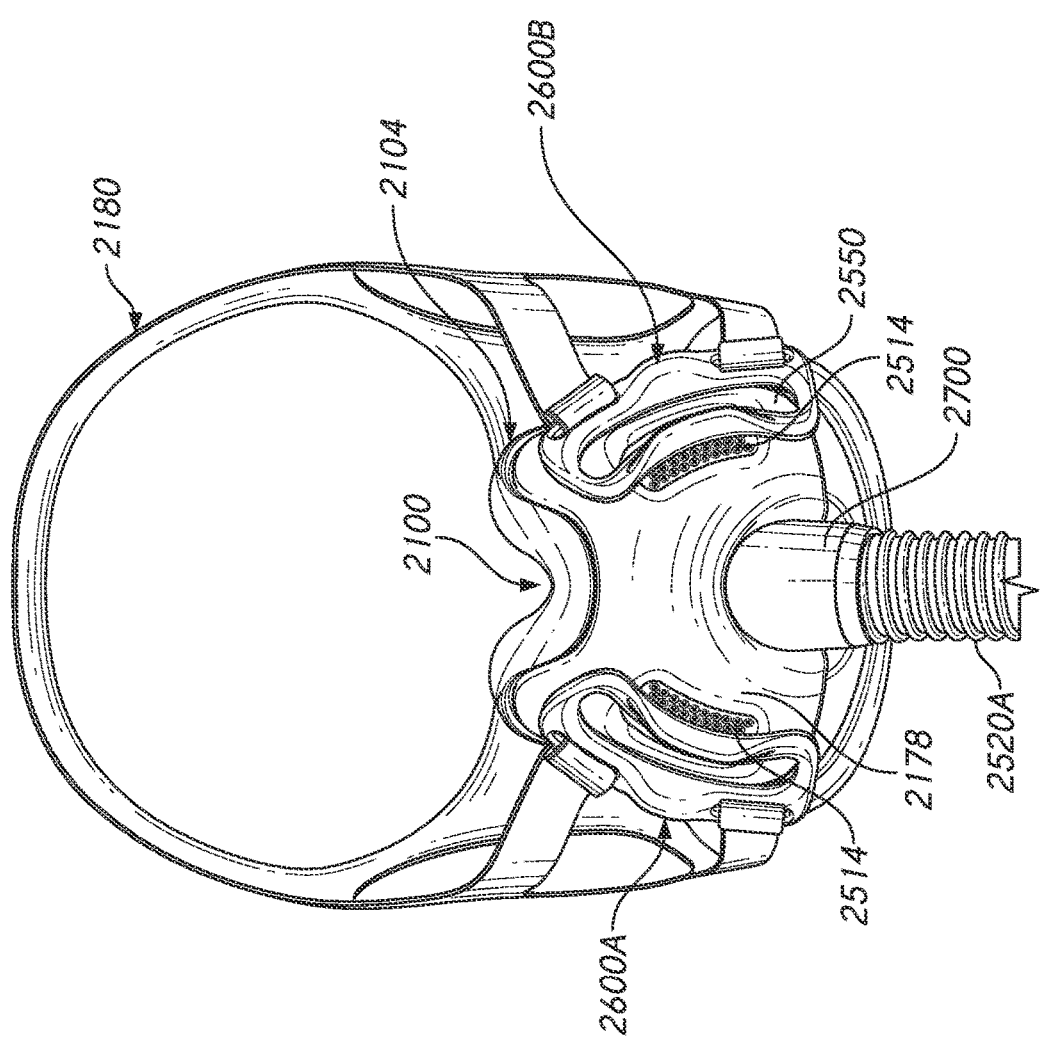
FIG. 44 is a front view of an interface assembly illustrating clip retention features and vent features.
Figure 45:
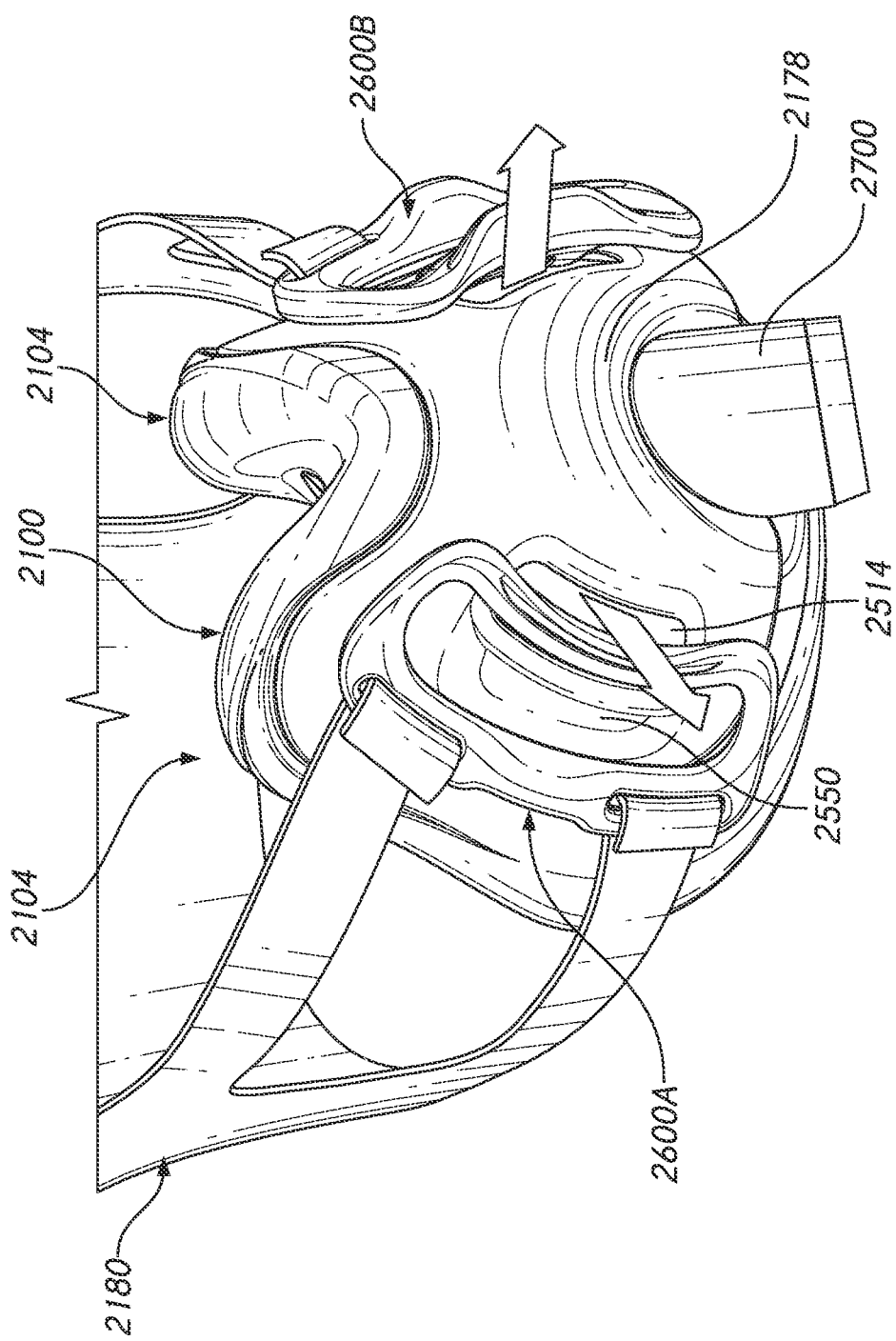
FIG. 45 is a front and side perspective view of the interface assembly of FIG. 44 illustrating clip retention features and vent features.

FIGS. 44-45 illustrate an embodiment of the interface assembly. As shown in FIGS. 44-45, the interface can include a headgear assembly 2180 and a mask assembly 2100. The mask assembly 2100 can include a mask seal 2104, a frame 2178, and an air supply conduit 2520A. As shown in the illustrated example, the frame 2178 can include a conduit connection 2700. The conduit connection 2700 can provide a direct connection between the frame 2178 and the air supply conduit 2520A. For example, the conduit connection 2700 can form a substantial portion of the lower region of the housing 2102. For example, the conduit connection 2700 can extend laterally substantially between opposite clip retention features 2550. In some configurations, the conduit connection 2700 can be angled downwardly away from the frame 2178.

As shown in FIGS. 44-45, the frame can include at least one vent aperture 2514. For example, the vent aperture 2514 can be preferably provided within the mask assembly 2100 such that the vent aperture 2514 aligns with an opening in the frame 2178 and/or between various components of the mask assembly 2100. For example, the vent aperture 2514 can be provided between the frame 2178 and the headgear clips 2600A, 2600B. In some configurations, the vent aperture 2514 defines an opening provided between the frame 2178 and the headgear clips 2600A, 2600B. In some configurations, the vent aperture 2514 can form at least a portion of the clip retention features 2550 (e.g., at least a portion of the aperture of the clip retention features 2550. For example, the vent aperture 2514 can define a portion of the aperture of the clip retention features 2550 that is not covered by the headgear clips 2600 when the headgear clips 2600 are connected to the frame 2178. Such configurations can desirably disperse the exhausted air over a greater area and in at least two directions away from the user's face to reduce drafts against the user's face when worn.

In some arrangements, the vent aperture 2514 can advantageously allow exhausted air, as discussed above, to pass through the frame 2178 to the atmosphere. In some configurations, the vent apertures 2514 can be positioned along lateral sides of the mask frame 2178 and can face outwardly away from a central portion of the frame 2178. For example, as shown in FIG. 45, exhausted air can pass through the frame 2178 and laterally away from the user when the user wears the mask assembly 2100. As described above, such configurations can desirably disperse the exhausted air over a greater area and in at least two directions away from the user's face to reduce drafts against the user's face when worn.

FIGS. 46-48 illustrate an embodiment of the interface assembly that includes similar or identical features and/or components as the interface assembly discussed above, in many aspects. As shown in FIGS. 46-48, the vent aperture 2514 can be centrally positioned in the frame 2178, as discussed above. In some configurations, the vent aperture 2514 can be formed in at least a portion of the conduit connection 2700. For example, the vent aperture 2514 can be formed in an upper portion of the conduit connection 2700. As shown in FIG. 46, for example, the conduit connection 2700 can be integrally formed with the frame 2178. In some configurations, the conduit connection 2700 can be formed directly in the housing 2102.

In some configurations, as shown in FIG. 46, the headgear clips 2600 can provide support to the mask seal 2104. In such configurations, the frame 2178 may not provide support to the paddles 2126 of the mask seal 2104. For example, the headgear clips 2600 can be provided to the front surface of the mask seal 2104 such that the headgear clips 2600 provide sufficient mechanical rigidity and structure to hold the shape of the mask seal 2104 when the mask seal 2104 is worn by a user. For example, the headgear clips 2600 can help to prevent ballooning of the mask seal 2104. As shown in FIG. 46, the headgear clips can extend vertically along lateral sides of the mask seal 2104. For example, the headgear clips 2600 can extend along a substantial portion of the lateral sides of the mask seal 2104. When connected to the frame 2178, the headgear clips 2600 can extend upwardly along the front surface of the mask seal 2104 and can cover at least a portion of the mask seal 2104. Such configurations can desirably support the mask seal 2104 and can reduce the overall size of the frame 2178. Thus, such configurations can reduce the bulkiness of the mask assembly 2100.

FIGS. 47 and 48 illustrate various configurations of the headgear clips 2600. In some configurations, the headgear clip 2600 can have a rounded and/or an elliptical cross-section (see FIG. 48). In such configurations, the rounded surfaces of the headgear clip 2600 can provide an appearance that is aesthetically pleasing to the user. For example, the rounded surfaces of the headgear clip 2600 can allow the headgear clip 2600 to appear smaller to the user and/or reduce the overall bulkiness of the headgear clip 2600. In some configurations, the headgear clip 2600 can include a squared and/or substantially rectangular cross-section (see FIG. 47). In such configurations, the squared surfaces of the headgear clip 2600 can provide surfaces that are easier to grip compared to other shaped cross-sections.

Figure 49:
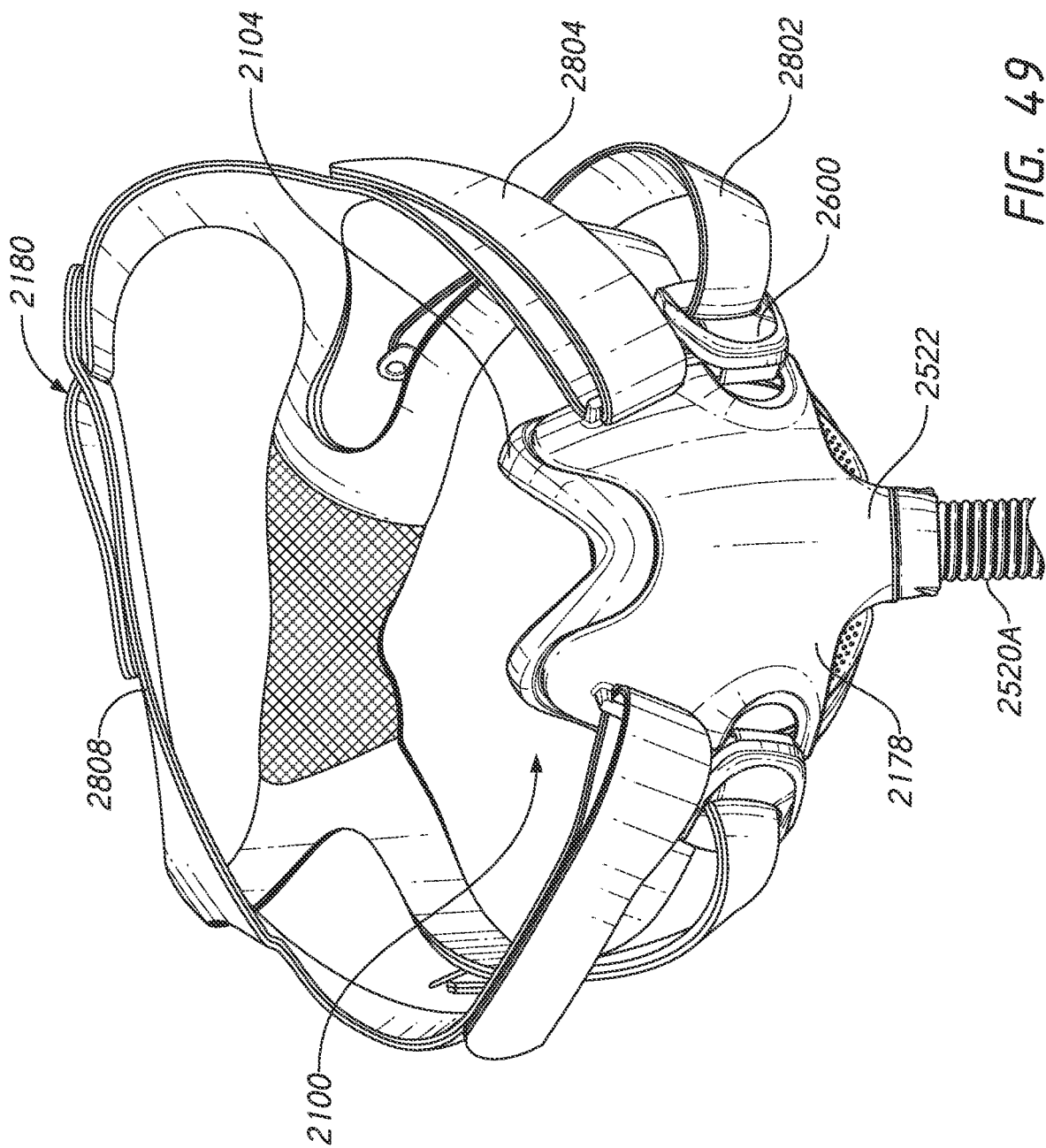
FIG. 49 is a front and top perspective view of an interface assembly.
Figure 56:
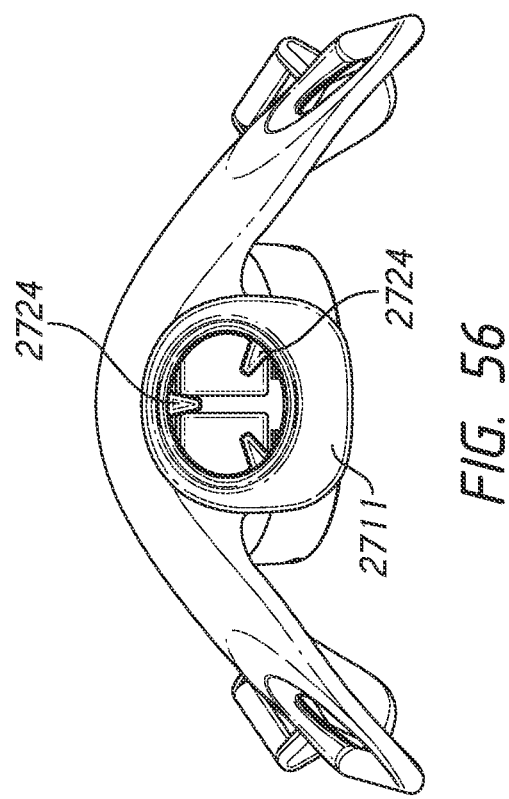
FIG. 56 is a bottom view of the frame of the mask assembly of FIG. 50A.

FIGS. 49-75 illustrate an embodiment of the interface assembly. As shown in FIG. 49, the interface assembly can include a headgear assembly 2180, a frame 2178, a mask assembly 2100 and an air supply conduit 2520A, among other possible components. The headgear assembly 2180 can include straps, such as one or more upper side straps 2804, one or more lower side straps 2802, and/or a crown strap 2808, among other components (see FIGS. 73-75). The mask assembly 2100 can include a mask housing 2012 and a mask seal 2104 that form a breathing chamber, among other possible components. As shown in the illustrated example and as explained in more detail below, the frame 2178 can include an anti-asphyxia (A-A) valve assembly 2522B. In some configurations, the valve assembly 2522B can be received by the valve recess 2726, as discussed below. As described in more detail below, the valve assembly 2522B can include a valve housing 2522 (referred to herein as the "valve 2522"). The valve 2522 can be integrally formed with the frame 2178. As described below, the valve assembly 2522B can include at least a portion of the frame 2178, the valve 2522, a valve element or valve member, such as a valve flap 2524, and/or a tube connector 2711, among other possible components. The valve 2522 can be located within the frame 2178 adjacent the air supply conduit 2520A. In some embodiments, the valve 2522 of the valve assembly 2522B can include an inlet tube 2522A. The inlet tube 2522A can be positioned rearward of the front wall of the frame 2178. In some embodiments, the inlet tube 2522A can define at least a portion of a gas flow passage. In some configurations, the integration of the valve 2522 with the frame 2178 can allow the air supply conduit 2520A to extend in a generally downward direction from a lower front portion of the frame 2178. Such configurations can reduce the overall bulkiness of the patient interface. For example, in such configurations, the conduit 2520A can be positioned closer to the user in use. The gas flow passage is provided by the gas supply conduit 2520A, valve assembly 2522B and the cushion connector 2708. The gas flow passage provides a passage through which pressurized gas is delivered to the users nose and/or mouth via the mask assembly 2100.

FIGS. 50A-50B illustrate an example of the mask assembly 2100. As mentioned above, the mask assembly 2100 can include the mask seal 2104 and housing 2012, and is assembled to the frame 2178 and/or the air supply conduit 2520A, among other components. The frame 2178 can be generally curved in a lateral and/or a vertical direction.

In some embodiments, the frame 2178 can be provided to a front side of the mask seal 2104. In some embodiments, the frame 2178 can cover a substantial portion of the front side of the mask seal 2104, such as a substantial portion of a housing 2102 of the mask seal 2104. In some embodiments, the frame 2178 is centered in the lateral direction along the front surface of the mask seal 2104. For example, the entire front surface of the frame 2178 can be positioned forward of the mask seal 2104.

FIGS. 51A-59 illustrate an embodiment of the frame 2178. In some embodiments, the frame 2178 can include a cushion connector 2708, an inlet or inlet opening 2706, the valve 2522, at least one upper strap connector 2702, at least one lower strap connector 2704, and/or paddles 2179.

In some embodiments, the cushion connector 2708 can be positioned on a rear side of the frame 2178. In some embodiments, the cushion connector 2708 is unitary with the frame 2178 and extends rearwardly from a rear surface of a front wall of the frame 2178. The cushion connector 2708 can provide a fluid connection between the inlet 2706 and the mask assembly 2100.

In some embodiments, the cushion connector 2708 can be shaped to fit into at least a portion of the mask assembly 2100 to connect the frame 2178 to the mask assembly 2100. For example, the cushion connector 2708 can fit into at least a receiving portion of the mask housing 2102 portion of the mask assembly 2100. The cushion connector 2708 can include a somewhat rounded 'D' shape, a rounded trapezoidal shape, circular shape, elliptical shape and/or oval shape, among other possible shapes.

In some embodiments, the cushion connector 2708 is in the form of a protruding wall that forms a cuff or collar. The protruding wall can extend rearwardly and/or upwardly from the rear side of a front wall portion 2701 of the frame 2178. The cushion connector 2708 can be positioned above the A-A valve 2522 along the rear side of the frame 2178. The cushion connector 2708 can be positioned adjacent the A-A valve 2522 along the rear side of the frame 2178. In some configurations, the inlet 2706, the A-A valve 2522 and the cushion connector 2708 cooperate to form a gases flow passage defined by the frame 2178. In the illustrated arrangement, each of the inlet 2706, the A-A valve 2522 and the cushion connector 2708 includes a substantially enclosed space (with the exception of specific and deliberate openings) that defines a portion of the overall gases flow passage. In some configurations, the front wall portion 2701 of the frame 2178 defines at least a portion of the gases flow passage. In the illustrated arrangement, the front wall portion 2701 of the frame 2178 defines a portion of the gases flow passage in one or both of the A-A valve 2522 and the cushion connector 2708. Such an arrangement allows the frame 2178 to have a reduced depth in comparison to designs in which an entirety of the gases flow passage is defined by dedicated structure.

In some embodiments, the cushion connector 2708 can include an alignment feature, such as an alignment notch 2710. The alignment notch 2710 can be formed in a portion of the cushion connector 2710. For example, the alignment notch 2710 can be formed in an upper wall portion of the cushion connector 2708. The alignment notch 2710 can guide the connection between the frame 2178 and the mask assembly 2100. For example, the alignment notch 2710 can correspond to a feature on the mask assembly 2100 to allow the frame 2178 and the mask assembly 2100 to be connected in a proper orientation. In some embodiments, the alignment notch 2710 has a generally trapezoidal shape, rectangular shape, and/or square shape, among other possible shapes. In some embodiments, the alignment notch 2710 can have a width at an outer edge of the upper wall of the cushion connector 2708 that is wider than a width of the alignment notch 2710 at a position closer to the rear side of the frame 2178.

In some embodiments, the frame 2178 can include the inlet 2706. The inlet 2706 can be defined by a tube connector 2711, which can be a separate structure that is coupled to the frame 2178. In some embodiments, the inlet 2706 can provide a fluid flow path or gases flow passage through which pressurized air can be provided to the mask assembly 2100. In some embodiments, the pressurized air can be provided to the mask assembly 2100 through the inlet 2706 via the A-A valve 2522 or past the A-A valve 2522. As explained in more detail below, the A-A valve 2522 can provide access to atmospheric air when there is no pressurized air source or when the pressure within the mask assembly 2100 otherwise drops below atmospheric pressure.

In some embodiments, the frame 2178 can include at least one upper strap connector 2702 and at least one lower strap connector 2704. In the illustrated arrangement, the frame 2178 includes a pair of upper strap connectors 2702 and a pair of lower strap connectors 2704. each of the pair of the upper and lower strap connectors 2702, 2704 can be positioned on opposite lateral sides of the frame 2178. In some embodiments, the upper strap connectors 2702 can slidably receive the corresponding upper headgear straps 2802 of the headgear 2180 (e.g., see FIG. 49). The upper headgear connectors 2702 can include a post 2703A and an aperture 2703B. The post 2703A can be spaced away from a front surface of the frame 2178. The post 2703A can be positioned at approximately a center of the aperture 2703B. In some embodiments, the post 2703A can be positioned offset from the center of the aperture 2703B. In some embodiments, the post 2703A can be positioned offset forward of a front wall of the frame 2178.

Figure 73:
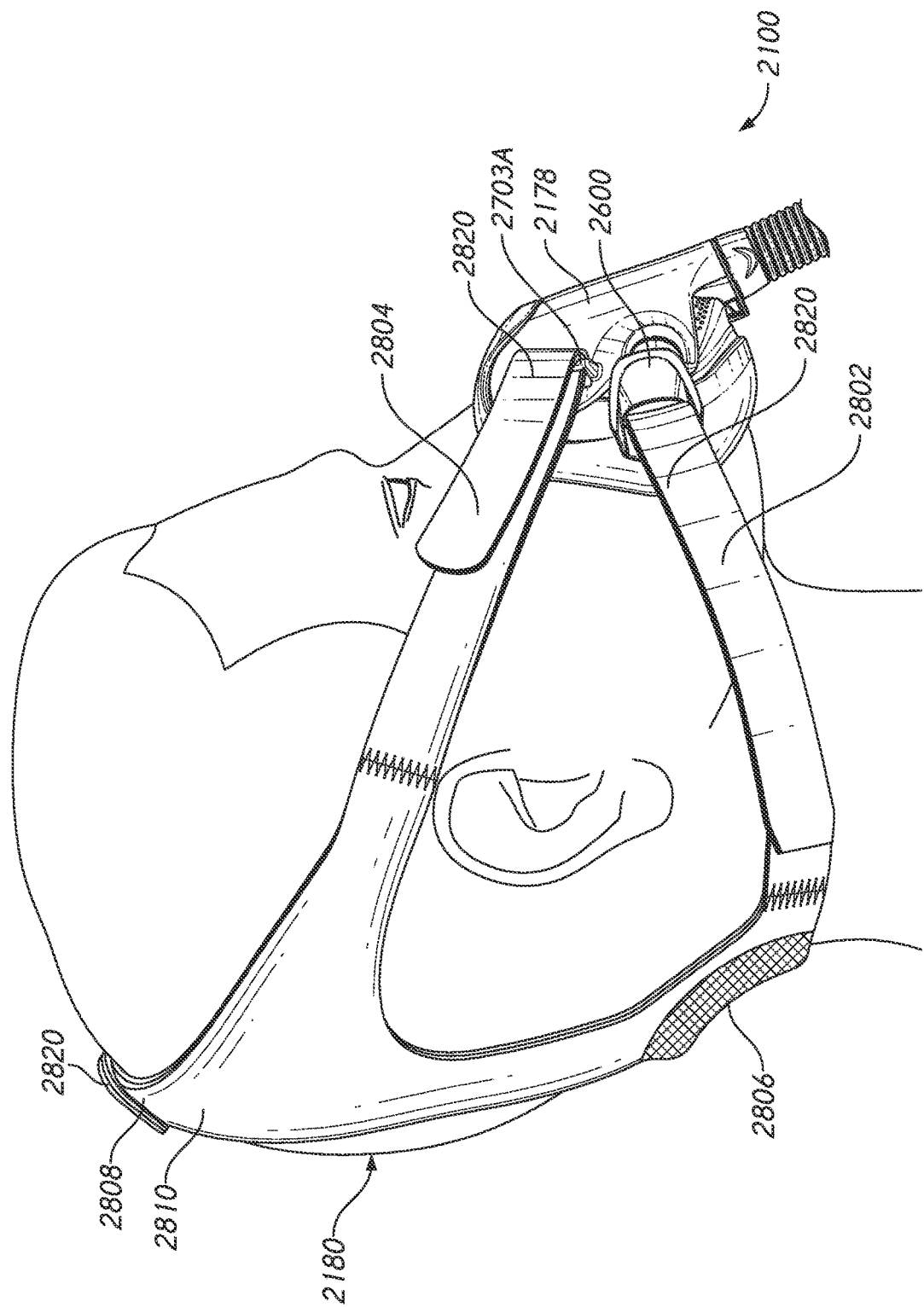
FIG. 73 is a side view of an interface assembly showing a headgear assembly.

As shown in at least FIGS. 49 and 73 the post 2703A can help to secure the upper side strap 2802 to the upper headgear connector 2702. In some embodiments, the post 2703A together with the front surface of the frame 2178 can define a slot through which the corresponding upper side strap 2802 can pass. For example, the upper side strap 2802 can pass through the slot formed between the post 2703A and the aperture 2703B. Once the upper side strap 2802 passes through the slot, the upper side strap 2802 can be wrapped around an outer side of the post 2703A and folded over on itself, for example. In some embodiments, the aperture 2703B can provide additional space to allow the upper side strap 2802 to pass behind the post 2703A. In some configurations, the aperture 2703B can help to decrease a distance between the post 2703A and the front surface of the frame 2178 necessary to accommodate the thickness of the strap 2802. In some embodiments, the upper strap connectors 2702 can secure, such as removably secure, a headgear clip that can be attached to the upper side straps 2802.

In some embodiments, the lower strap connector 2704 can receive and/or secure the lower side strap 2802 and/or a lower headgear clip 2600 (see FIG. 49). As shown in at least FIGS. 51A-54, the lower strap connector 2704 can include a lower post 2705A. The lower post 2705A can be positioned along a side edge of the frame 2178. The lower post 2705A can be spaced away from a portion of the frame 2178 to define an aperture 2705B. In some embodiments, the lower post 2705A forms a lower lateral edge of the frame 2178. In some embodiments, the aperture 2705B can be shaped to receive at least a portion of the lower headgear clip 2600. In some embodiments, the aperture 2705B can be substantially D-shaped, among other possible shapes. In some embodiments, the post 2705A can be received within and/or retain a portion of the corresponding lower headgear clip 2600, such as a hook portion of the clip 2600. The lower post 2705A can provide a removable connection between the lower side straps 2802 and the frame 2178 and/or the lower headgear clips 2600 and the frame 2178.

In some embodiments, the frame 2178 can include the frame paddles 2179. As described above, the paddles 2179 can define upper support members that provide support to forward facing lateral sides (seal paddles 2126) of a nasal region 2168 of the mask seal 2104 when assembled. The paddles 2179 can help to minimize deflection of the mask seal 2104. In some embodiments, the paddles 2179 can help to maintain contact between the nasal region 2168 and the user's nose. For example, the paddles 2179 can help to prevent the nasal region 2168 and seal paddles 2126 of the mask seal 2104 from inflating away from and/or disengaging from the user's nose.

FIGS. 52-58 illustrate certain portions of the valve 2522 in greater detail. As shown in at least FIGS. 52-54, the valve 2522 can include a valve element or valve member, such as a valve flap 2524. The valve 2522 can also include a tube connector 2711, among other possible components. In some embodiments, the valve 2522 can include vent paths 2722 and/or outlets 2720. As illustrated, at least a portion or some components of the valve 2522 can be integrally formed with the frame 2178. For example, the body portions that define the gases flow passage(s) of the valve 2522 are integrally formed with the frame 2178. Some configurations can desirably reduce assembly time and/or reduce the number of components necessary to manufacture, clean and/or replace. Some such configurations can desirably reduce the likelihood that pressurized air will leak from the assembly.

Figure 55:
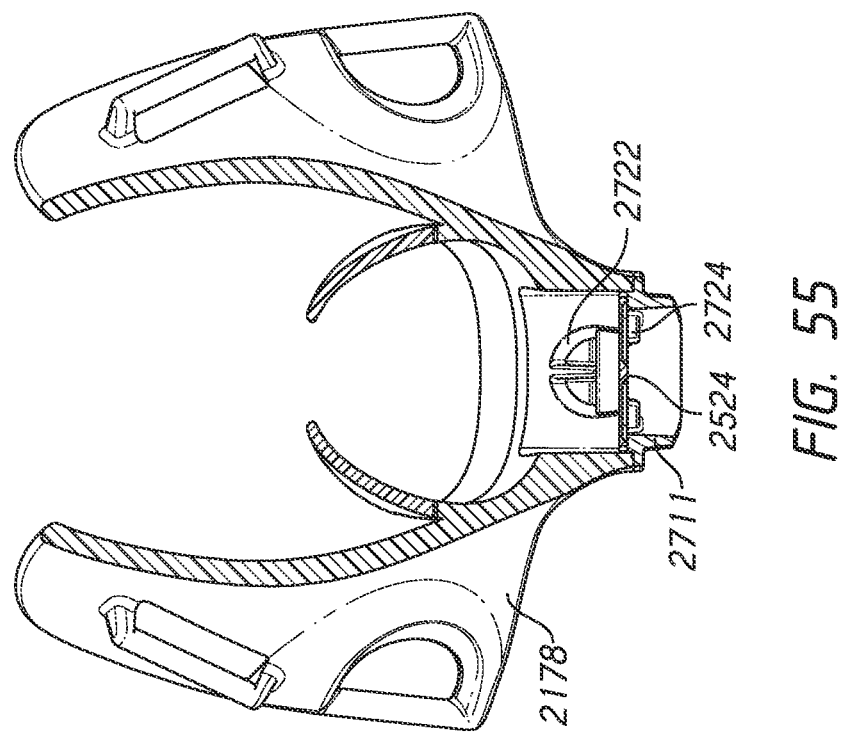
FIG. 55 is a front cross-sectional view of the frame of the mask assembly of FIG. 50A taken along the line 55-55 of FIG. 52.

FIG. 53 and FIG. 54 illustrate side cross-sectional views of the frame 2178 along the lines 53-53 and 54-54 shown in FIG. 51A, respectively. FIG. 55 illustrates a front cross-sectional view of the frame 2178 shown in FIG. 52. As illustrated, the frame 2178 can house the valve flap 2524. In some embodiments, the frame 2178 entirely surrounds the valve flap 2524. As such, the valve flap 2524 can be positioned to fit within a gases flow passage of the valve 2522 of the frame 2178.

In some embodiments, the tube connector 2711 can define the inlet opening 2706 that directs pressurized air through the valve 2522 to the user through the mask assembly 2100. In some embodiments, the tube connector 2711 can be elliptical shaped, circular shaped, and/or oval shaped, among other shapes. Preferably, a dimension of the inlet 2706 in a forward-rearward direction is smaller than a dimension of the inlet 2706 in a lateral direction. Accordingly, extra space is provided to accommodate the valve 2522 in a forward-rearward direction in comparison to a design in which the inlet 2706 is circular without increasing the forward-rearward dimension of the frame 2178 or moving the inlet 2706 further away from the user's face. The tube connector 2711 can include a male component that is received by a corresponding female connector. The female connector may be attached to the conduit 2520A. In some embodiments, the tube connector 2711 can allow for disconnection of the conduit 2520A by twisting the conduit 2520A relative to the frame 2178 and/or the tube connector 2711. In some embodiments, the conduit 2520A is connected to the tube connector 2711 by a snap-fit configuration, among other possible configurations. For example, the tube connector 2711 can include one or more tube connector notches 2712. The tube connector notches 2712 can engage corresponding features on the conduit 2520A via the snap-fit configuration.

In some embodiments, the valve flap 2524 can be secured within the frame 2178 by the tube connector 2711. In some embodiments, the tube connector 2711 can be permanently connected to a lower end of the frame 2178 that defines the valve 2522 by various configurations, such as welding, adhesive, and/or a snap-fit configurations, among other possible configurations. In some embodiments, the tube connector 2711 can surround and/or secure a tab of the valve flap 2524 between the lower end of the frame 2178 and a flange of the tube connector 2711. In some embodiments, the valve flap 2524 can be positioned adjacent an inner end 2711A of the tube connector 2711 within the frame 2178. In some embodiments, the valve flap 2524 can be constructed in whole or in part from a flexible elastomer, such as silicone, among other materials.

The valve flap 2524 can open and close different flow paths within the valve 2522 to allow air to flow through a desired one of the different flow paths of the valve 2522. For example, when a flow generator supplies positive pressure air to the user through the mask assembly 2100, the valve flap 2524 can pivot about a hinge or otherwise move in response to the pressurized air entering the inlet 2706. In this position, the valve flap 2524 is opened relative to the inlet 2706 of the tube connector 2711, and is closed relative to the valve 2522 and/or vent paths 2722 of the valve 2522. Some configurations can help to ensure that all or substantially all of the positive pressure airflow is directed to the user with little to no airflow leaking from the vent paths 2722 of the valve 2522. When a flow generator does not provide airflow to the mask assembly 2100 or the pressure within the mask assembly 2100 otherwise drops below atmospheric pressure, the valve flap 2524 closes relative to the inlet 2706 of the tube connector 2711 and the vent paths 2722 of the A-A valve 2522 are opened to allow the user in inhale ambient air through the valve 2522.

The tube connector 2711 can support the valve flap 2524 in an operable position relative to the valve 2522 portion of the frame 2178. In some configurations, the tube connector 2711 defines a stop that prevents the valve flap 2524 from inverting or extending downwardly out of the inlet 2706 of the frame 2178 (see, e.g. FIG. 53). In some configurations, the tube connector 2711 can include a flap support 2724. In some embodiments, the tube connector 2711 can include at least three flap supports 2724 (see FIG. 56). In some embodiments, the tube connector 2711 can includes at least two, three, four, five, or six or more flap supports 2724. The flap supports 2724 can extend radially inwardly from an inner surface of a perimeter wall of the tube connector 2711 into the inlet 2706 of the tube connector 2711. In some embodiments, the flap supports 2724 can be positioned adjacent an upper edge of the tube connector 2711. In some configurations, the flap supports 2724 can prevent the valve flap 2524 from inverting or extending downwardly into the inlet 2706.

As shown in at least FIG. 55, the valve 2522 (alone, or in combination with the frame 2178) can include various vent paths and valve outlets to allow air to flow in and out of the mask assembly 2100 when the valve flap 2524 is in the closed position. For example, in some embodiments, a flow path is provided through the vent paths 2722 and valve outlets 2720 of the valve assembly 2522B and the cushion connector 2708. In some embodiments, the valve 2522 can include at least two vent paths 2722 and/or at least two lateral valve outlets 2720.

Figure 59:
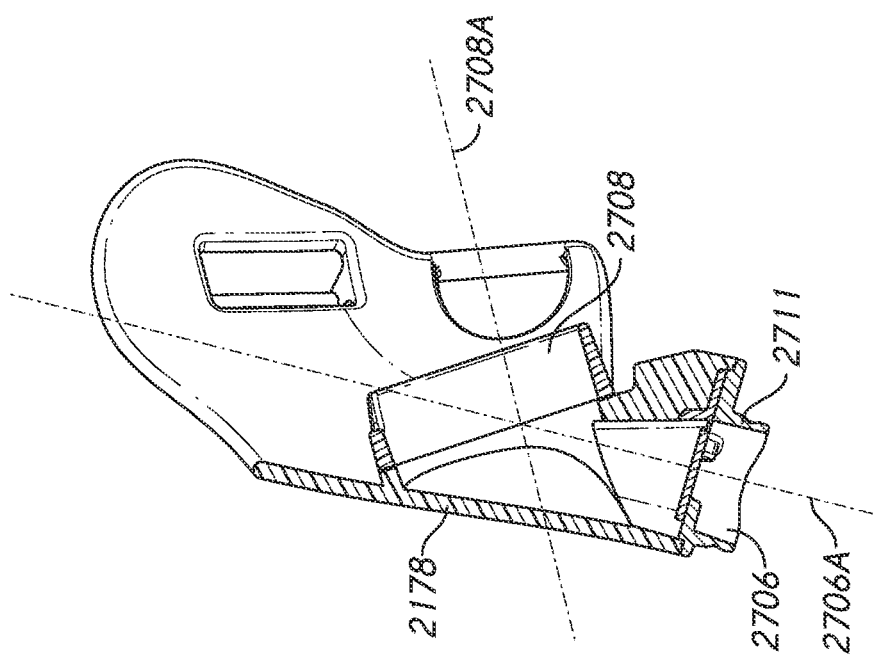
FIG. 59 is a side cross-sectional view of the frame of the mask assembly of FIG. 50A showing an inlet axis and a cushion connector axis.

In some embodiments, the vent paths 2722 can extend rearwardly away from the inlet 2706 towards the outlets 2720. In some embodiments, the vent paths 2722 can extend through an internal wall of the valve 2522 towards the outlets 2720. In some embodiments, the vent paths 2722 can extend from the tube 2520A through an internal wall of the valve 2522 towards the outlets 2720. In some embodiments, the vent paths 2722 can extend rearwardly and downwardly into the outlets 2720. In some embodiments, a central axis of the vent paths 2722 forms an acute angle with the central axis 2706A (as shown in FIG. 59) of the inlet 2706.

In some embodiments, the outlets 2720 can define an opening to allow exhausted air to pass out of the patient interface or inhaled air to enter the patient interface, via the vent paths 2722 when the valve flap 2524 is in the closed position. As shown in FIG. 54, the valve 2522 can include a rear wall 2523 that is spaced rearwardly away from an outlet of the vent paths 2722 at the outlets 2720 and defines the outlets 2720 along with an internal wall. Such configurations can provide a space to direct the exhausted air in a lateral direction, as indicated by arrows shown in Figure MB. The rear wall of the valve 2522 can allow the exhausted air to be directed away from the user. In some embodiments, the lateral direction can help to minimize contact between the exhausted air and the user. Some configurations can help to reduce discomfort caused to the patient by the exhausted air. In some embodiments, the outlets 2720 can extend below a lower surface of the housing 2102 when assembled (see FIGS. 68-70). In such configurations, the exhausted air may not be blocked by the housing 2102.

Figure 58:
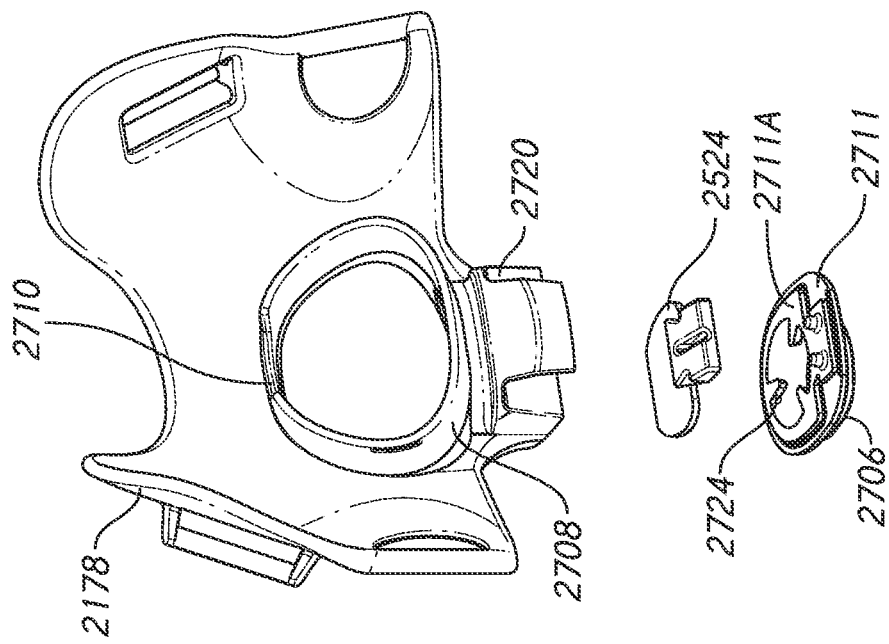
FIG. 58 is a rear, bottom, and side perspective exploded view of the frame of the mask assembly of FIG. 50A.
Figure 57:
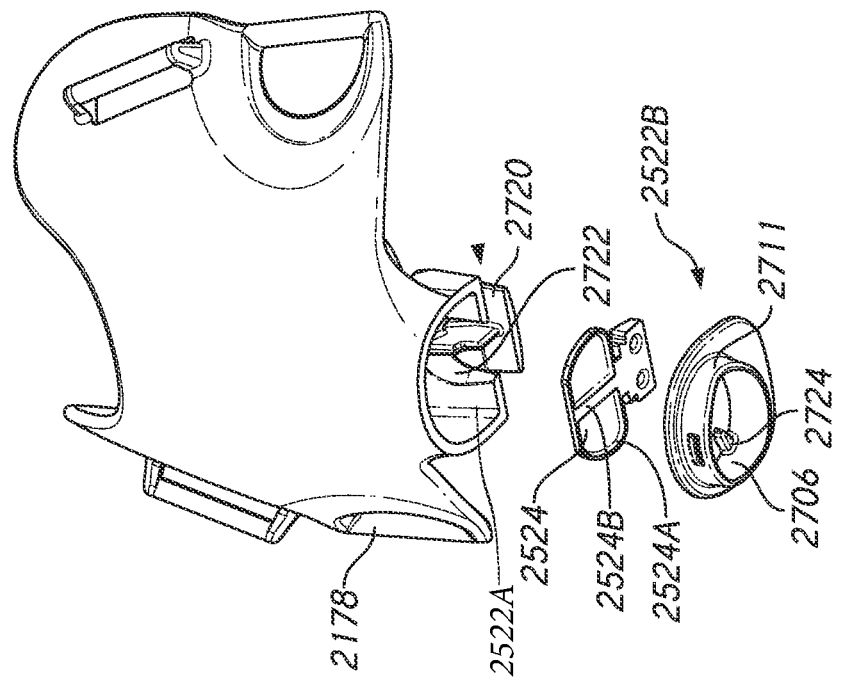
FIG. 57 is a front, bottom, and side perspective exploded view of the frame of the mask assembly of FIG. 50A.

FIGS. 57 and 58 illustrate exploded views of the frame 2178 showing portions of the valve 2522. In some embodiments, the valve flap 2524 can include an outer perimeter 2524A and an interior rib 2524B. The outer perimeter 2524A can include a lip. The lip can define a thickened region that extends along the outer perimeter 2524A. In some embodiments, the rib 2524B can be positioned along a lower side of the valve flap 2524. The rib 2524B can be positioned approximately along a central axis of the valve flap 2524. In some embodiments, the rib 2524B can define a thickened region along the center of the valve flap 2524. In some embodiments, the outer perimeter 2524A and/or the rib 2524B can provide rigidity to the valve flap 2524. The outer perimeter 2524A and/or the rib 2524B can help to inhibit ballooning and/or deformation of the valve flap 2524 caused by the pressurized airflow in use. Some configurations can help to provide an effective seal around the vent paths 2722 when the valve 2522 is in the opened position.

In some embodiments, the tube connector 2711 can define the inlet 2706 that directs a source of pressurized air through the valve 2522 into the breathing chamber. The inlet 2706 can be angled downwards in use. For example, as shown in FIG. 59, a central axis 2706A of the inlet 2706 can form an angle with a central axis 2708A of the cushion connector 2708. In some embodiments, the angle is approximately 125 degrees. In some embodiments, the angle is greater than or less than 125 degrees. In some embodiments, the angle is approximately 124.4 degrees. In some embodiments, the angle is greater than or less than 124.4 degrees. Some configurations can help to keep the conduit 2520A away from the user. Some configurations can desirably minimize the bulkiness of the patient interface, such as at the front of the mask assembly 2100.

FIGS. 60-72B illustrate an embodiment of the mask assembly 2100 coupled to the frame 2178. As described previously herein, the mask assembly 2100 can include a housing 2102 and a mask seal 2104. The housing 2102 can be located on the front side of the mask seal 2104. In some embodiments, the housing 2102 can be substantially rigid. In some embodiments, the housing 2102 can include a frame connector 2730, at least one bias vent 2502, and/or an A-A valve recess 2726.

Figures 61, 62:
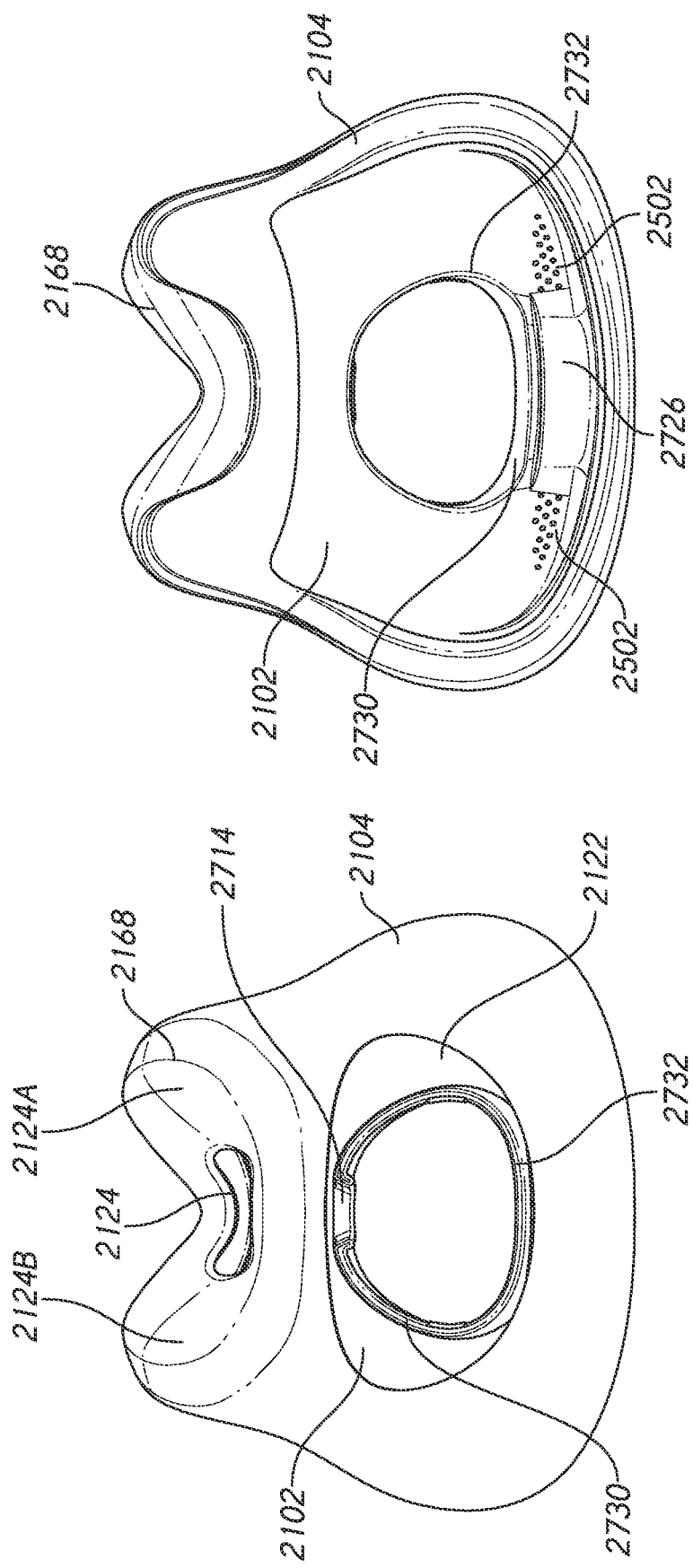
FIG. 61 is a rear view of the mask seal of the mask assembly of FIG. 50A.
FIG. 62 is a front view of the mask seal of the mask assembly of FIG. 50A.
Figure 64:
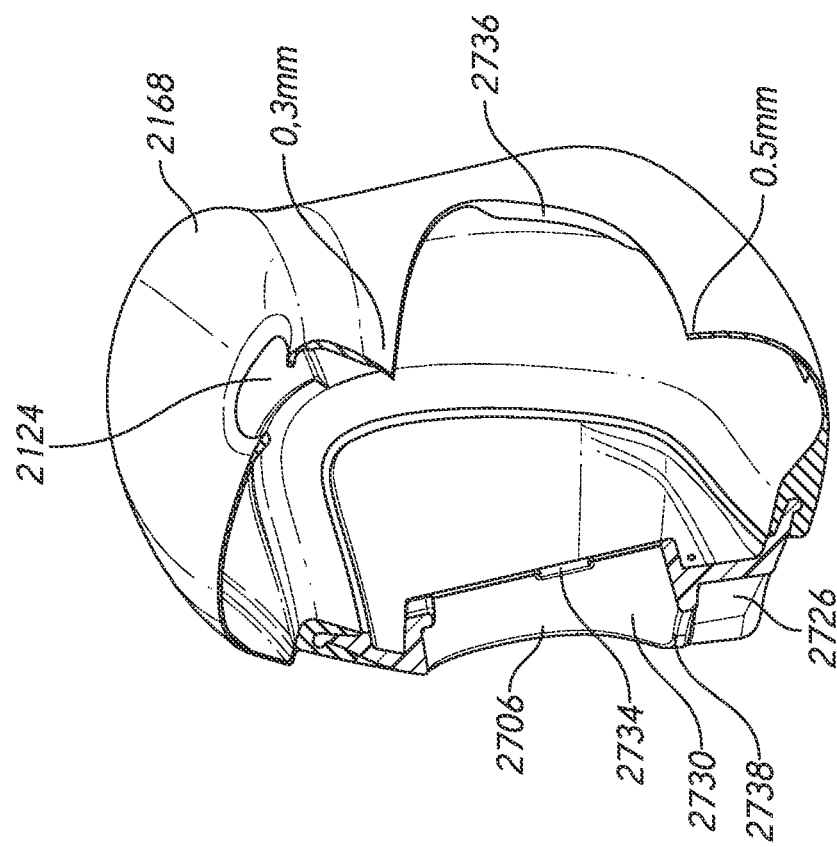
FIG. 64 is a side cross-sectional view of the mask seal of the mask assembly of FIG. 50A.
Figure 63:
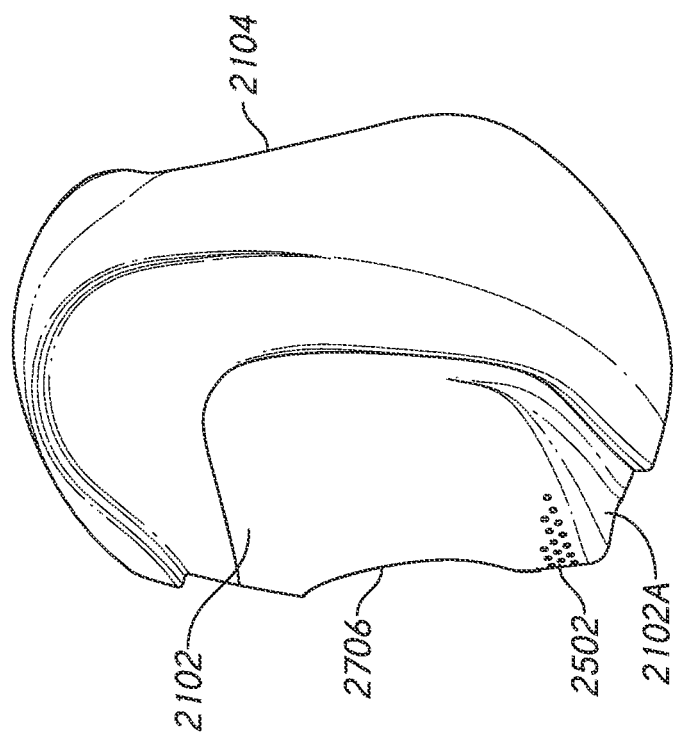
FIG. 63 is a side view of the mask seal of the mask assembly of FIG. 50A.

FIG. 62 illustrates a front view of the mask assembly 2100 showing the housing 2102. In some embodiments, the housing 2102 can include one, two, three, four, or five, or more bias vents 2502. The bias vents 2502 can be positioned at a bottom region of the housing 2102. In some embodiments, the bias vents 2502 can be positioned on a generally forward facing surface of the housing 2102. For example, the bias vents 2502 can be positioned adjacent a lower edge of the housing 2102. In some configurations, holes of the bias vents 2502 can be positioned close to and/or adjacent the lower edge of the frame 2178 when assembled. Preferably, the bias vents 2502 are positioned below a lower edge of the frame 2178. Such configurations can minimize contact between vented air and the frame 2178. Such configurations can help to reduce noise and/or undesirable drafts or air leaks.

FIG. 62 shows an example of the housing 2102 including two bias vents 2502. The bias vents 2502 can include a plurality of holes. The plurality of holes can be arranged in a generally triangular pattern, among other possible patterns. The bias vents 2502 can be positioned on opposing lateral sides of an inlet 2732 and/or valve recess 2726 of the mask seal 2104. In some embodiments, at least a portion of the bias vents 2502 is positioned below at least a portion of the inlet 2732 and at least a portion of the bias vents 2502 is positioned beyond a side of the inlet 2732. In such configurations, only a portion of the bias vents 2502 is positioned laterally beyond the inlet 2732. In some embodiments, the bias vents 2502 are positioned entirely beyond a side of the inlet 2732. The bias vents 2502 can help to disperse the exhausted air. Such configurations can reduce disturbance, such as draft and/or noise, caused by the exhausted air to the user and/or the user's bed partner.

Figure 68:
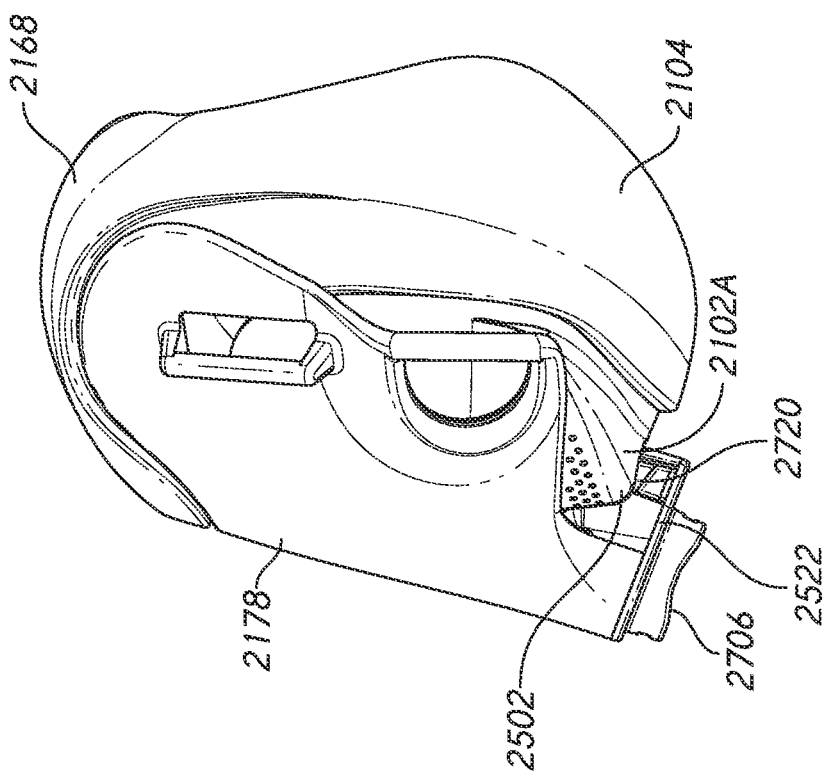
FIG. 68 is a side view of the mask assembly of FIG. 50A.
Figure 71:
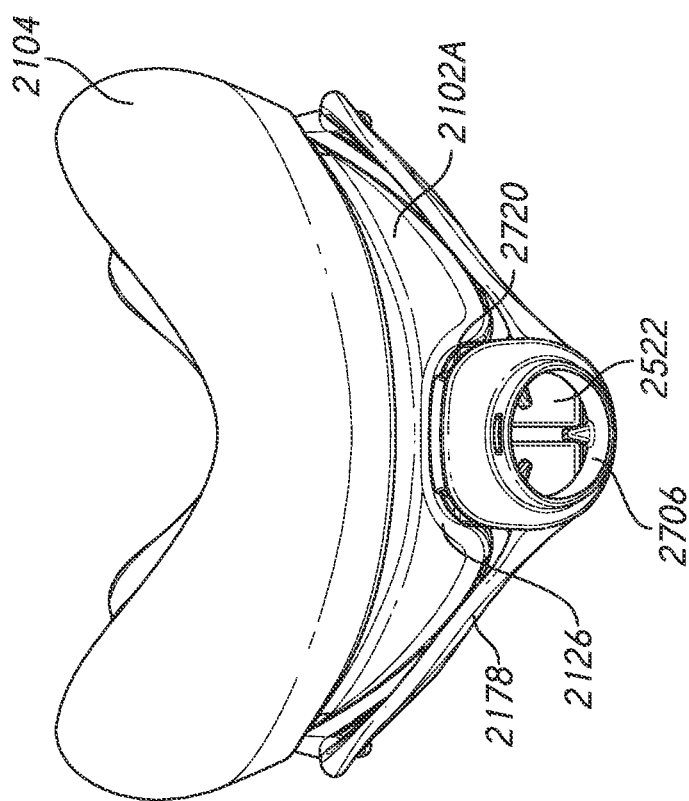
FIG. 71 is a bottom view of the mask assembly of FIG. 50A.

In some embodiments, the bias vents 2502 are positioned such that air is exhausted below the frame 2178 (see FIGS. 68-70). For example, the bias vents 2502 are positioned immediately below and/or adjacent a lower edge of the frame 2178. Such configurations can allow vented air to pass the frame 2178 with minimal disturbance to airflow. As discussed above, such configurations can help to disperse the exhausted air, reduce noise, and/or reduce disturbance caused by the exhausted air to the user and/or the user's bed partner.

In some embodiments, the housing 2102 includes the valve recess 2726. The valve recess 2726 can define a concave region. The concave region can be positioned below and/or adjacent the inlet 2732. In some embodiments, the valve recess 2726 can have a width that is less than a maximum width of the inlet 2732.

In some embodiments, the valve recess 2726 can receive at least a portion of the valve assembly 2522B, such as a rear portion of the valve 2522 and/or the valve outlets 2720. In some embodiments, the valve recess 2726 has a curved surface that includes a curvature accommodating or matching a curvature of a rear surface/wall 2523 of the valve 2522. In at least some embodiments, the valve recess 2726 allows the valve 2522 to be positioned recessed into the mask assembly 2100 and/or below at least a portion of the mask seal 2104, such as a forward upper portion and/or the nasal region 2168 of the mask seal 2104. In at least some embodiments, the valve recess 2726 and/or the valve 2522 can desirably reduce an overall depth of the patient interface. This can help to reduce the obtrusiveness of the patient interface to the user and reduce hose pull. In at least some embodiments, the valve recess 2726 and/or the valve 2522 can allow the valve 2522 to be positioned higher relative to the bottom of the mask seal 2104 and/or the inlet 2732 to be shorter. This can help to reduce the overall size of the mask assembly 2100.

Figure 60:
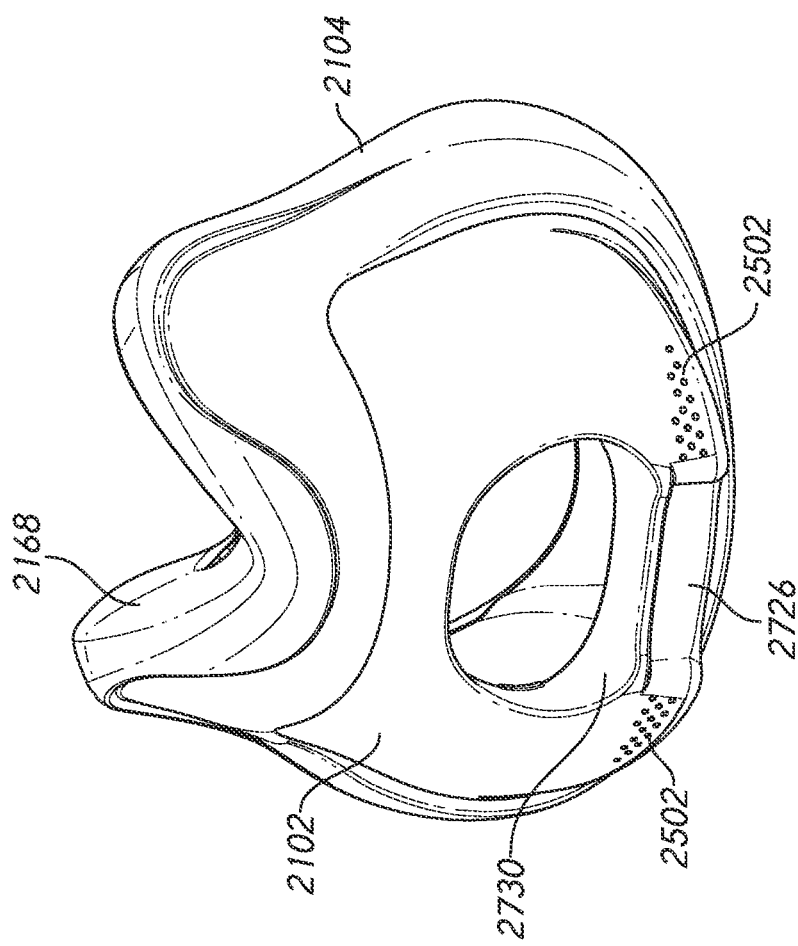
FIG. 60 is a front, top, and side perspective view of a mask seal of the mask assembly of FIG. 50A.

As mentioned above, the housing 2102 can include the frame connector 2730. As shown in FIG. 60, the frame connector 2730 can form a collar. The collar can protrude inwardly from a front surface of the housing 2102 toward or into an interior of the mask assembly 2100. The frame connector 2730 can extend around all or a portion of a perimeter of the inlet 2730. In some embodiments, the frame connector 2730 can receive and/or retain the cushion connector 2708 of the frame 2178.

In some embodiments, the frame connector 2730 can include a securement feature to engage the cushion connector 2708 of the frame 2178. For example, the frame connector 2730 can include at least one connector bump 2734 (e.g., a pair of connector bumps 2734) or other retention or alignment features. The connector bump 2734 can be positioned along a portion of an interior surface of the frame connector 2730. The connector bump 2734 can engage with a corresponding engagement feature 2715 of the cushion connector 2708. The engagement feature 2715 can include a notch, recess, or other engagement feature. The engagement feature 2715 can be positioned on an outer surface of the cushion connector 2708. In some embodiments, the connector bump 2734 can engage with the engagement feature 2715 of the cushion connector 2708 by a snap-fit arrangement, among other engagement arrangements. In some embodiments, the cushion connector 2708 includes a pair of laterally opposed recesses 2715 that are configured to receive and/or retain a corresponding pair of connector bumps 2734 on the frame connector 2730. Such configurations can secure the frame 2178 to the mask seal 2104.

Figure 69:
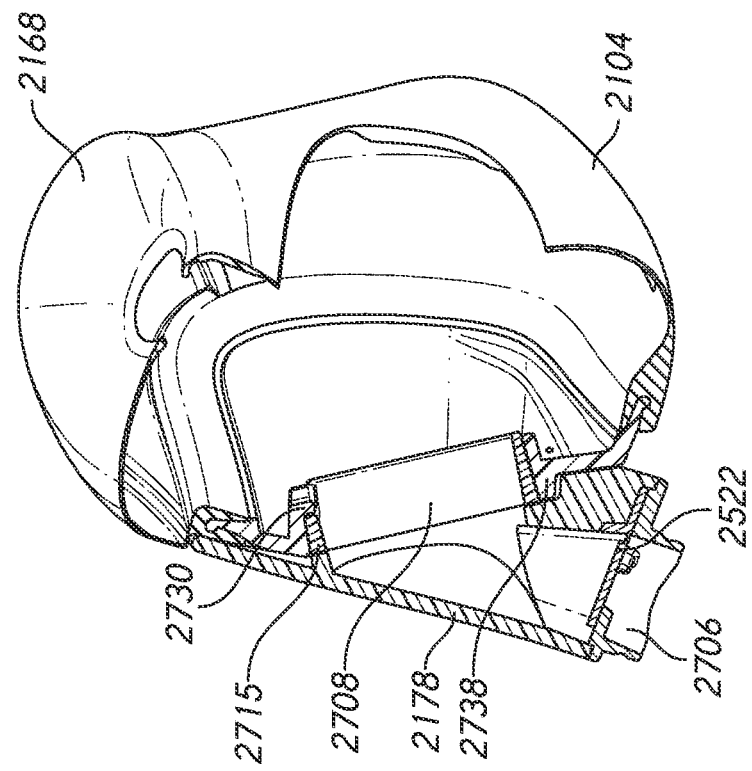
FIG. 69 is a side cross-sectional view of the mask assembly of FIG. 50A.
Figure 70:
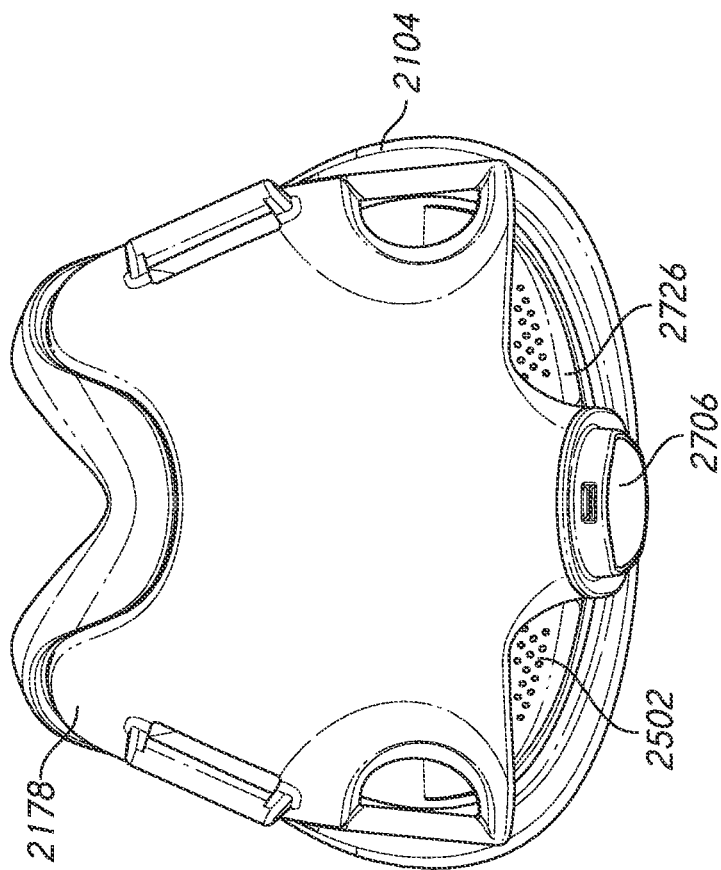
FIG. 70 is a front view of the mask assembly of FIG. 50A.
Figure 72A:
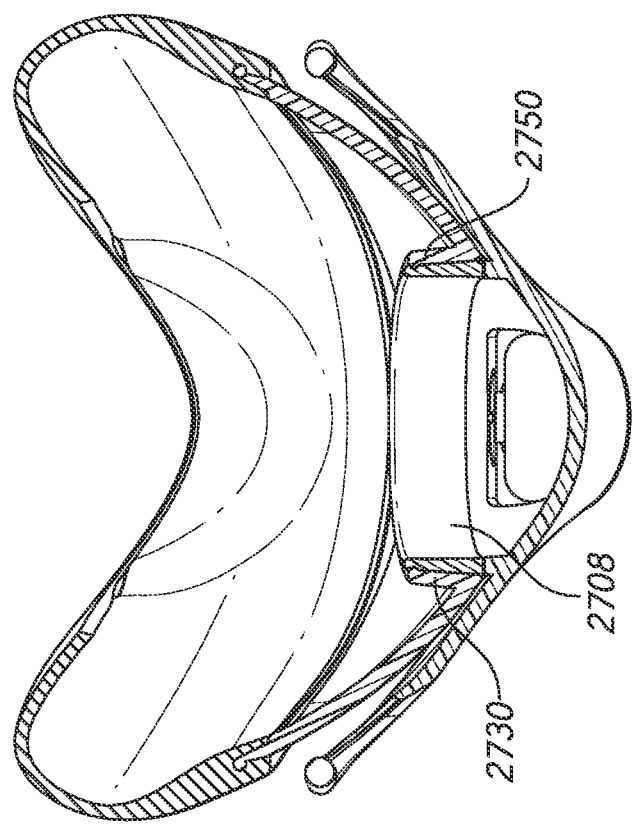
FIG. 72A is a top cross-sectional view of the mask assembly of FIG. 50A.
Figure 72B:
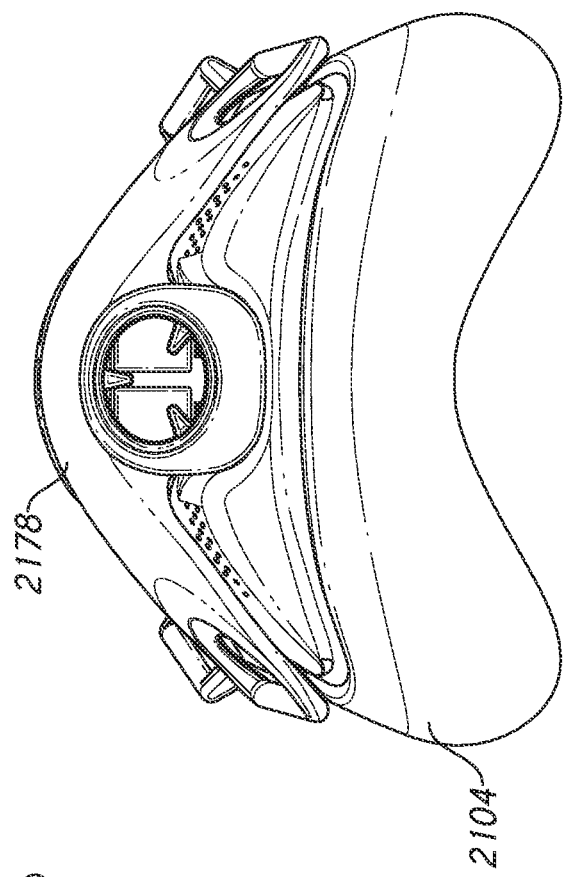
FIG. 72B is a bottom view of the mask assembly of FIG. 50A.

As shown in at least FIG. 61, in some embodiments, the frame connector 2730 can include a lip 2738 (see FIG. 69). The lip 2738 can define an upper wall of the valve recess 2726. In some configurations, the lip 2738 can be positioned recessed relative to a front side of the housing 2102. In some embodiments, the lip 2738 can form at least a portion of the frame connector 2730 and/or the inlet 2732. When assembled, the lip 2738 can be positioned above the valve outlet 2720.

In some embodiments, the frame connector 2730 can include an alignment feature 2714. The alignment feature 2739 can protrude radially into the inlet and/or forward of a rear edge of the frame connector 2730. The alignment feature 2714 can engage with the alignment notch 2710 of the cushion connector 2708 of the frame 2178. Such configurations can help to align and/or secure the frame 2178 to the mask seal 2104.

In some embodiments, the mask seal 2104 is substantially resilient. In some embodiments, the mask seal 2104 can include a nasal region 2168 and an oral seal portion. The nasal region 2168 can include a nasal opening 2124 and right and left nasal sealing surfaces 2124A, 2124B. The right and left nasal sealing surfaces 2124A, 2124B can extend outwardly from the nasal opening 2124. In some embodiments, the oral seal portion can include an oral opening 2122 (see FIG. 61).

As shown in at least FIGS. 61-62, the mask seal 2104 can include the inlet 2732. The inlet 2732 can form an opening in the mask seal 2104 to allow air to flow to and from the breathing chamber. In some embodiments, the inlet 2732 can include a non-circular perimeter. In some embodiments, the perimeter of the inlet 2732 is generally oval-shaped, elliptical-shaped, square-shaped, and/or rectangular-shaped, among other shapes. In some embodiments, the inlet 2732 includes a generally rounded 'D' shape and/or a rounded trapezoidal shape, among other shapes. The inlet 2732 having a non-circular perimeter can desirably help to more easily assemble and/or align the frame 2178 and the mask seal 2104. Such configurations can help to prevent incorrect assembly of the seal 2104 to the frame 2178. Such configurations can help to inhibit or limit rotation of the frame 2178 relative to the seal 2104 when assembled. In some embodiments, the non-circular perimeter of the inlet 2732 can allow at least a portion of the valve 2522 to be positioned closer to a center of the inlet 2732 than a design having a circular inlet 2732. Such non-circular configurations can desirably create additional space for the valve 2522, thereby reducing the overall size (e.g., height) of the mask assembly 2100 when assembled in comparison to a mask having a circular inlet.

As discussed above, the mask seal 2104 can include the nasal region 2168. The nasal region 2168 can include left and right sealing surfaces 2124B, 2124A. In some embodiments, each of the left and right sealing surfaces 2124B, 2124A can define a convex region. As described previously herein, the left and right sealing surfaces 2124B, 2124A cooperate to define a concave region, which is configured to receive the user's nose. The convex region of the left and right sealing surfaces 2124B, 2124A can be generally flattened. For example, the flattened convex region can extend from a top of the left and right sealing surfaces 2124B, 2124A towards the nasal opening 2124. The flattened convex region can have a generally linear profile as the left and right sealing surfaces 2124B, 2124A extends from the uppermost point towards the nasal opening 2124. The flattened sealing surfaces 2124B, 2124A can help to prevent or limit creases forming in the sealing surfaces 2124B, 2124A when the nasal region 2168 engages the user's nose in use, for example. Some configurations can help to minimize leaks around the user's nose in use.

FIG. 65 illustrates a close-up rear view of a portion of the nasal region 2168. Though the left nasal sealing surface 2124B is shown and described, the right nasal sealing surface 2124A can include similar features and, preferably, is a mirror-image of the left nasal sealing surface 2124B. As shown, the nasal sealing surface 2124B can be relatively flat laterally adjacent to the nasal opening 2124. In some embodiments, the curvature of the nasal sealing surface 2124B can be relatively low (e.g., approximately linear) as the nasal sealing surface 2124B extends radially outward from the nasal opening 2124 towards the uppermost point of the nasal sealing surface 2124B. In some embodiments, the curvature of the nasal sealing surface 2124B can be relatively low as the nasal sealing surface 2124B extends radially outward from the nasal opening 2124 to approximately a midpoint 2725 of the nasal sealing surface 2124B, as illustrated by the lines of curvature 2727A, 2727B, 2727C, 2727D, 2727E. In some embodiments, the curvature of the nasal sealing surface 2124B increases as the nasal sealing surface 2124B extends radially outward beyond the midpoint 2725 (e.g., at an outer nasal sealing surface region). As indicated by a curve plot 2728 and as described in more detail below, the radius of curvature of the outer nasal sealing surface region decreases in a rearward to forward direction along the surface of the outer nasal sealing surface region. For example, in some embodiments, the radius of curvature of the outer nasal sealing surface region at the rearward portion of the nasal sealing surface 2124B is larger than the radius of curvature of the outer nasal sealing surface region at the forward portion of the nasal sealing surface 2124B. That is, the nasal sealing surface 2124B can go from less curved to more curved moving in a rearward to forward direction.

Figure 66:
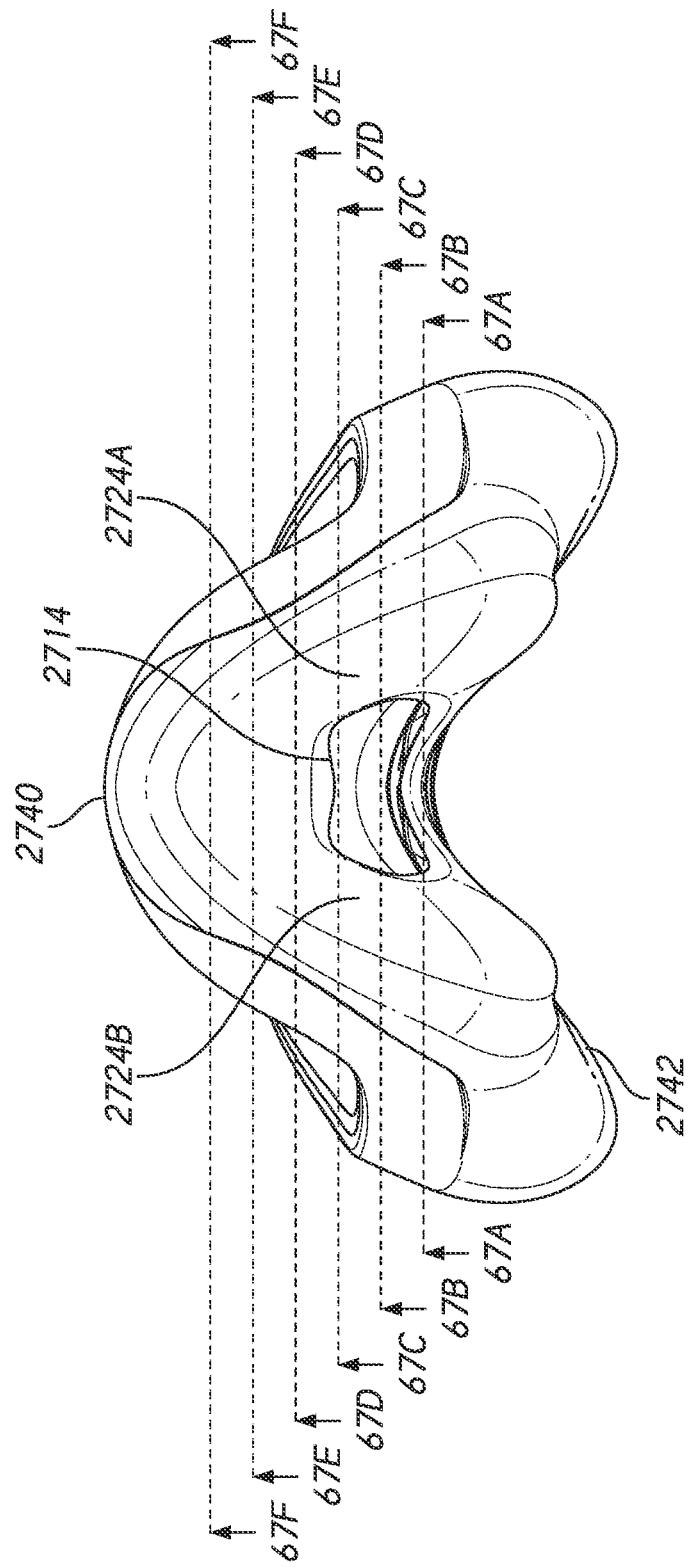
FIG. 66 is a top view of the mask seal of the mask assembly of FIG. 50A.

FIG. 66 shows a top view of the mask seal 2104. FIGS. 67A-67F are sectioned views as viewed from the rear of the mask seal 2104. As shown, in some embodiments, the left and right nasal sealing surfaces 2124B, 2124A can be angled away from each other in at least two dimensions. For example, when viewed from the front or rear, the left and right nasal sealing surfaces 2124B, 2124A can extend upwardly away from the nasal region 2168 at an angle to form a generally v-shape. In some embodiments, when viewed from the top, the left and right nasal sealing surfaces 2124B, 2124A can be angled away from each other in a direction from a front 2740 to a rear 2742 of the mask seal 2104 or seal assembly 2100. In such configurations, the nasal region 2168, including the left and right nasal sealing surfaces 2124B, 2124A can form a generally triangular shape. Such configurations can desirably accommodate or generally match the geometry of a user's nose. This can provide more stability and/or comfort to the user. Such configurations can help to reduce leakages of air from the mask seal 2104.

Figure 67C:
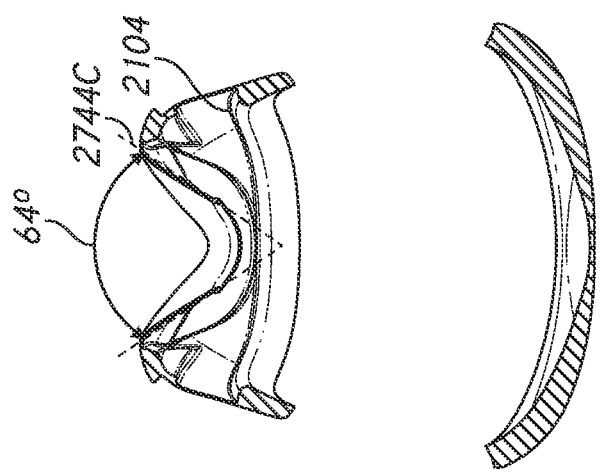
FIG. 67C is a rear cross-sectional view of the mask seal of the mask assembly of FIG. 50A taken along the line 67C-67C of FIG. 66.
Figure 67B:
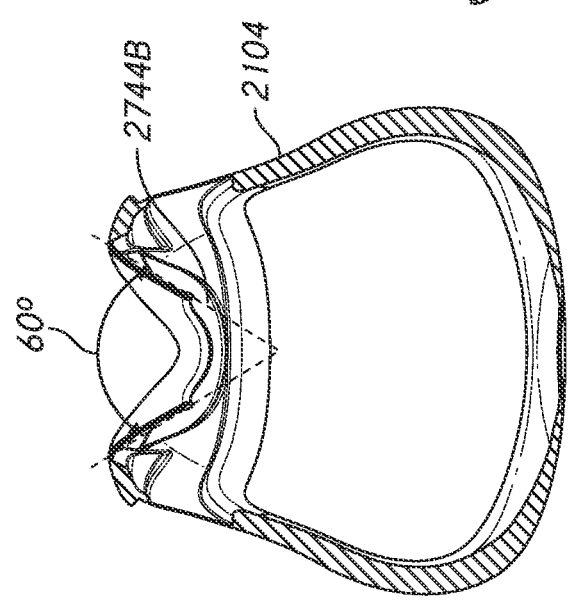
FIG. 67B is a rear cross-sectional view of the mask seal of the mask assembly of FIG. 50A taken along the line 67B-67B of FIG. 66.
Figure 67A:
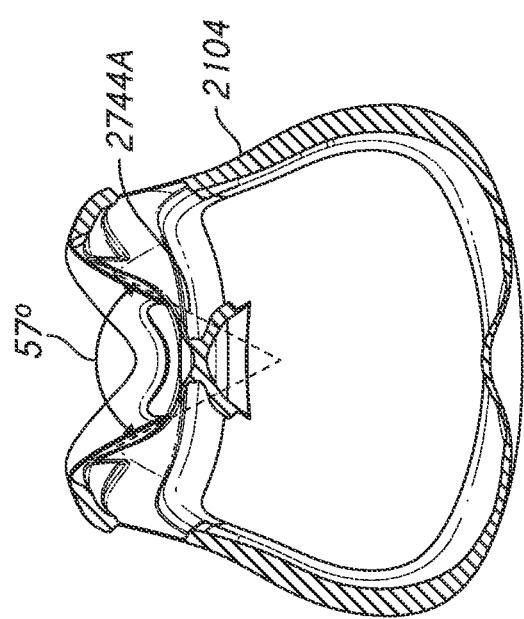
FIG. 67A is a rear cross-sectional view of the mask seal of the mask assembly of FIG. 50A taken along the line 67A-67A of FIG. 66.
Figure 67F:
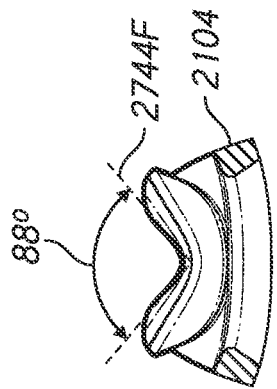
FIG. 67F is a rear cross-sectional view of the mask seal of the mask assembly of FIG. 50A taken along the line 67F-67F of FIG. 66.
Figure 67E:
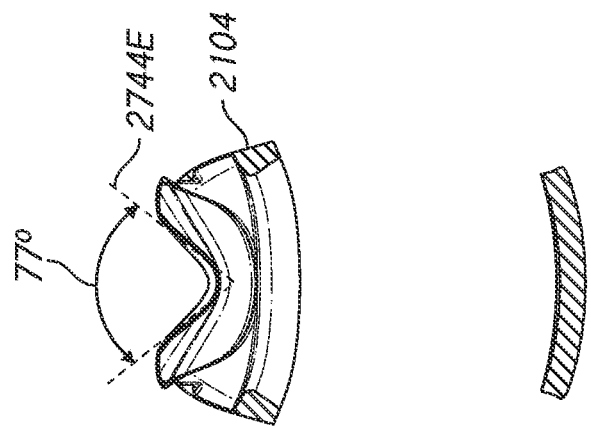
FIG. 67E is a rear cross-sectional view of the mask seal of the mask assembly of FIG. 50A taken along the line 67E-67E of FIG. 66.
Figure 67D:
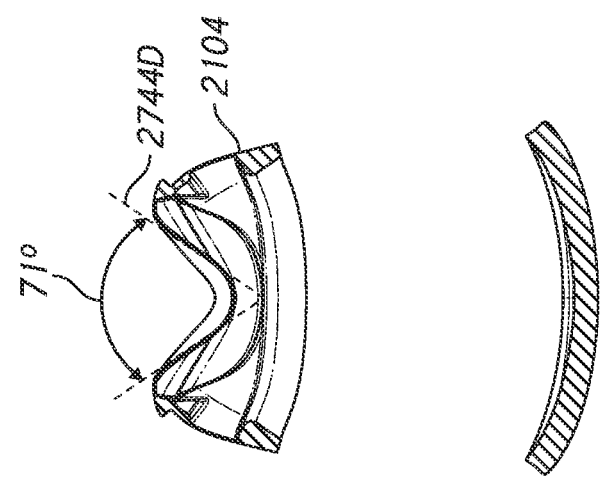
FIG. 67D is a rear cross-sectional view of the mask seal of the mask assembly of FIG. 50A taken along the line 67D-67D of FIG. 66.

FIG. 67A illustrates a rear cross-sectional view taken along line A-A of FIG. 66. FIG. 67B illustrates a rear cross-sectional view taken along line B-B of FIG. 66. FIG. 67C illustrates a rear cross-sectional view taken along line C-C of FIG. 66. FIG. 67D illustrates a rear cross-sectional view taken along line D-D of FIG. 66. FIG. 67E illustrates a rear cross-sectional view taken along line E-E of FIG. 66. FIG. 67F illustrates a rear cross-sectional view taken along line F-F of FIG. 66. As shown in FIGS. 67A-67F, the left and right nasal sealing surfaces 2124B, 2124A of the nasal region 2168 can be angled outwardly and upwardly away from each other, and from the central vertical plane, in a bottom to top direction. In some embodiments, an angle between the left and right nasal sealing surfaces 2124B, 2124A increases in a rear to front direction. In some embodiments, a depth of the nasal region 2168 decreases in a rear to front direction. For example, the angle 2744A can be approximately 57 degrees, the angle 2744B can be approximately 60 degrees, the angle 2744C can be approximately 64 degrees, the angle 2744D can be approximately 71 degrees, the angle 2744E can be approximately 77 degrees, the angle 2744F can be approximately 88 degrees, and angles therebetween such ranges. Such configurations can allow the nasal region 2168 to engage with the user's nose in use without extending over the tip of the user's nose. Such configurations can desirably better match the geometry of a user's nose. This can provide more stability and/or comfort to the user. Such configurations can help to reduce leakages of air from the mask seal 2104.

Figure 74:
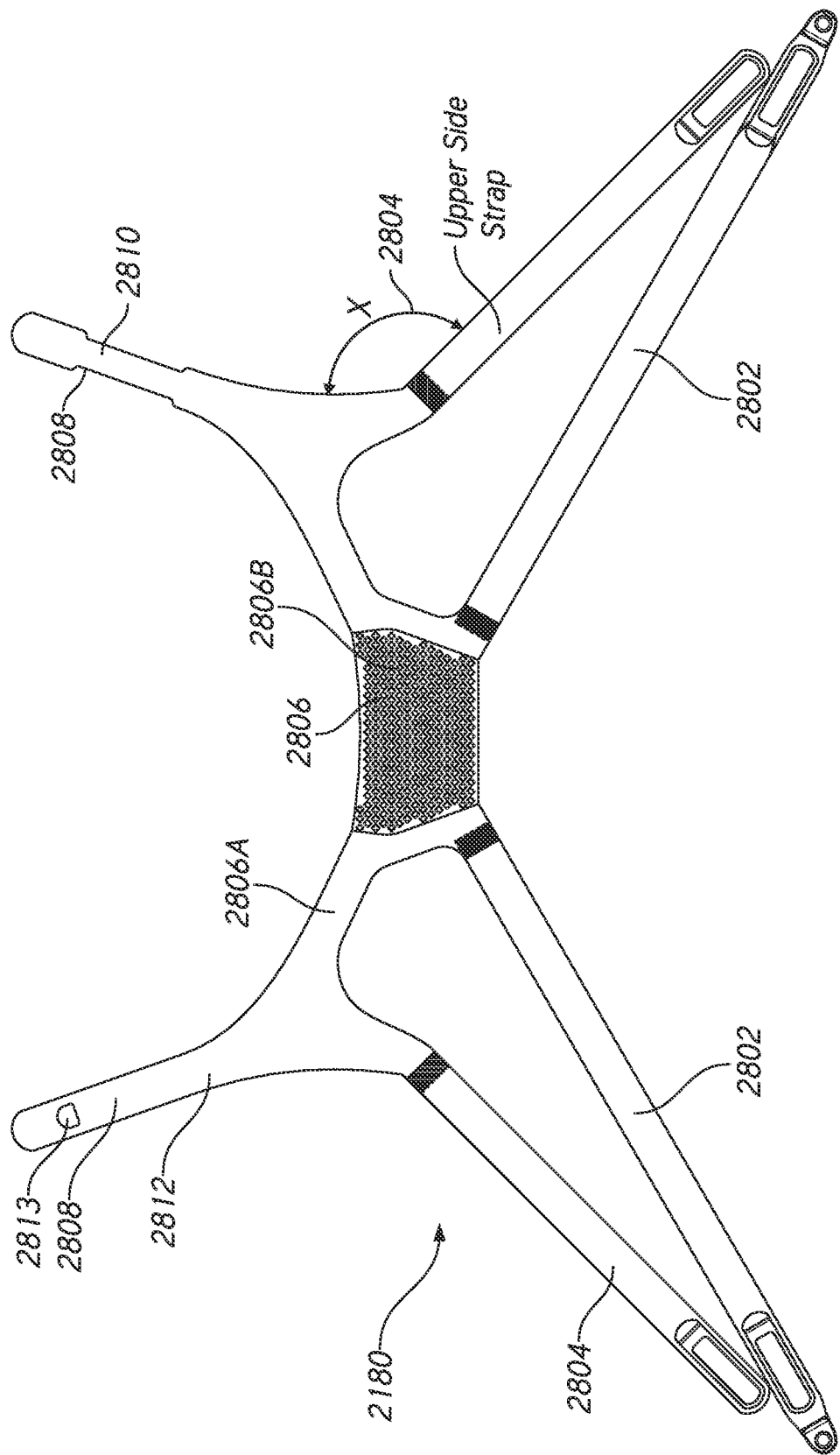
FIG. 74 is an exterior surface view of a headgear assembly in a laid flat orientation.

FIG. 73 illustrates a side view of the patient interface showing an embodiment of the headgear 2180. FIG. 74 illustrates an exterior plan view of an external surface of the headgear 2180 and FIG. 75 illustrates an interior view of an internal surface of the headgear 2180, with the headgear 2180 laid flat in both FIGS. 74 and 75. As mentioned above, the headgear 2180 can include at least two upper side straps 2804, at least two lower side straps 2802, a rear panel 2806, and/or a crown strap 2808, among other components. As shown in at least FIGS. 74 and 75, the upper side straps 2804 can be connected to the crown strap 2808 at an angle 2818. For example, the angle 2818 between the upper side straps 2804 and the crown strap 2804 can be approximately 144 degrees. In some embodiments, the angle 2818 is 130 degrees, 135 degrees, 140 degrees, 145 degrees, or 150 degrees or more. The angle 2818 allows the upper side straps 2804 to extend downwardly above the user's ears to the frame 2178 in use.

In use, the upper sides straps 2804 can be positioned on opposite sides of the headgear 2180 and can extend downwardly from the crown strap 2808 towards the mask assembly 2100. In some embodiments, the upper side straps 2804 can be configured to extend across the user's cheeks when worn. In some embodiments, the upper side straps 2804 can be adjustably and/or directly connected to the frame 2178, such as at the upper strap connectors 2702 of the frame 2178.

In some embodiments, the lower side straps 2802 can be positioned on opposite sides of the headgear 2180. In use, the lower side straps 2802 can extend substantially horizontally below the ears of the user. The lower side straps 2802 can extend from the rear panel 2806 to towards the mask assembly 2100. In some embodiments, the lower side straps 2802 can be configured to extend across the user's face when worn such as generally along the jaw of the user. In some embodiments, the lower side straps 2804 can be adjustably connected to the frame 2178. The connection between the frame 2178 and the lower side straps 2802 can include a direct and/or an indirect connection. For example, the lower side straps 2802 can be indirectly connected to the frame 2178 via the headgear clips 2600. As shown in FIGS. 73-75, the upper and lower side straps 2804, 2802 can be connected by the rear panel 2806. The connection between the upper and lower side straps 2804 at the rear panel 2806 can be positioned rearward of the user's ear in use. Such configurations can provide stability and support to the headgear 2180. Such configurations can be more comfortable to the user when worn and/or provide a more aesthetically pleasing appearance.

In some embodiments, the rear panel 2806 can be positioned at approximately the center of the headgear 2180. The rear panel 2806 can be configured to contact a rear portion of the user's head when worn. In some embodiments, the rear panel 2806 can include at least two or more portions. The rear panel 2806 can include a first portion 2806A and a second portion 2806B. The first portion 2806A can be integrally formed with the upper and lower side straps 2804, 2802. In some embodiments, the second portion 2806B can be positioned at approximately the center of the rear panel 2806. The second portion 2806B can be made at least in part by spacer fabric. An example of such a spacer fabric is disclosed in Applicant's publication no. WO 2017021836, the entirety of which is incorporated by reference herein. The spacer fabric can provide additional comfort to the user.

For example, the spacer fabric can be desirably light weight, breathable and/or form a cushioned region at the rear of the user's head. In some embodiments, the spacer fabric of the second portion can extend inwardly from the first portion 2806A of the rear panel 2806. In some embodiments, the spacer fabric can include two spacer fabric layers. For example, each of the layers can be layered on top of the other.

In some embodiments, the headgear 2180 includes the crown strap 2808. The crown strap 2808 can include a right portion 2810 and a left portion 2812. In some embodiments, the left and right portions 2812, 2810 can form a strap that extends across an upper region of the user's head, such as the crown of the user's head.

In some embodiments, the left and right portions 2812, 2810 can be adjustably coupled. In some embodiments, the left and right portions 2812, 2810 are adjustably coupled by a buckle. In some embodiments, the left portion 2812 includes an aperture 2813. The aperture 2813 can be positioned near an end of the left portion 2812 of the crown strap 2808. In some embodiments, the aperture 2813 can receive at least a portion of the right portion 2810 of the crown strap 2808. In some embodiments, the aperture 2813 allows the left portion 2812 and the right portion 2810 to be adjustably coupled. For example, the left and right portions 2812, 2810 can be slidably adjusted relative to one another. In some embodiments, the right portion 2810 includes a first recessed region 2811A and a second recessed region 2811A. The first and second recessed regions 2811A, 2811B can be formed along opposite sides of the right portion 2810. The first and second recessed regions 2811A, 2811B can be aligned with one another and positioned offset from an end of the right portion 2810. In some embodiments, the first and second recessed regions 2811A, 2811B define a region of reduced width. The region of reduced width can slide through the aperture 2813. In some embodiments, the region of reduced width can slide through the aperture 2813 with no deformation or little deformation of the left and/or right portions 2812, 2810.

Though certain embodiments are described such as the left portion 2812 having an aperture 2813 and the right portion 2810 having the first and second recessed regions 2811A, 2811B, other configurations are contemplated. For example, the right portion 2810 can include an aperture 2813 and the left portion 2812 can include the first and second recessed regions 2811A, 2811B.

In some embodiments, the upper side straps 2804, the lower side straps 2802, and/or the crown strap 2808 can include fastening features 2820. The fastening features 2820 can include one or more of a hook and a loop fastener, among other features. The fastening features 2820 can allow the headgear to be adjusted at various lengths, such as user-defined lengths. In some embodiments, the fastening features 2820 of the lower side straps 2802 and/or the upper side straps 2804 can allow the straps 2802, 2804 to be easily adjusted and/or removed from the mask assembly 2100.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to". Conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment.

The term "plurality" refers to two or more of an item. Recitations of quantities, dimensions, sizes, formulations, parameters, shapes and other characteristics should be construed as if the term "about" or "approximately" precedes the quantity, dimension, size, formulation, parameter, shape or other characteristic. The terms "about" or "approximately" mean that quantities, dimensions, sizes, formulations, parameters, shapes and other characteristics need not be exact, but may be approximated and/or larger or smaller, as desired, reflecting acceptable tolerances, conversion factors, rounding off, measurement error and the like and other factors known to those of skill in the art. Recitations of quantities, dimensions, sizes, formulations, parameters, shapes and other characteristics should also be construed as if the term "substantially" precedes the quantity, dimension, size, formulation, parameter, shape or other characteristic. The terms "approximately," "about," and "substantially" as used herein represent an amount close to the stated amount that still performs a desired function or achieves a desired result. For example, in some embodiments, as the context may dictate, the terms "approximately", "about", and "substantially" may refer to an amount that is within less than or equal to 10% of the stated amount. The term "generally" as used herein represents a value, amount, or characteristic that predominantly includes, or tends toward, a particular value, amount, or characteristic. For example, as the context may dictate, the term "generally linear" can mean something that departs from exactly parallel by less than or equal to 15°.

Numerical data may be expressed or presented herein in a range format. It is to be understood that such a range format is used merely for convenience and brevity and thus should be interpreted flexibly to include not only the numerical values explicitly recited as the limits of the range, but also interpreted to include all of the individual numerical values or sub-ranges encompassed within that range as if each numerical value and sub-range is explicitly recited. As an illustration, a numerical range of "1 to 5" should be interpreted to include not only the explicitly recited values of about 1 to about 5, but should also be interpreted to also include individual values and sub-ranges within the indicated range. Thus, included in this numerical range are individual values such as 2, 3 and 4 and sub-ranges such as "1 to 3," "2 to 4" and "3 to 5," etc. This same principle applies to ranges reciting only one numerical value (e.g., "greater than 1") and should apply regardless of the breadth of the range or the characteristics being described.

A plurality of items may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary. Furthermore, where the terms "and" and "or" are used in conjunction with a list of items, they are to be interpreted broadly, in that any one or more of the listed items may be used alone or in combination with other listed items. The term "alternatively" refers to selection of one of two or more alternatives, and is not intended to limit the selection to only those listed alternatives or to only one of the listed alternatives at a time, unless the context clearly indicates otherwise.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where, in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention and without diminishing its attendant advantages. For instance, various components may be repositioned as desired. It is therefore intended that such changes and modifications be included within the scope of the invention. Moreover, not all of the features, aspects and advantages are necessarily required to practice the present invention. Accordingly, the scope of the present invention is intended to be defined only by the claims that follow.

What is claimed is:

1. A respiratory mask comprising:
   a mask assembly including:
     a seal comprising a nasal sealing portion and an oral sealing portion, the nasal sealing portion configured to seal on an under-side of a patient's nose, the seal configured to provide a flow of breathable gas to a user's nose and mouth;
     a housing comprising a front and a back, such that in use the front of the housing is distal to the user's nose and mouth and the back of the housing is proximal to the user's nose and mouth,
     wherein the seal and housing form a breathing chamber; and
   a frame that is removably coupled to the mask assembly, the frame comprising:
     a main body defining at least one headgear connector;
     an inlet opening through which a supply of pressurized air is provided to the mask assembly; and
     an anti-asphyxia valve assembly in fluid communication with the inlet opening,
     wherein the anti-asphyxia valve assembly comprises a valve housing integrally formed with the frame,
     wherein the main body of the frame defines at least a portion of a gas flow passage of the anti-asphyxia valve assembly,
     wherein the housing defines a curved surface that is recessed into the front of the housing towards the back of the housing, wherein the curved surface accommodates at least a portion of the frame comprising the anti-asphyxia valve assembly, wherein the curved surface of the housing matches a curvature of a portion of the anti-asphyxia valve assembly.

2. The respiratory mask of claim 1, wherein the anti-asphyxia valve assembly comprises at least one vent passage and at least one valve outlet.

3. The respiratory mask of claim 1, wherein the frame comprises a tube connector coupled to the main body of the frame and configured to be connected to a breathing tube, wherein the tube connector defines the inlet opening.

4. The respiratory mask of claim 3, wherein the tube connector secures a valve member of the anti-asphyxia valve assembly to the main body of the frame, such that the valve member is in direct contact with the main body of the frame.

5. The respiratory mask of claim 3, wherein a front wall of the frame defines a portion of the gas flow passage of the respiratory mask.

6. The respiratory mask of claim 5, wherein the main body of the frame further comprises an inlet tube that defines a portion of the gas flow passage, wherein the tube connector defines the inlet opening on a first side of the tube connector, wherein the inlet tube is coupled to the tube connector on a second side of the tube connector, the second side opposing the first side.

7. The respiratory mask of claim 6, wherein the inlet tube extends downwardly from a bottom region of the front wall.

8. The respiratory mask of claim 6, wherein the inlet tube includes a front surface that defines a continuous surface with a front surface of the front wall.

9. The respiratory mask of claim 6, wherein the inlet tube is positioned at least partially rearward of the front wall.

10. The respiratory mask of claim 6, wherein the inlet tube includes a rear internal surface and a front internal surface, and wherein the rear internal surface extends away from the inlet opening and is angled toward the front internal surface.

11. The respiratory mask of claim 6, wherein the curved surface accommodates the inlet tube.

12. The respiratory mask of claim 1, wherein the frame defines a mask connector configured to secure the mask assembly to the frame, wherein the mask connector defines a portion of the gas flow passage and is configured to receive a flow of gas from the inlet opening and the anti-asphyxia valve assembly and is configured to deliver the flow of gas to the mask assembly.

13. The respiratory mask of claim 1, wherein the portion of the anti-asphyxia valve assembly comprises a rear surface of the anti-asphyxia valve assembly.

14. The respiratory mask of claim 1, wherein the nasal sealing portion comprises a left nasal sealing surface and a right nasal sealing surface, wherein an inner portion of each sealing surface nearest a nasal opening of the seal is generally flat.

15. The respiratory mask of claim 14, wherein an outer portion of each of the sealing surfaces is curved, and wherein a radius of curvature of the outer portions decreases in a rearward to forward direction within each of the outer portions.

16. The respiratory mask of claim 14, wherein an angle defined between the left and right sealing surfaces increases in a rearward to forward direction, such that an angle defined between the left and right sealing surfaces at a forward end is configured to be positioned closer to the frame than an angle defined between the left and right sealing surfaces at a rearward end.

17. The respiratory mask of claim 1, wherein the housing includes a bias vent that is positioned on opposing sides of the inlet opening and on a front surface of the housing below the frame, and wherein the bias vent is configured to exhaust air below a lower edge of the frame.

* * * * *